US012274724B2

(12) United States Patent
van den Pol

(10) Patent No.: US 12,274,724 B2
(45) Date of Patent: Apr. 15, 2025

(54) METHODS FOR TREATMENT OF CANCER USING CHIKUNGUNYA-VSV CHIMERIC VIRUS

(71) Applicant: Yale University, New Haven, CT (US)

(72) Inventor: Anthony N. van den Pol, Branford, CT (US)

(73) Assignee: YALE UNIVERSITY, New Haven, CT (US)

(*) Notice: Subject to any disclaimer, the term of this patent is extended or adjusted under 35 U.S.C. 154(b) by 918 days.

(21) Appl. No.: 17/260,930

(22) PCT Filed: Jul. 17, 2019

(86) PCT No.: PCT/US2019/042265
§ 371 (c)(1),
(2) Date: Jan. 15, 2021

(87) PCT Pub. No.: WO2020/018705
PCT Pub. Date: Jan. 23, 2020

(65) Prior Publication Data
US 2021/0290705 A1 Sep. 23, 2021

Related U.S. Application Data

(60) Provisional application No. 62/699,521, filed on Jul. 17, 2018.

(51) Int. Cl.
| | |
|---|---|
| *A61K 35/766* | (2015.01) |
| *A61K 38/16* | (2006.01) |
| *A61K 45/06* | (2006.01) |
| *A61P 35/00* | (2006.01) |

(52) U.S. Cl.
CPC ......... *A61K 35/766* (2013.01); *A61K 38/162* (2013.01); *A61K 45/06* (2013.01); *A61P 35/00* (2018.01)

(58) Field of Classification Search
CPC .... A61K 35/766; A61K 38/162; A61K 45/06; A61P 35/00
See application file for complete search history.

(56) References Cited

U.S. PATENT DOCUMENTS

| | | |
|---|---|---|
| 7,429,481 B2 | 9/2008 | Bergman |
| 10,179,154 B2 | 1/2019 | Van Den Pol |
| 2007/0026012 A1 | 2/2007 | Delisa |
| 2007/0218078 A1 | 9/2007 | Clarke |
| 2009/0047234 A1 | 2/2009 | Touitou |
| 2009/0175906 A1 | 7/2009 | Kalyan |
| 2009/0252672 A1 | 10/2009 | Eddington |
| 2012/0171246 A1 | 7/2012 | Van Den Pol |
| 2016/0296572 A1* | 10/2016 | Van Den Pol ......... A61P 35/00 |

FOREIGN PATENT DOCUMENTS

| | | |
|---|---|---|
| WO | 2010080909 | 7/2010 |
| WO | 2015077714 | 5/2015 |
| WO | 2015134332 | 9/2015 |

OTHER PUBLICATIONS

Van den Pol AN, Mao G, Chattopadhyay A, Rose JK, Davis JN. Chikungunya, Influenza, Nipah, and Semliki Forest Chimeric Viruses with Vesicular Stomatitis Virus: Actions in the Brain. J Virol. Feb. 2, 20178;91(6):e02154-16. (Year: 2017).*
Chattopadhyay A, Wang E, Seymour R, Weaver SC, Rose JK. A chimeric vesiculo/alphavirus is an effective alphavirus vaccine. J Virol. Jan. 2013;87(1):395-402. (Year: 2013).*
Ahmed, et al., "Identification of a consensus mutation in M protein of vesicular stomatitis virus from persistently infected cells that affects inhibition of host-directed gene expression", Virology, 237(2):378-388 (1997).
Ahmed, "Immune response in the absence of neurovirulence in mice infected with m protein mutant vesicular stomatitis virus", J. Virol., 82(18):9273-9277 (2008).
Ali, et al., "Combined immunostimulation and conditional cytotoxic gene therapy provide long-term survival in a large glioma model", Cancer Res, 65(16):7194-7204 (2005).
Amdekar, et al., "Chikungunya Virus-Induced Arthritis: Role of Host and Viral Factors in the Pathogenesis", Virol. Immunol., 30(10):691-702 (2017).
Aungst, et al., "Intestinal permeation enhancers", J. Pharm. Sci. 89(4):429-442 (2000).
Bainbridge, et al., "Stable rAAV-mediated transduction of rod and cone photoreceptors in the canine retina", Gene Ther., 10(16):1336-44 (2003).
Barzon, et al., "HSV-TK/IL-2 gene therapy for glioblastoma multiforme", Methods Mol. Biol., 542:529-549 (2009).
Bergmann, et al., "Vesicular stomatitis virus expressing a chimeric Sindbis glycoprotein containing an Fe antibody binding domain targets to Her2/neu overexpressing breast cancer cells", Virology, 316(2): 337-347 (2003).

(Continued)

*Primary Examiner* — Nicole Kinsey White
*Assistant Examiner* — Ruixue Wang
(74) *Attorney, Agent, or Firm* — PABST PATENT GROUP LLP

(57) ABSTRACT

Chimeric viruses having a vesicular stomatitis virus (VSV) background where the VSV G protein is supplemented or replaced with an alphavirus glycoprotein(s), or a functional fragment(s) thereof, are provided. A preferred alphavirus is Chikungunya virus. In particular embodiments, the glycoprotein(s) is or includes E3, E2, K6, and E1 proteins of an alphavirus, preferably Chikungunya virus. Methods of using the chimeric viruses for treatment of cancers, particularly brain cancers and metastasis thereof are also provided. In some embodiments, the chimeric viruses retain superior oncolytic activity to infect and destroy cancer cells selectively, such as glioblastoma and intracranial melanoma metastases. In some embodiments, the chimeric viruses have reduced toxicity to e.g., heathy cells relative to a control such as the parent VSV with the VSV G protein.

20 Claims, 9 Drawing Sheets
Specification includes a Sequence Listing.

(56) References Cited

OTHER PUBLICATIONS

Bernard, et al., "Endocytosis of Chikungunya Virus into Mammalian Cells: Role of Clathrin and Early Endosomal Compartments", PLoS One, 5: e11479, 11 pages (2010).
Chateauvieux, et al., "Molecular and therapeutic potential and toxicity of valproic acid", J. Biomed. Biotechnol., 479364 (2010).
Chattopadhyay, et al., "A Chimeric Vesiculo/Alphavirus Is an Effective Alphavirus Vaccine", J. Virol., 87(1):395-402 (2013).
Clarke, et al., "Synergistic attenuation of vesicular stomatitis virus by combination of specific G gene truncations and N gene translocations", J. Virol., 81(4):2056-2064 (2007).
Clarke, et al., "Recombinant vesicular stomatitis virus as an HIV-1 vaccine vector", Springer Semin. Immunopathol., 28(3):239-253 (2006).
Cooper, et al., "Attenuation of recombinant vesicular stomatitis virus-human immunodeficiency virus type 1 vaccine vectors by gene translocations and g gene truncation reduces neurovirulence and enhances immunogenicity in mice", J. Virol., 82(1):207-219 (2008).
Dalton, et al., "Vesicular stomatitis virus glycoprotein containing the entire green fluorescent protein on its cytoplasmic domain is incorporated efficiently into virus particles", Virology, 279(2):414-421 (2001).
Doi, et al., "Transient immunosuppression stops rejection of virus-transduced enhanced green fluorescent protein in rabbit retina", J. Virol., 78(20): 11327-33 (2004).
Drake, et al., "Mutation rates among RNA viruses", Proc. Natl. Acad. Sci. USA, 96(24):13910-13913 (1999).
Finkelshtein, et al., "LDL receptor and its family members serve as the cellular receptors for vesicular stomatitis virus", Pro. Natl. Acad. Sci. USA, 110(18):7306-7311 (2013).
Flanagan, et al., "Vesicular stomatitis viruses with rearranged genomes have altered invasiveness and neuropathogenesis in mice", J. Virol., 77(10):5740-5748 (2003).
Flanagan, et al., "Rearrangement of the genes of vesicular stomatitis virus eliminates clinical disease in the natural host: new strategy for vaccine development", J. Virol., 75(13):6107-6114 (2001).
Fu, et al., "Autophagy induced by valproic acid is associated with oxidative stress in glioma cell lines", Neuro. Oncol., 12(4):328-340 (2010).
Fukuhara, et al., "Oncolytic herpes simplex virus type 1 and host immune responses", Curr. Cancer Drug Targets, 7(2):149-155 (2007).
Garbutt, et al., "Properties of replication-competent vesicular stomatitis virus vectors expressing glycoproteins of filoviruses and arenaviruses", J Viral., 78(10):5458-65 (2004).
Garmashova, et al., "The Old World and New World alphaviruses use different virus-specific proteins for induction of transcriptional shutoff", Journal of Virology, 81(5):2472-2484 (2007).
Geisbert, et al., "Development of a new vaccine for the prevention of Lassa fever", PLoS Med., 2(6):e183, 9 pages (2005).
Geisbert, et al., "Single-injection vaccine protects nonhuman primates against infection with marburg virus and three species of ebola virus", J. Virol., 83(14):7296-7304 (2009).
Geisbert, et al., "Vesicular stomatitis virus-based ebola vaccine is well-tolerated and protects immunocompromised nonhuman primates", PloS Pathog., 4(11):e1000225, 9 pages (2008).
Glaser, et al., "HDAC inhibitors: clinical update and mechanism-based potential", Biochem. Pharmacol., 74(5):659-671 (2007).
Hervas-Stubbs, et al., "CD8 T cell priming in the presence of IFN-α renders CTLs with improved responsiveness to homeostatic cytokines and recall antigens: important traits for adoptive T cell therapy", J. Immunol., 189(7):3299-310 (2012).
Hoornweg, et al., "Dynamics of Chikungunya Virus Cell Entry Unraveled by Single-Virus Tracking in Living Cells", J. Virol., 90(9):4745-4756 (2016).
Hua, et al., "Chikungunya Virus-Associated Disease", Curr. Rheumatol. Rep., 19(11):69 (2017).
Huneycutt, et al., "Central neuropathogenesis of vesicular stomatitis virus infection of immunodeficient mice", J. Virol., 67(11):6698-6706 (1993).
Jia, et al., "Multifunctional nanoparticles for targeted delivery of immune activating and cancer therapeutic agents", J. of Contr. Rel., 172:1020-1034 (2013).
Jinush, et al., "Cytokine gene-mediated immunotherapy: current status and future perspectives", Cancer Science, 100(8):1389-1396 (2005).
Johnson, et al., "Neurovirulence properties of recombinant vesicular stomatitis virus vectors in non-human primates", Virology, 360(1):36-49 (2007).
Jones, et al., "Live attenuated recombinant vaccine protects non-human primates against Ebola and Marburg viruses", Nat. Med., 11(7):786-790 (2005).
Kahn, et al., "Recombinant vesicular stomatitis virus expressing respiratory syncytial virus (RSV) glycoproteins: RSV fusion protein can mediate infection and cell fusion", Virology, 254(1):81-91 (1999).
Kurup, et al., "Rhabdovirus-based vaccine platforms against henipaviruses", J. Virol., 89(1):144-154 (2015).
Lawson, et al., "Recombinant vesicular stomatitis viruses from DNA", PNAS, 92(10):4477-4481 (1995).
Lun, et al., "Efficacy of systemically administered oncolytic vaccinia virotherapy for malignant gliomas is enhanced by combination therapy with rapamycin or cyclophosphamide", Clin. Cancer Res., 15(8):2777-2788 (2009).
Lundh, et al., "Non-lethal infection of aminergic reticular core neurons: age-dependent spread of ts mutant vesicular stomatitis virus from the nose", J. Neuropathol. Exp. Neurol., 47(5):497-506 (1988).
Lundh, et al., "Selective infections of olfactory and respiratory epithelium by vesicular stomatitis and Sendai viruses", Neuropathol. Appl. Neurobiol., 13(2):111-122 (1987).
Lyles, "Cytopathogenesis and inhibition of host gene expression by RNA viruses", Microbial. Mol. Biol. Rev., 64(4):709-724 (2000).
Lyles, et al., "Rhabdoviridae", Fields virology, 5th ed, Lippincott Williams & Wilkins, 1(39):1363-1408 (2007).
Mactavish, et al., "Enhancement of vaccinia virus based oncolysis with histone deacetylase inhibitors", PLoS One, 5(12):e14462, 9 pages (2010).
Muik, et al., "Pseudotyping vesicular stomatitis virus with lymphocytic choriomeningitis virus glycoproteins enhances infectivity for glioma cells and minimizes neurotropism", Journal of Virology, The American Society for Microbiology, 85(11): 5679-5684 (2011).
Nguyen, et al., "Chemical targeting of the innate antiviral response by histone deacetylase inhibitors renders refractory cancers sensitive to viral oncolysis", Proc. Natl. Acad. Sci., 105(39): 14981-14986 (2008).
Obuchi, et al., "Development of recombinant vesicular stomatitis viruses that exploit defects in host defense to augment specific oncolytic activity", J. Virol., 77(16):8843-8856 (2003).
Otsuki, et al., "Histone Deacetylase Inhibitors Augment Antitumor Efficacy of Herpes-based Oncolytic Viruses", Mol. Ther., 16(9): 1546-1555 (2008).
Ozduman, et al., "Systemic vesicular stomatitis virus selectively destroys multifocal glioma and metastatic carcinoma in brain", J. Neurosci., 28(8):1882-1893 (2008a).
Ozduman, et al., "Peripheral immunization blocks lethal actions of vesicular stomatitis virus within the brain", J. Virol., 83(22):11540-11549 (2008b).
Paglino, et al., "Vesicular stomatitis virus has extensive oncolytic activity against human sarcomas: rare resistance is overcome by blocking interferon pathways", J. Virol., 85(18):9346-58 (2011).
Pattnaik, et al., "Infectious defective interfering particles of VSV from transcripts of a cDNA clone", Cell, 69(6):1011-1020 (1992).
Peng, et al., "Non-invasive in vivo monitoring of trackable viruses expressing soluble marker peptides", Nat. Med., 8(5):527-531 (2002).
Phuong, et al., "Use of a vaccine strain of measles virus genetically engineered to produce carcinoembryonic antigen as a novel therapeutic agent against glioblastoma multiforme", Cancer Res., 63(10):2462-2469 (2003).

(56) References Cited

OTHER PUBLICATIONS

Pol, et al., "Relative Neurotropism of a Recombinant Rhabdovirus Expressing a Green Fluorescent Envelope Glycoprotein", J. Virol., 76(3):1309-1327 (2002).
Powers, "Vaccine and Therapeutic Options to Control Chikungunya Virus", Clin. Microbial. Rev., 31:e00104-16 (2018).
Roberts, et al., "Attenuated vesicular stomatitis viruses as vaccine vectors", J. Virol. 73(5):3723-3732 (1999).
Rose, et al., "An effective AIDS vaccine based on live attenuated vesicular stomatitis virus recombinants", Cell, 106(5):539-549 (2001).
Schnell, et al., "Requirement for a non-specific glycoprotein cytoplasmic domain sequence to drive efficient budding of vesicular stomatitis virus", EMBO Journal, 17(5):1289-1296 (1998).
Schnell, et al., "The minimal conserved transcription stop-start signal promotes stable expression of a foreign gene in vesicular stomatitis virus", J. Virol., 70(4):2318-2323 (1996a).
Schnell, et al., "Foreign glycoproteins expressed from recombinant vesicular stomatitis viruses are incorporated efficiently into virus particles", PNAS, 93(21): 11359-11365 (1996b).
Schwartz, et al., "Biology and pathogenesis of chikungunya virus", Nat. Rev. Microbial., 8(7):491-500 (2010).
Shashkova, et al., "Anticancer activity of oncolytic adenovirus vector armed with IFN-alpha and ADP is enhanced by pharmacologically controlled expression of TRAIL", Cancer Gene Ther., 15(2):61-72 (2008).
Simon, et al., "Replication and propagation of attenuated vesicular stomatitis virus vectors in vivo: vector spread correlates with induction of immune responses and persistence of genomic RNA", J. Virol., 81(4):2078-82 (2007).
Solignat, et al., "Replication cycle of chikungunya: a re-emerging arbovirus", Virology, 393(2):183-197 (2009).
Stojdl, et al., "Exploiting tumor-specific defects in the interferon pathway with a previously unknown oncolytic virus", Nat. Med., 6(7):821-825 (2000).
Stojdl, et al., "VSV strains with defects in their ability to shutdown innate immunity are potent systemic anti-cancer agents", Cancer Cell, 4(4):263-275 (2003).
Strauss, et al., "The alphaviruses: gene expression, replication, and evolution", Microbiological Reviews, 58(3):491-562 (1994).
Su, et al., "Phase 1 study of valproic acid in pediatric patients with refractory solid or CNS tumors: a children's oncology group report", Clin. Cancer Res., 17(3):589-597 (2011).
Taylor, et al., "Effects of an In-Frame Deletion of the 6k Gene Locus from the Genome of Ross River Virus", J. Virol., 90(8):4150-4159 (2016).
Uchime, et al., "The role of E3 in pH protection during alphavirus assembly and exit", J. Virol., 87(18):10255-10262 (2013).
Van Den Pol, et al., "Highly attenuated recombinant vesicular stomatitis virus VSV-12'GFP displays immunogenic and oncolytic activity", J. Virol., 87(2):1019-1034 (2013).
Van Den Pol, et al., "Calcium excitability and oscillations in suprachiasmatic nucleus neurons and glia in vitro", J. Neurosci., 12(7):2648-2664 (1992).
Van Den Pol, et al., "Chikungunya, Influenza, Nipah, and Semliki Forest Chimeric Viruses with Vesicular Stomatitis Virus: Actions in the Brain", J. Virol., 91(6): e02154-16 (2017).
Van Den Pol, et al., "Differential neurite growth on astrocyte substrates: interspecies facilitation in green fluorescent protein-transfected rat and human neurons", Neuroscience, 95(2):603-616 (2000).
Vignuzzi, et al., "The Bridges and Blockades to Evolutionary Convergence on the Road to Predicting Chikungunya Virus Evolution", Annu. Rev. Virol., 4(1):181-200 (2017).
Voss, et al., "Glycoprotein organization of Chikungunya virus particles revealed by X-ray crystallography", Nature, 468(7324):709-712 (2010).
Vu, et al., "Chikungunya Virus", Clin. Lab Med., 37(2):371-382 (2017).
Wagner, et al., "Combined treatment of pediatric high-grade glioma with the oncolytic viral strain MTH-68/H and oral valproic acid", APMIS, 114(10):731-743 (2006).
Wang, et al., "Adoptive transfer of tumor-primed, in vitro—activated, CD4+ T effector cells (TEs) combined with CD8+ TEs provides intratumoral TE proliferation and synergistic antitumor response", Blood, 109(11):4865-4872 (2007).
Wei, et al., "Identification of differentially expressed genes regulated by transcription factors in glioblastomas by bioinformatics analysis", Mol. Med. Rep., 11(4):2548-2554 (2015).
Whelan, et al., "Efficient recovery of infectious vesicular stomatitis virus entirely from cDNA clones", Proc. Natl. Acad. Sci. U.S.A., 92(18):8388-92 (1995).
Wichit, et al., "Imipramine Inhibits Chikungunya Virus Replication in Human Skin Fibroblasts through Interference with Intracellular Cholesterol Trafficking", Sci. Rep., 7(1):3145 (2017).
Wintachai, et al., "Identification of prohibitin as a Chikungunya virus receptor protein", J. Med. Virol., 84(11):1757-1770 (2012).
Wollmann, et al. "Variable deficiencies in the interferon response enhance susceptibility to vesicular stomatitis virus oncolytic actions in glioblastoma cells but not in normal human glial cells", J. Virol., 81(3): 1479-1491 (2007).
Wollmann, et al., "Some attenuated variants of vesicular stomatitis virus show enhanced oncolytic activity against human glioblastoma cells relative to normal brain cells", J. Virol, 84(3):1563-73 (2010).
Wollmann, et al., "Vesicular stomatitis virus variants selectively infect and kill human melanomas but not normal melanocytes", J. Virol., 87(12):6644-6659 (2013).
Wollmann, et al., "Targeting human glioblastoma cells: comparison of nine viruses with oncolytic potential", J. Virol., 79(10): 6005-6022 (2005).
Wollmann, et al., "Lassa-Vesicular Stomatitis Chimeric Virus Safely Destroys Brain Tumors", J. Virol., 89(13):6711-6724 (2015).
Wongthida, et al., "Activating systemic T-cell immunity against self tumor antigens to support oncolytic virotherapy with vesicular stomatitis virus", Hum. Gene Ther., 22(11):1343-53 (2011).
Workman, et al., "The Development and Function of Regulatory T Cells", Cell. Mol. Life Sci., 66(16):2603-2622 (2009).
Yang, et al., "Regulatory considerations in development of vaccines to prevent disease caused by Chikungunya virus", Vaccine, 35(37):4851-4858 (2017).
Yarde, et al., "Meningeal myeloma deposits adversely impact the therapeutic index of an oncolytic VSV", Cancer Gene Ther., 20(11):616-621 (2013).
Zhang, et al., "Chikungunya-vesicular stomatitis chimeric virus targets and eliminates brain tumors," Virology, 522: 244-259 (2018).
International Search report for corresponding PCT application PCT/US2019/042265 dated Sep. 16, 2019.

\* cited by examiner

METHODS FOR TREATMENT OF CANCER USING CHIKUNGUNYA-VSV CHIMERIC VIRUS

CROSS-REFERENCE TO RELATED APPLICATIONS

This application is a National Phase application under 35 U.S.C. § 371 of International Application No. PCT/US2019/042265, filed on Jul. 17, 2019, which claims the benefit of and priority to U.S. Ser. No. 62/699,521, filed Jul. 17, 2018, which are specifically incorporated by reference herein in their entirety.

STATEMENT REGARDING FEDERALLY SPONSORED RESEARCH

This invention was made with government support under Grants R01 CA175577, R01 CA161048, and R01 CA188359, awarded by the National Institute of Health. The Government has certain rights in the invention.

REFERENCE TO SEQUENCE LISTING

The Sequence Listing submitted as a text file named "YU_7500_PCT_ST25.txt," created on Jul. 17, 2019, and having a size of 56,485 bytes is hereby incorporated by reference pursuant to 37 C.F.R § 1.52(e)(5).

FIELD OF THE INVENTION

This invention is generally directed to Chikungunya-vesicular stomatitis virus (VSV) chimeric virus and the methods of use thereof to treat cancer, particularly glioblastoma and melanoma.

BACKGROUND OF THE INVENTION

Vesicular stomatitis virus (VSV) is an enveloped, negative-sense, single-strand RNA virus in the Rhabdoviridae family. While rarely causing disease in humans, the virus can pose a potential threat to livestock including cattle, horses, and pigs (Lyles, et al., *Fields virology*, 5$^{th}$ ed, *Lippincott Williams & Wilkins*, 1363-1408 (2007)). In recent years, recombinant altered versions of VSV have shown considerable potential as the molecular basis for live vaccines engineered to express antigenic proteins from other viruses (Kurup, et al., *J. Virol.*, 89:144-154 (2015); Clarke, et al., Springer Semin. Immunopathol., 28:239-253 (2006); Geisbert, et al., *PloS Pathog.*, 4:e1000225 (2008); Geisbert, et al., *J. Virol.*, 83:7296-7304 (2009)). VSV has also shown promise as an oncolytic virus (Wongthida, et al., *Hum. Gene. Ther.*, 22:1343-1353 (2011); Obuchi, et al., *J. Virol.*, 77:8843-8856 (2003); Ozduman, et al., *J. Virol.*, 83:11540-11549 (2008); van den Pol, et al., *J. Virol.*, 87:1019-1034 (2013); Wollmann, et al., *J. Virol.*, 79:6005-6022 (2005)). However, a substantive limitation of VSV is that the VSV glycoprotein is highly neurotropic, and upon entering the brain, can lead to deleterious neurological consequences, including death (Huneycutt, et al., *J. Virol.*, 67:6698-6706 (1993); Lundh, et al., *Neuropathol. Appl. Neurobiol.*, 13:111-122 (1987); Lundh, et al., *J. Neuropathol. Exp. Neurol.*, 47:497-506 (1988); van den Pol, et al., *J. Virol.*, 76:1309-1327 (2002)). VSV has been proposed to utilize the LDL receptor as an entry port (Finkelshtein, et al., *Pro. Natl. Acad. Sci. USA*, 110:7306-7311 (2013)).

Although substitution of glycoprotein genes from other viruses can reduce VSV neurotropism (Wollmann, et al., *J. Virol.*, 89:6711-6724 (2015); van den Pol, et al., *J. Virol.*, 91:e02154-16 (2017)), the attenuation of neurotropism is not necessarily a universal attribute of chimeric VSVs. Glycoproteins from some viruses that have been substituted for the VSV glycoprotein can be maladaptive and enhance neurotropism; for example the replication competent Nipah-VSV chimera is lethal in the brain (van den Pol, et al., *J. Virol.*, 91:e02154-16 (2017)). Even for the potential treatment of non-brain cancers with oncolytic viruses, the importance of attenuating or eliminating the neurotropism of VSV is illustrated by data showing that metastatic myeloma cancer cells can form a bridge from outside the brain across the meninges into the brain, potentially serving as a conduit through the blood brain barrier for a neurotropic virus to enter the brain (Yarde, et al., *Cancer Gene Ther.*, 20:616-621 (2013)). Thus, there remains a need for improved VSV chimera virus and methods of use therefore for selectively infecting and cytolytically killing tumor cells without substantive damage to normal cells.

Therefore, it is an object of the invention to provide recombinant oncolytic viruses, preferably with improved safety and superior cytolytic profiles.

It is a further object of the invention to provide pharmaceutical compositions including an effective amount of recombinant oncolytic viruses to treat cancer in a human subject.

It is another object of the invention to provide methods of using recombinant oncolytic virus to kill cancer cells.

It is a further object of the invention to increase the body's immune response against cancer cells.

It is a further object to generate a safer virus-based vaccine against other non-related microbial antigens.

SUMMARY OF THE INVENTION

Chimeric viruses, including Chikungunya-vesicular stomatitis chimeric viruses (CHIKV-VSV), and pharmaceutical compositions and methods of use thereof for treating cancer are provided. The chimeric viruses are based on a VSV background where the VSV G protein is replaced with one or more alphavirus, preferable Chikungunya virus, glycoproteins. In the most preferred embodiment, the VSV G protein is replaced with the glycoprotein from Chikungunya virus or a functional fragment thereof. The Examples below show that replacement of the VSV G protein with a heterologous glycoprotein, particularly the glycoprotein from Chikungunya virus, results in a virus that retains superior oncolytic activity to infect and destroy cancer cells such as glioblastoma and intracranial melanoma metastases, in both in vitro and in vivo studies. The CHIKV-VSV chimeric virus eliminates tumor with little or no infection of normal or healthy cells, and extended survival substantially. The chimeric virus can be further modified to express one or more therapeutic proteins, reporters, vaccine antigens, or targeting moieties.

The methods typically including administering to a subject with cancer a pharmaceutical composition including an effective amount of chimeric virus. Methods can include administering to a subject an effective amount of the virus to reduce one or more symptoms of cancer, for example tumor burden. The cancer can be multiple myeloma, bone, bladder, brain, breast, cervical, colo-rectal, esophageal, kidney, liver, lung, nasopharyngeal, pancreatic, prostate, skin, stomach, and uterine. In a preferred embodiment, the methods are used to treat brain cancer and brain metastases. Brain cancers include, but are not limited to, oligodendroglioma, meningioma, supratentorial ependymona, pineal region tumors, medulloblastoma, cerebellar astrocytoma, infratentorial ependymona, brainstem glioma, schwannomas, pituitary tumors, craniopharyngioma, optic glioma, and astrocytoma. In a particularly preferred embodiment, the cancer is glioblastoma or melanoma.

The virus is typically administered in a dosage of between about $10^2$ and about $10^{12}$ PFU, more preferably between about $10^2$ and about $10^{12}$ PFU. The pharmaceutical composition can be administered locally to the site of the cancer. For example, the composition can be injected into or adjacent to a tumor in the subject, or via catheter into a tumor resection cavity, for example, by convection-enhanced delivery (CED). The pharmaceutical composition can be administered systemically to the subject, for example by intravenous, intra-muscular, subcutaneous, or intrathecal injection or infusion, or used ex vivo.

The virus can be administered in combination with one or more additional therapeutic agents. The one or more additional therapeutic agents can be, for example, an anticancer agent such as a chemotherapeutic agent, a therapeutic protein such as IL-2, or an immunosuppressant. The immunosuppressant can be a histone deacetylase (HDAC) inhibitor or an interferon blocker, for example, valproate, the vaccinia protein B18R, Jak inhibitor 1, or vorinostat, which can be used to reduce or delay the subject's immune response to the virus.

The pharmaceutical composition can be administered in combination with surgery. In some embodiments, the subject is pre-treated with an immunizing composition including a virus effective to immunize the subject to the chimeric VSV prior to administration of the pharmaceutical composition. The virus in the immunizing composition can be the chimeric VSV Immunizing the subject against the virus can increase the ability of the subject's immune system to clear the virus following therapeutic treatment if needed.

Other methods of treating cancer are also disclosed. For example, a method of treating a subject for cancer can include (a) infecting isolated cancer cells with an effective amount of a Chikungunya-VSV chimeric virus and (b) administrating the infected cells to the subject in an effective amount to induce an immune response against the cancer cells in the subject. In some embodiments, the method includes irradiating the cells to prevent their proliferation in the subject. The method can be used to therapeutically or prophylactically treat cancer in the subject.

Methods of priming the immune system for attacking cancer cells and adaptive T cell therapy are also disclosed. The priming can occur in vitro or in vivo. A particular embodiment of preparing cells for adaptive T cell therapy includes administering to a subject with cancer a pharmaceutical composition including an effective amount of a chimeric VSV to increase the number of cytotoxic T cells (CTL) which can directly kill the cancer, or to increase the number of CD4+ T and/or CD8+ T cells which can direct an immune response against the cancer. The T cells can be isolated from the subject and propagated in vitro. The T cells can be administered back to the same subject, or another subject in need thereof.

Pharmaceutical dosage units and kits including an effective amount of the chimeric viruses are also provided.

BRIEF DESCRIPTION OF THE DRAWINGS

Figures 1A, 1B, 2A:
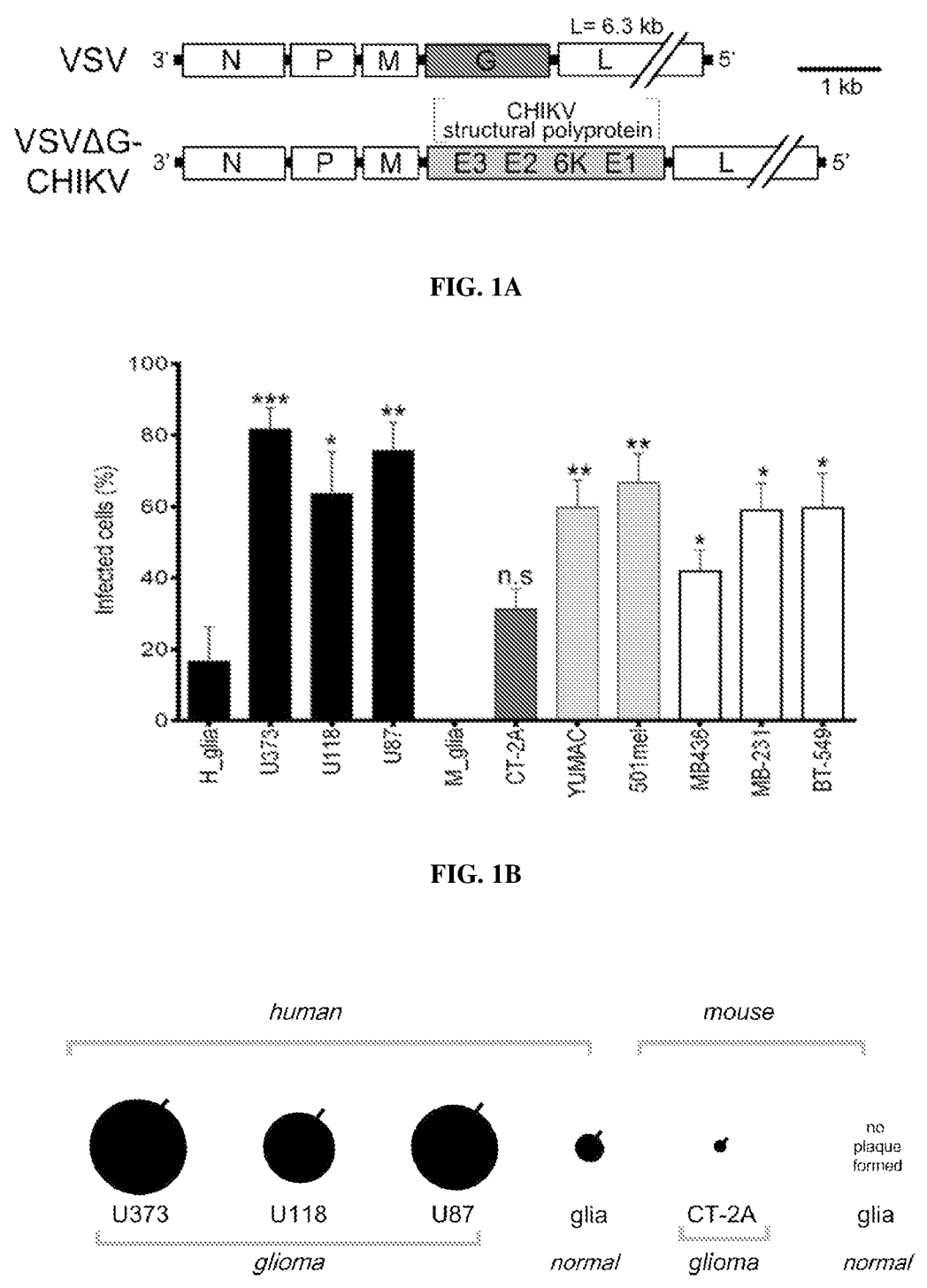

FIG. 1A is a schematic illustration showing genomes of wild-type VSV (top) and chimeric VSVΔG-CHIKV (bottom) in which the VSV glycoprotein G gene has been replaced with the Chikungunya glycoprotein sequence (E3, E2, 6K, E1) from the CHIKV structural polyprotein. FIG. 1B is a bar graph showing the percentage of infected cells in tumor cells and the normal human cells (glia). Values are reported as the mean+/−SEM; n=6. ns, not significant, *p<0.05, p<0.01, *p<0.001 one-way ANOVA with repeated measures.

FIG. 2A shows VSVΔG-CHIKV plaque sizes measured as an indicator of viral propagation in human and mouse glioma. Each black circle shows the mean size of 20 randomly selected plaques with the SEM indicated by the black line on the upper right of each circle.

Figures 4A, 4B:
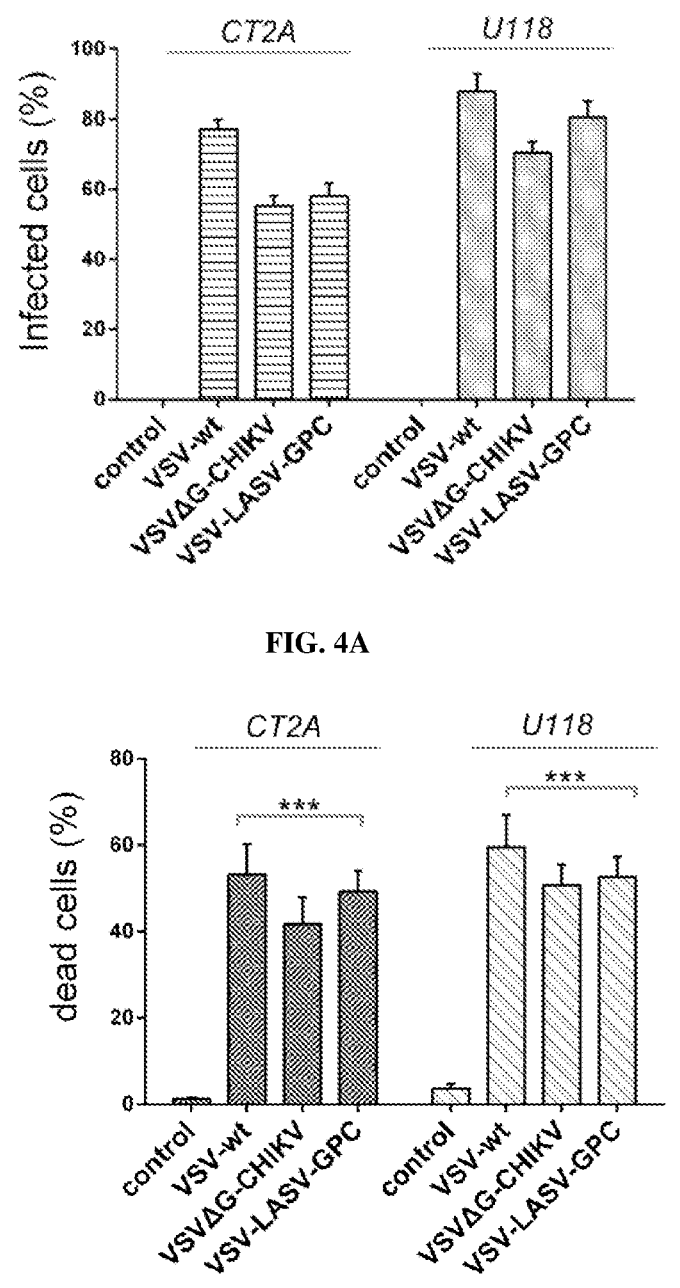
Figures 4C, 4D:
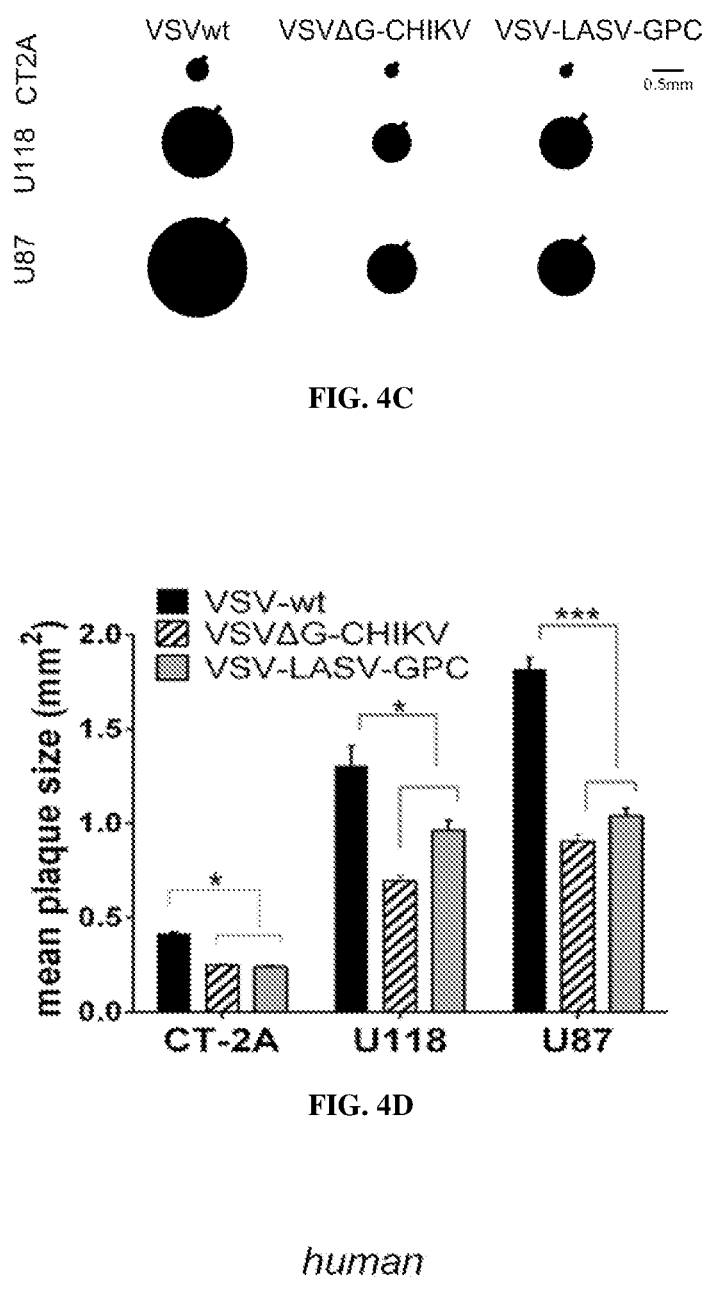

FIG. 4A is a bar graph showing the mean percentage of infected cells with VSVΔG-CHIKV one day post-infection, n=6 and *p<0.001 one-way ANOVA with repeated measures. FIG. 4B is a bar graph showing the mean percentage of the dead cells one day post-infection, n=6 and *p<0.001 one-way ANOVA with repeated measures. FIG. 4C is a diagram showing the relative size of viral plaques that developed 48 hr post-infection on monolayer cultures of human (U118, U87) and mouse (CT-2A) glioma cells using VSVΔG-CHIKV, VSVwt and VSV-LASV-GPC. Each circle depicts the mean plaque size of 20 randomly selected plaques. FIG. 4D is a bar graph showing the mean plaque sizes in mm$^2$+/−SEM; n=20.

DETAILED DESCRIPTION OF THE INVENTION

I. Definitions

Figure 2B:
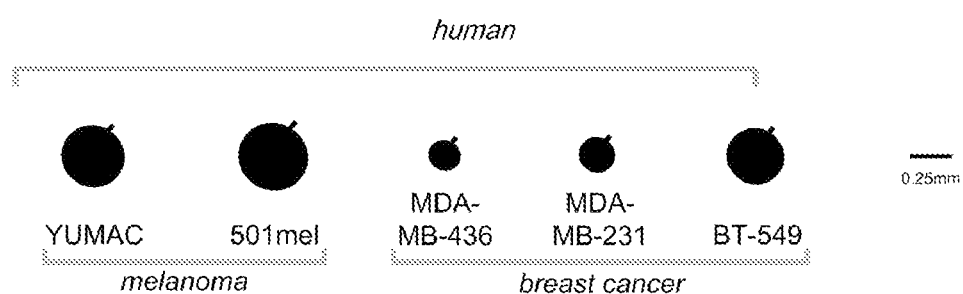
FIG. 2B shows the plaque sizes measured in human melanoma and breast cancer cells. Scale bar 0.25 mm
Figure 2C:
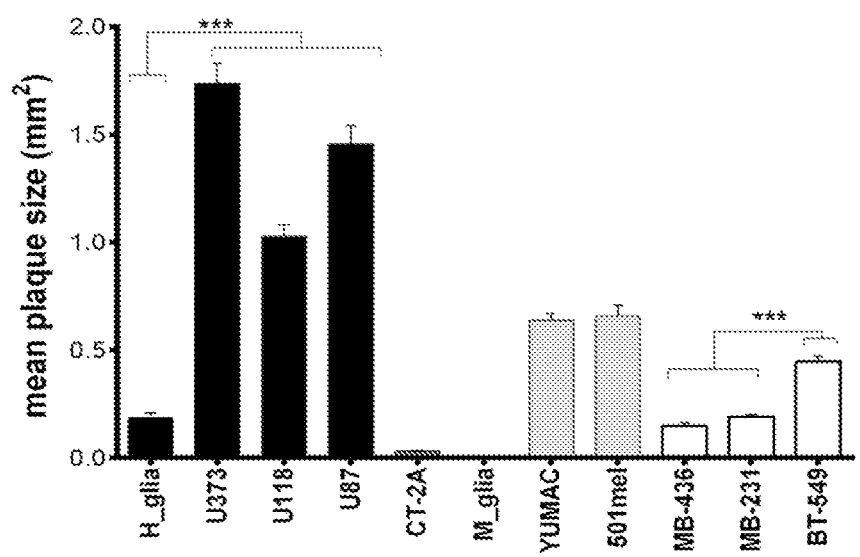
FIG. 2C is a bar graph showing the mean plaque size of cells. Values are reported as the mean+/−SEM; n=20. *p<0.05, p<0.01, *p<0.001, one-way ANOVA with repeated measures.
Figure 3A:
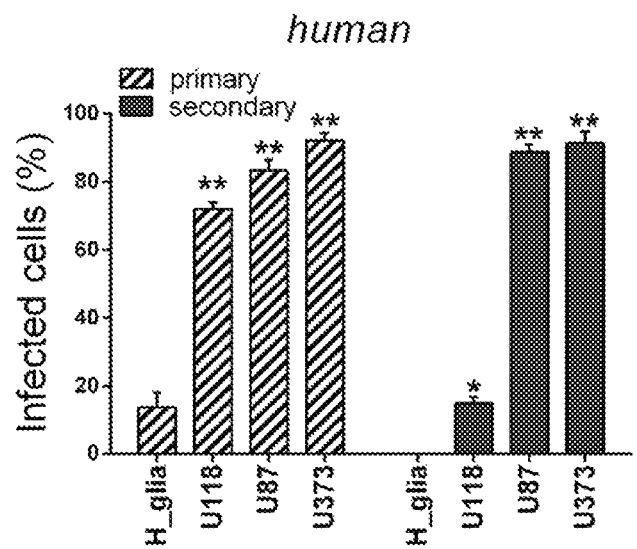
FIG. 3A is a bar graph showing the percentage of infected human glioblastoma cells with VSVΔG-CHIKV at an MOI of 0.02 (primary inoculation). Values are reported as the mean+/−SEM; n=6. *p<0.05, p<0.01 vs. normal cells; one-way ANOVA with repeated measures.
Figure 3B:
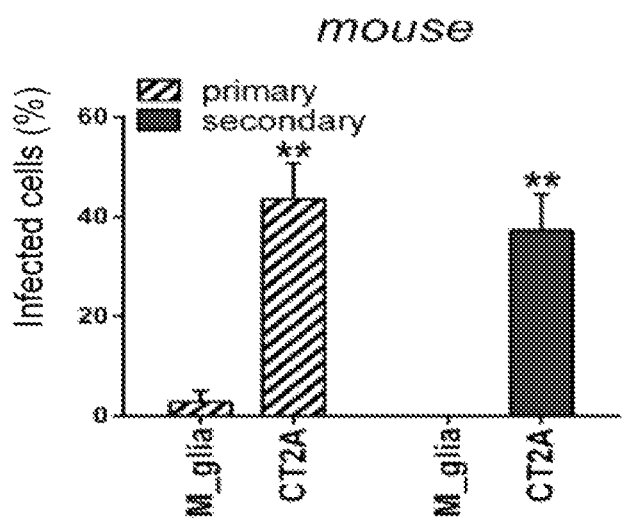
FIG. 3B** is a bar graph showing the percentage of infected mouse glioma cells with VSVΔG-CHIKV at an MOI of 0.02 (primary inoculation). Values are reported as the mean+/−SEM; n=6. *p<0.05, **p<0.01 vs. normal cells; one-way ANOVA with repeated measures.
Figure 5A:
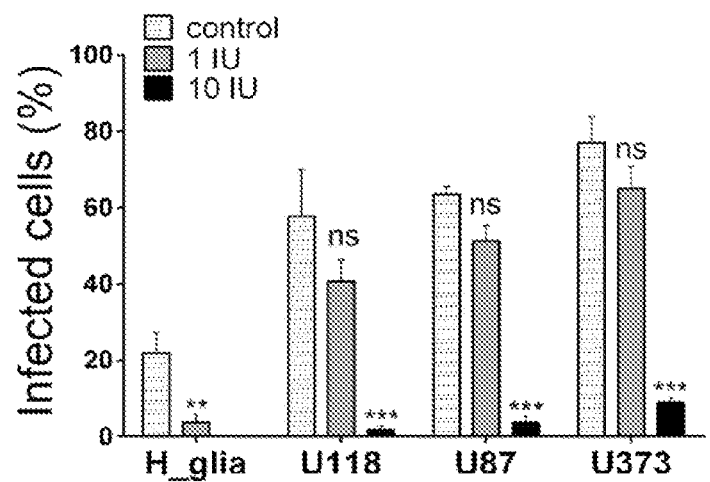
FIG. 5A is a bar graph showing the percentage of infected human glioma cells pretreated with a recombinant hybrid type-I interferon, IFN-α A/D, at different concentrations (0, 1 and 10 IU/ml) for 12 h prior to infection with VSVΔG-CHIKV at an MOI of 0.02. Values are reported as the mean+/−SEM; n=6. ns, not significant, *p<0.05, p<0.01, *p<0.001 vs. control; ANOVA with repeated measures.
Figure 5B:
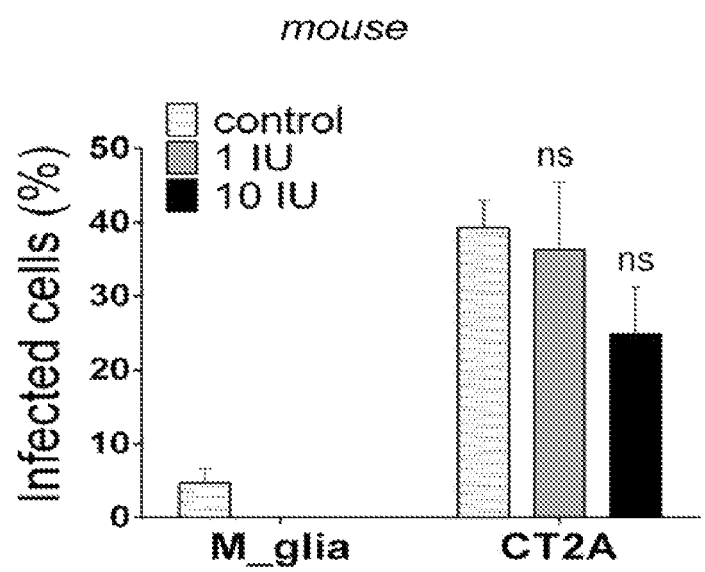
FIG. 5B is a bar graph showing the percentage of infected mouse CT-2A cells and primary mouse glia cells pretreated with a recombinant hybrid type-I interferon, IFN-α A/D, at different concentrations (0, 1 and 10 IU/ml) for 12 h prior to infection with VSVΔG-CHIKV at an MOI of 0.02. Values are reported as the mean+/−SEM; n=6. ns, not significant, *p<0.05, p<0.01, *p<0.001 vs. control; ANOVA with repeated measures.

As used herein, the term "effective amount" or "therapeutically effective amount" means a dosage sufficient to treat, inhibit, or alleviate one or more symptoms of a disease state being treated or to otherwise provide a desired pharmacologic and/or physiologic effect. The precise dosage will vary according to a variety of factors such as subject-dependent variables (e.g., age, immune system health, etc.), the disease, and the treatment being effected.

As used herein, the terms "neoplastic cells," "neoplasia," "tumor," "tumor cells," "cancer" and "cancer cells," (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign.

As used herein, an "immunogen" or "immunogenic amount" refers to the ability of a substance (antigen) to induce an immune response. An immune response is an alteration in the reactivity of an organisms' immune system in response to an antigen. In vertebrates this may involve antibody production, induction of cell-mediated immunity, complement activation or development of immunological tolerance.

As used herein, an "adjuvant" is a substance that increases the ability of an antigen to stimulate the immune system.

As used herein, "attenuated" refers to refers to procedures that weaken an agent of disease (a pathogen). An attenuated virus is a weakened, less vigorous virus. A vaccine against a viral disease can be made from an attenuated, less virulent strain of the virus, a virus capable of stimulating an immune response and creating immunity but not causing illness or less severe illness. Attenuation can be achieved by chemical treatment of the pathogen, through radiation, or by genetic modification, using methods known to those skilled in the art. Attenuation may result in decreased proliferation, attachment to host cells, or decreased production or strength of toxins.

As used herein, "subject," "individual," and "patient" refer to any individual who is the target of treatment using the compositions. The subject can be a vertebrate, for example, a mammal. Thus, the subject can be a human. The subjects can be symptomatic or asymptomatic. The term does not denote a particular age or sex. A subject can include a control subject or a test subject.

As used herein "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, "treatment" or "treating" means to administer a composition to a subject or a system with an undesired condition. The condition can include a disease. "Prevention" or "preventing" means to administer a composition to a subject or a system at risk for the condition. The condition can include a predisposition to a disease. The effect of the administration of the composition to the subject (either treating and/or preventing) can be, but is not limited to, the cessation of one or more symptoms of the condition, a reduction or prevention of one or more symptoms of the condition, a reduction in the severity of the condition, the complete ablation of the condition, a stabilization or delay of the development or progression of a particular event or characteristic, or minimization of the chances that a particular event or characteristic will occur. It is understood that where treat or prevent are used, unless specifically indicated otherwise, the use of the other word is also expressly disclosed.

II. Compositions

Chimeric viruses, particularly Chikungunya-vesicular stomatitis chimeric viruses, and compositions including an effective amount of a chimeric viruses are disclosed. The chimeric viruses are based on a VSV background where the VSV G protein is replaced with one or more heterologous virus glycoproteins. At least one of the glycoproteins is typically from a Togaviridae family virus, preferably an alphavirus, most preferably a Chikungunya virus.

Alphaviruses include, but are not limited to, Eastern Equine Encephalitis virus, Venezuelan Equine Encephalitis virus, Everglades virus, Mucambo virus, Pixuna virus, Semliki Forest virus, Middelburg virus, Chikungunya virus, Onyong-Nyong virus, Ross River virus, Barmash Forest virus, Getah virus, Sagiyama virus, Berbaru virus, Mayaro virus, Una virus, Sindbis virus, Aura virus, Whataroa virus, Babanki virus, Kyzylagach virus, Western Equine Encephalitis virus, Highlands J virus, Fort Morgan virus, Ndumu virus, and Buggy Creek virus (Strauss and Strauss, *Microbiological Reviews,* 58(3):491-562; Weaver and Frolov, *Togaviruses, p.* 1010-1024. In B. W. J. Mahy and V. Meulen (ed.), Virology, vol. 2. IRL Press, Salisbury, United Kingdom; and Garmashova, et al., *Journal of Virology,* 81 (5) 2472-2484 (2007).

In the most preferred embodiments, the VSV G protein is supplemented or replaced with a glycoprotein from a Chikungunya virus. Chikungunya virus (CHIKV) is a positive-sense single-strand RNA virus of the alphavirus genus and Togavirus family Prior to 2013 it was primarily found in Asia, Africa, and Europe; starting in 2013 the virus has been spread by mosquitoes through most of South America and parts of North America with non-human primates as a potential reservoir (Vignuzzi, et al., *Annu. Rev. Virol.,* 4:181-200 (2017); Vu, et al., *Clin. Lab Med.,* 37:371-382 (2017)). There is currently no approved vaccine available although a number of different experimental vaccines are being tested (Chattopadhyay, et al., *J. Virol.,* 87:395-402 (2013); Powers, *Clin. Microbiol. Rev.,* 31:e00104-16 (2018); Yang, et al., *Vaccine,* 35:4851-4858 (2017)). CHIKV has generally been associated with fever and joint pain, but can also cause headache, muscle ache, and rash (Hua, et al., *Curr. Rheumatol. Rep.,* 19:69 (2017); Amdekar, et al., *Virol. Immunol.,* 30:691-702 (2017)). The joint pain can persist for many months or longer. Chikungunya may bind to one of several surface proteins which are believed to include cholesterol transporters, prohibitin and others (Wichit, et al., *Sci. Rep.*, 7:3145 (2017); Wintachai, et al., *J. Med. Virol.*, 84:1757-1770 (2012)) and appears to be internalized in clathrin coated pits (Bernard, et al., *PLoS One*, 5:e11479 (2010); Schwartz, et al., *Nat. Rev. Microbiol.*, 8:491-500 (2010); Hoornweg, et al., *J. Virol.*, 90:4745-4756 (2016)).

A CHIKV-VSV chimeric virus containing a portion of the CHIKV structural polyprotein that includes the E3-E2-6K-E1 glycoprotein sequence substituted for the VSV glycoprotein (Chattopadhyay, et al, *J. Virol.*, 87:395-402 (2013)) was tested in the experiments below. CHIKV E2 underlies receptor binding, and E1 is responsible for the low pH membrane fusion activity after endocytotic entry (Voss, et al., *Nature*, 468:709-712 (2010); Solignat, et al., *Virology*, 393:183-197 (2009)). Together E2 and E1 constitute spike-like trimers on the virus surface. E3 is postulated to prevent premature virus fusion (Uchime, et al., *J. Virol.*, 87:10255-10262 (2013)), and 6K enhances virion release and titer (Taylor, et al., *J. Virol.*, 90:4150-4159 (2016)). VSV in which the normal glycoprotein gene G has been deleted and replaced by genes coding for the CHIKV envelope glycoprotein (VSVΔG-CHIKV) has been demonstrated as safe within the brain and, as tested in rodents, did not evoke neurological dysfunction or substantive negative consequences (van den Pol, et al., *J. Virol.*, 91:e02154-16 (2017)).

The chimeric virus can be further modified to express one or more therapeutic proteins, reporters, vaccine antigens, or targeting moieties. The chimeric viruses can be replication competent or incompetent. The chimeric viruses can be included in a pharmaceutical formulation alone or in combination with other therapeutic agents an effective amount of the virus to reduce one or more symptoms of cancer.

A. Chimeric G-Gene Substituted VSV

The viruses are typically chimeric alphavirus-VSV that are typically based on a VSV background strain, also referred to herein as a VSV backbone, wherein the G gene is substituted with an alphavirus glycoprotein. In preferred embodiments, the viruses are chimeric Chikungunya-VSV that are typically based on a VSV background strain, wherein the G gene is substituted with a Chikungunya glycoprotein. The chimeric virus can also include additional genetic changes (e.g., additions, deletions, substitutions) relative to the background VSV, and can have one or more additional transgenes.

VSV, a member of the Rhabdoviridae family, is enveloped and has a negative-strand 11.2-kb RNA genome that comprises five protein-encoding genes (N, P, M, G, and L) (Lyles, et al., Fields virology, 5$^{th}$ ed., Lippincott Williams & Wilkins, 1363-1408 (2007)). It is a nonhuman pathogen which can cause mild disease in livestock. Infection in humans is rare and usually asymptomatic, with sporadic cases of mild flu-like symptoms. VSV has a short replication cycle, which starts with attachment of the viral glycoprotein spikes (G) to an unknown but ubiquitous cell membrane receptor. Nonspecific electrostatic interactions have also been proposed to facilitate viral binding (Lyles, et al., Fields virology, 5$^{th}$ ed., Lippincott Williams & Wilkins, 1363-1408 (2007)). Upon internalization by clathrin-dependent endocytosis, the virus-containing endosome acidifies, triggering fusion of the viral membrane with the endosomal membrane. This leads to release of the viral nucleocapsid (N) and viral RNA polymerase complex (P and L) into the cytosol.

The viral polymerase initiates gene transcription at the 3' end of the non-segmented genome, starting with expression of the first VSV gene (N). This is followed by sequential gene transcription, creating a gradient, with upstream genes expressed more strongly than downstream genes. Newly produced VSV glycoproteins are incorporated into the cellular membrane with a large extracellular domain, a 20 amino acid trans-membrane domain, and a cytoplasmic tail consisting of 29 amino acids. Trimers of G protein accumulate in plasma membrane microdomains, several of which congregate to form viral budding sites at the membrane (Lyles, et al., Fields virology, 5$^{th}$ ed., Lippincott Williams & Wilkins, 1363-1408 (2007)). Most cells activate antiviral defense cascades upon viral entry, transcription, and replication, which in turn are counteracted by VSV matrix protein (M). VSV M protein's multitude of functions include virus assembly by linking the nucleocapsid with the envelope membrane, induction of cytopathic effects and apoptosis, inhibition of cellular gene transcription, and blocking of host cell nucleocytoplasmic RNA transfer, which includes blocking of antiviral cellular responses (Ahmed, et al., *Virology*, 237:378-388 (1997)).

Certain native, engineered, and recombinant VSV strains have been shown to target several tumor types, including gliomas, and give a strong oncolytic action, both in vitro and in vivo (Paglino and van den Pol, 2011) (Wollmann, et al, 2005; 2007; 2010; Ozduman et al, 2008). However, there remains a need for improved recombinant VSVs that are both efficacious for treating cancer and exhibit low pathogenicity to healthy host cells. This is particularly important in the brain where mature neurons do not replicate, and once lost, are normally not replaced. Although some evidence indicates that attenuated VSVs show reduced neurotoxicity, CNS complications have been difficult to eliminate completely (Obuchi et al, 2003; van den Pol et al, 2002; 2009).

It has been discovered that recombinant, chimeric Chikungunya-VSV where the G gene is substituted with a gene encoding a Chikungunya glycoprotein protein have superior oncolytic potential in targeting and destroying cancer cells with little pathogenicity to healthy host cells. Chikungunya VSV chimeric viruses, pharmaceutical compositions including Chikungunya VSV chimeric viruses, and methods of use thereof for treating cancer are provided. As discussed in more detail below, preferably, the virus targets and kills tumor cells, shows little or no infection of normal cells, and extended survival of tumor-bearing mice.

1. VSV Background Strain

Useful VSV background strains can be viruses that are known in the art, or they can be mutants or variants of known viruses. Any suitable VSV strain or serotype may be used, including, but not limited to, VSV Indiana, VSV New Jersey, VSV Alagoas, (formerly Indiana 3), VSV Cocal (formerly Indiana 2), VSV Chandipura, VSV Isfahan, VSV San Juan, VSV Orsay, or VSV Glasgow. The VSV background can be a naturally occurring virus, or a virus modified, for example, to increase or decrease the virulence of the virus, and/or increase the specificity or infectivity of the virus compared to the parental strain or serotype. The virus can be a recombinant virus that includes genes from two or more strains or serotypes. For example, the VSV background strain can be a recombinant VSV with all five genes of the Indiana serotype of VSV. In other exemplary embodiments, the N, P, M, and L genes originates from the San Juan strain, and the G gene from the Orsay strain.

It may be desirable to further reduce the neurovirulence of the viruses, particularly the virulence of the therapeutic virus, by using an attenuated virus. A number of suitable VSV mutants have been described, see for example (Clarke, et al., *J. Virol.*, 81:2056-64 (2007), Flanagan, et al., *J. Virol.*, 77:5740-5748 (2003), Johnson, et al., *Virology*, 360:36-49 (2007), Simon, et al., *J. Virol.*, 81:2078-82 (2007), Stojdl, et al., *Cancer Cell*, 4:263-275 (2003)), Wollmann, et al., *J. Virol*, 84(3):1563-73 (2010) (epub 2010), WO 2010/080909, U.S. Published Application No. 2007/0218078, and U.S. Published Application No 2009/0175906.

Recombinant VSVs derived from DNA plasmids also typically show weakened virulence (Rose, et al., Cell, 106: 539-549 (2001)). Attenuation of VSV virulence can also be accomplished by one or more nucleotide sequence alterations that result in substitution, deletion, or insertion of one or more amino acids of the polypeptide it encodes.

In some embodiments, the VSV background strain is a VSV modified to attenuate virus growth or pathogenicity or to reduce the ability to make infectious progeny viruses. VSV strains and methods of making such VSV strains are known in the art, and described in, for example, U.S. Published Application No. 2012/0171246.

For example, one strategy is to attenuate viral pathogenicity by reducing the ability of the virus to suppress host innate immune responses without compromising the yield of infectious progeny. This can be accomplished by mutating the M protein as described, for example, in Ahmed, *J. Virol.*, 82(18):9273-9277 (2008). The M protein is a multifunctional protein that is involved in the shutoff of host transcription, nuclear cytoplasmic transport, and translation during virus infection (Lyles, *Microbiol. Mol. Biol. Rev.* 64:709-724 (2000)). Mutation and/or deletion of one or more amino acids from the M protein, for example MΔ51, or M51A mutants can result in viral protein that is defective at inhibiting host gene expression. It may also be desirable to switch or combine various substitutions, deletions, and insertions to further modify the phenotype of the virus. For example, the recombinant VSV background can have a deletion or mutation in the M protein.

Altering the relative position of genes can also be used to attenuate virus (Clarke, et al., *J. Virol.*, 81:2056-2064, (2007), Cooper, et al., *J. Virol.*, 82:207-219 (2008), Flanagan, et al., *J. Virol.*, 75:6107-6114 (2001)). VSV is highly immunogenic, and a substantial B and T cell response from the adaptive immune system will ultimately limit VSV infection, which will halt long-lasting viral infections. A virus that shows enhanced selectivity, and a faster rate of infection, will have a greater likelihood of eliminating cancer cells before the virus is eliminated by the immune system. However, the use of VSV against cancer cells does not have to be restricted to a single application. By molecular substitution of the G-protein for enhancing immune responses against foreign genes expressed by VSV, one could switch the original G protein of the virus (e.g., Indiana VSV) with the G protein from another strain or serotype (e.g., VSV New Jersey or Chandipura), allowing a slightly different antigen presentation, and reducing the initial response of the adaptive immune system to second or third oncolytic inoculations with VSV.

Therefore, the chimeric viruses can have a VSV genome that is rearranged compared to wildtype VSV. For example, shifting the L-gene to the sixth position, by rearrangement or insertion of an additional gene upstream, can result in attenuated L-protein synthesis and a slight reduction in replication (Dalton and Rose, *Virology*, 279(2):414-21 (2001)), an advantage when considering treatment of the brain.

Repeat passaging of virulent strains under evolutionary pressure can also be used to generate attenuated virus, increase specificity of the virus for a particular target cell type, and/or increase the oncolytic potential of the virus. For example, VSV-rp30 ("30 times repeated passaging") is a wild-type-based VSV with an enhanced oncolytic profile (Wollmann, et al., *J. Virol.* 79:6005-6022 (2005)). As described in WO 2010/080909, VSV-rp30 has a preference for glioblastoma over control cells and an increased cytolytic activity on brain tumor cells. Accordingly, in some embodiments, the VSV background of the chimeric viruses is one that has been modified to attenuate the virus, increase specificity of the virus for a particular target cells, and/or increase the oncolytic potential of the virus relative to a wildtype or starting stain.

2. Chikungunya Glycoproteins

The chimeric VSV have a heterologous glycoprotein. Typically, the chimeric VSV are viruses that lack the G protein of VSV. The chimeric VSV have a glycoprotein (e.g., G protein or GP protein) from a distinct, non-VSV. The substituted glycoprotein typically comes from an alphavirus.

Most typically, the G protein of VSV is supplemented or substituted with a glycoprotein from a Chikungunya virus. In a preferred embodiment, the chimeric virus includes one or more CHIKV structural proteins (C, E3, E2, 6K and E1). In a particularly preferred embodiment, the chimeric virus includes E3, E2, 6K and E1. Chimeric virus in incorporating the entire CHIKV E3-E2-6K-E1 in place of VSV G (VSVΔG-CHIKV) (FIG. 1A) is in Chattopadhyay, et al., *J. Virol.*, 87:395-402 (2013).

CHIKV structural protein and nucleic acid sequences are known in the art. See, e.g., UniProt accession no. Q8JUX5 and NCBI reference sequence no. NP_690589.2, each of which is incorporated by reference in its entirety.

For example, Q8JUX5 provides the amino acid sequence MEFIPTQTFYNRRYQPRPWTPRPTIQVIRPRPRPORO-AGOLAQLISAVNKL
TMRAVPQQKPRRNRKNKKOKOKQQAPON-NTNQKKOPPKKKPAQKKKKPGRR ERMCMKIEND-CIFEVKHEGKVTGYACLVGDKVMKPAHVKGTID-NADLAKLA
FKRSSKYDLECAQIPVHMKSDASKFTHEKPEGYYN-WHHGAVQYSGGRFTIP TGAGKPGDSGRP IFDNKGRVVAIVLGGANEGARTALSVVTWNKDIVT-KITP EGAEEWSLAIPVMCL-LANTTFPCSQPPCIPCCYEKEPEETLRMLEDNVMRP GYYQLLQASLTCSPHRQRRSTKDNENVYKATRPY-LAHCPDCGEGHSCHSPV ALER-IRNEATDGTLKIQVSLQIGIGTDDSHDWTKLRYMDN-HIPADAGRAGL
FVRTSAPCTITGTMGHFILARCPKGETLTVGFTDSRK-ISHSCTHPFHHDPP VIGREKFHSRPQHGKELPCSTY-VOSNAATAEEIEVHMPPDTPDRILLSQQS
GNVKITVNGRTVRYKCNCGGSNEG-LITTDKVINNCKVDOCHAAVTNHKKWQ YNSPLVPR-NAELGDRKGKIHIPF-
PLANVTCMVPKARNPTVTYGKNQVIMLL
YPDHPTLLSYRSMGEEPNYQEEWVTHKKEV-VLTVPTEGLEVTWGNNEPYKY WPQLSANG-TAHGHPHEIILYYYELYPTMTVVVVSVASFILLSMVG-MAVGMC
MCARRRCITPYELTPGATVPFLLSLICCIRTA-KAATYQEAAVYLWNEQQPL FWLQALIPLAAL-IVLCNCLRLLPCCCKTLAFLAVMSI-
GAHTVSAYEHVTVI
PNTVGVPYKTLVNRPGYSPMVLEMELLSVT-LEPTLSLDYITCEYKTVIPSP YVKCCG-TAECKDKNLPDYSCKVFTGVYPFMWGGAYCFC-DAENTOLSEAHVE
KSESCKTEFASAYRAHTASASAKLRVLYQGN-NITVTAYANGDHAVTVKDAK FIVGPMSSAW-TPFDNKIVVYKGDVYNMDYPPFGAGRPG-OFGDIQSRTPESK DVYANTOLVLORPAAGTVHVPYSQAP SGFKYWLKERGASLOHTAPFGCQIA TNPVRAMNCAVGNMPISIDIPDAAFTRVVDAPSLTDMSCEVPACTASSDFG GVAIIKYAVSKKGKCAVHSMTNAVTIREAEIEVEGNSQLQISFSTALASAE FRVQVCSTQVHCAAECHPPKDHIVNYPASHTTIGVODISATAMSWVQKITG GVGLVVAVAALILIVVLCVSFSRA (SEQ ID NO:1, UniProtKB-Q8JUX5 (POLS_CHIKS, Chikungunya virus (strain S27-African prototype) (CHIKV), Structural polyprotein).

NP_690589.2 provides the amino acid sequence MEFIPTQTFYNRRYQPRPWTPRPTIQVIRPRPRPOROAGOLAQLISAVNKL TMRAVPQQKPRKNRKNKKOKOKQQAPONNTNQKKOPPKKKPAQKKKKPGRR ERMCMKIENDCIFEVKHEGKVTGYACLVGDKVMKPAHVKGTIDNADLAKLA FKRSSKYDLECAQIPVHMKSDASKFTHEKPEGYYNWHHGAVQYSGGRFTIP TGAGKPGDSGRPIFDNKGRVVAIVLGGANEGARTALSVVTWNKDIVTKITP EGAEEWSLAIPVMCLLANTTFPCSQPPCIPCCYEKEPEETLRMLEDNVMRP GYYQLLQASLTCSPHRQRRSTKDNFNVYKATRPYLAHCPDCGEGHSCHSPV ALERIRNEATDGTLKIQVSLQIGIGTDDSHDWTKLRYMDNHIPADAGRAGL FVRTSAPCTITGTMGHFILARCPKGETLTVGFTDSRKISHSCTHPFHHDPP VIGREKFHSRPQHGKELPCSTYVQSNAATAEEIEVHMPPDTPDRILLSQQS GNVKITVNSQTVRYKCNCGGSNEGLITTDKVINNCKVDQCHAAVTNHKKWQ YNSPLVPRNAELGDRKGKIHIPFPLANVTCMVPKARNPTVTYGKNQVIMLL YPDHPTLLSYRSMGEEPNYQEEWVTHKKEVVLTVPTEGLEVTWGNNEPYKY WPQLSANGTAHGHPHEIILYYYELYPTMTVVVVSVASFILLSMVGMAVGMC MCARRRCITPYELTPGATVPFLLSLICCIRTAKAATYQEAAVYLWNEQOPL FWLQALIPLAALIVLCNCLRLLPCCCKTLAFLAVMSIGAHTVSAYEHVTVI PNTVGVPYKTLVNRPGYSPMVLEMELLSVTLEPTLSLDYITCEYKTVIPSP YVKCCGTAECKDKNLPDYSCKVFTGVYPFMWGGAYCFCDAENTOLSEAHVE KSESCKTEFASAYRAHTASASAKLRVLYOGNNITVTAYANGDHAVTVKDAK FIVGPMSSAWTPFDNKIVVYKGDVYNMDYPPFGAGRPGOFGDIQSRTPESK DVYANTOLVLORPAAGTVHVPYSOAPSGFKYWLKERGASLOHTAPFGCQIA TNPVRAMNCAVGNMPISIDIPDAAFTRVVDAPSLTDMSCEVPACTASSDFG GVAIIKYAVSKKGKCAVHSMTNAVTIREAEIEVEGNSQLQISFSTALASAE FRVQVCSTOVHCAAECHPPKDHIVNYPASHTTLGVODISATAMSWVOKITG GVGLVVAVAALILIVVLCVSFSRH (SEQ ID NO:2, NCBI Reference Sequence: NP_690589.2 (structural polyprotein [Chikungunya virus]).

SEQ ID NOS: 1 and 2. differ at position 63 (R→K), and positions 519-43 520 (GR→SQ).

SEQ ID NOS:1 and 2 provide CHIKV structural polyproteins including sequences for C, E3, E2, 6K, and E1 proteins. Specific enzymatic cleavages in vivo yield mature proteins. Capsid protein is auto-cleaved during polyprotein translation, unmasking a signal peptide at the N-terminus of the precursor of E3/E2. The remaining polyprotein is then targeted to the host endoplasmic reticulum, where host signal peptidase cleaves it into pE2, 6K and E1 proteins. pE2 is further processed to mature E3 and E2 by host furin in trans-Golgi vesicle.

The sequences of the C, E3, E2, 6K, and E1 proteins within the CHIKV structural protein are also known in the art. For example, UniProtKB-Q8JUX5 annotates SEQ ID NOS:1 and 2 as follows:

TABLE 1

Annotation of CHIV Structural Polyprotein.

| Position(s) | Description | Length | SEQ ID NO. |
|---|---|---|---|
| 1-261 | Capsid protein | 261 | 3, 4 |
| 262-748 | Precursor of protein E3/E2 | 487 | |
| 262-325 | Assembly protein E3 | 64 | 5 |
| 326-748 | Spike glycoprotein E2 | 423 | 6, 7 |
| 749-809 | 6K protein | 61 | 8 |
| 810-1248 | Spike glycoprotein E1 | 439 | 9 |
| 262-1248 | E3-E2-6K-E1 | 987 | 10, 11 |

As introduced above, the chimeric virus typically includes one or more CHIKV structural proteins (C, E3, E2, 6K and E1). Thus, in some embodiments, the glycoprotein of the chimeric virus is, or includes, one or more of SEQ ID NOS:1-11, or one or more fragments or variants thereof, including mature or processed fragments thereof and their variants. Variants of SEQ ID NOS:1-11 can have, for example, at least 50%, 60%, 70%, 75%, 80%, 85%, 90%, 95%, 96%, 97%, 98%, 99%, or more sequence identity to any one of SEQ ID NOS:1-11.

In some embodiments, the glycoprotein includes one or more of SEQ ID NOS:5, 6, 8 and 9, or functional fragments, mature or processed polypeptides, or variants thereof having, for example, at least 50%, 60%, 70%, 75%, 80%, 85%, 90%, 95%, 96%, 97%, 98%, 99%, or more sequence identity to any one of SEQ ID NOS:5, 6, 8 and 9.

In some embodiments, the glycoprotein includes one or more of SEQ ID NOS:5, 7, 8 and 9, or functional fragments, mature or processed polypeptides, or variants thereof having, for example, at least 50%, 60%, 70%, 75%, 80%, 85%, 90%, 95%, 96%, 97%, 98%, 99%, or more sequence identity to any one of SEQ ID NOS:5, 7, 8 and 9.

In some embodiments, the chimeric virus includes E3, E2, 6K and E1. Thus, in some embodiments, the glycoprotein includes SEQ ID NOS:10 or 11, or functional fragments, mature or processed polypeptides, or variants thereof having, for example, at least 50%, 60%, 70%, 75%, 80%, 85%, 90%, 95%, 96%, 97%, 98%, 99%, or more sequence identity to any one of SEQ ID NOS:10 or 11.

Nucleic acid sequences encoding the disclosed proteins and viruses (including VSV and non-VSV (e.g., CHIKV) protein and viruses), and nucleic acids including the nucleic acid sequences, are also provided. For example, nucleic acid sequences encoding heterologous proteins such as CHIKV structural polyprotein, and proteins thereof including capsid, E3, E2, 6K and E1, and mature functional fragments, mature or processed polypeptides, and variants thereof, and the reverse complements thereof are also provided. Thus, for example, nucleic acid sequences encoding SEQ ID NOS:1-11 and variants thereof with least 50%, 60%, 70%, 75%, 80%, 85%, 90%, 95%, 96%, 97%, 98%, 99%, or more sequence identity to any one of SEQ ID NOS:1-11 and the reverse complements thereof are provided.

The nucleic acid sequences can be part of single stranded or double stranded nucleic acids that can be, for example, DNA or RNA. In some embodiments, the nucleic acids are part of a viral genome, a viral vector, or a plasmid or other construct encoding part or all of a viral genome. Thus, the negative sense, single-stranded RNA (e.g., chimeric VSV genomic sequences) encoding the proteins and polypeptides, including heterologous glycoprotein; DNA encoding the negative sense, single-stranded RNA (e.g., plasmid and other constructs encoding chimeric VSV genomic sequences) encoding the proteins and polypeptides, including heterologous glycoprotein; and mRNA encoding the proteins and polypeptides, including heterologous glycoprotein are expressly provide.

3. Additional Transgenes

Viruses can be modified to express one or more additional transgenes, separately or as a part of other expressed proteins. The viral genome of VSV has the capacity to accommodate additional genetic material. At least two additional transcription units, totaling 4.5 kb, can be added to the genome, and methods for doing so are known in the art. The added genes are stably maintained in the genome upon repeated passage (Schnell, et al., *EMBO Journal*, 17:1289-1296 (1998); Schnell, et al., *PNAS*, 93: 11359-11365 (1996); Schnell, et al., *Journal of Virology*, 70:2318-2323 (1996); Kahn, et al., *Virology*, 254, 81-91 (1999)).

In some embodiments the viruses are modified to include a gene encoding a therapeutic protein, an antigen, a detectable marker or reporter, a targeting moiety, or a combination thereof. In some embodiments, the gene is placed in the first gene position in the VSV background. Given the nature of VSV protein expression, genes in the first position generate the highest expression of any gene in the virus, with a 3' to 5' decrease in gene expression. The chimeric VSV can also be constructed to contain two different and independent genes placed in the first and second gene position of VSV. For example, van den Pol and Davis, et al., *J. Virol.*, 87(2):1019-1034 (2013), describes the generation of a highly attenuated VSV by adding two (reporter) genes to the 3' end of the VSV genome, thereby shifting the NPMGL genes from positions 1 to 5 to positions 3 to 7. This strategy can be used to allow strong expression of genes coding for any combination of two heterologous proteins, for example two therapeutic proteins, a therapeutic protein and reporter, or an immunogenic protein and a reporter that could be useful to track the virus in a clinical situation.

a. Therapeutic Proteins and Reporters

The chimeric viruses, including Chikungunya VSV chimeric viruses, can be engineered to include one or more additional genes that encode a therapeutic protein or a reporter. Suitable therapeutic proteins, such as cytokines or chemokines, are known in the art, and can be selected depending on the use or disease to be treated. Preferred cytokines include, but are not limited to, granulocyte macrophage colony stimulating factor (GM-CSF), tumor necrosis factor alpha (TNFα), tumor necrosis factor beta (TNFβ), macrophage colony stimulating factor (M-CSF), interleukin-1 (IL-1), interleukin-2 (IL-2), interleukin-4 (IL-4), interleukin-5 (IL-5), interleukin-6 (IL-6), interleukin-10 (IL-10), interleukin-12 (IL-12), interleukin-15 (IL-15), interleukin-21 (IL-21), interferon alpha (IFNα), interferon beta (IFNβ), interferon gamma (IFNγ), and IGIF, and variants and fragments thereof.

Suitable chemokines include, but are not limited to, an alpha-chemokine or a beta-chemokine, including, but not limited to, a C5a, interleukin-8 (IL-8), monocyte chemotactic protein 1 alpha (MIP1α), monocyte chemotactic protein 1 beta (MIP1β), monocyte chemo-attractant protein 1 (MCP-1), monocyte chemo-attractant protein 3 (MCP-3), platelet activating factor (PAFR), N-formyl-methionyl-leucyl-[$^3$H]phenylalanine (FMLPR), leukotriene $B_4$, gastrin releasing peptide (GRP), RANTES, eotaxin, lymphotactin, IP10, I-309, ENA78, GCP-2, NAP-2 and MGSA/gro, and variants and fragments thereof.

Particularly preferred genes include those that encode proteins that up-regulate an immune attack on infected tumors such as IL-28, IL-2, FLT3L, and GM-CSF (Ali, et al., *Cancer Res*, 65:7194-7204 (2005); Barzon, et al., *Methods Mol. Biol.*, 542:529-549 (2009); Wongthida, et al., *Hum. Gene Ther.*, 22:1343-53 (2011). Other therapeutic proteins that have been successfully engineered into VSV or other viruses include IL2, IL-4, IL-7, IL-12, and TRAIL (Jinush, et al., *Cancer Science*, 100, 1389-1396. (2009)). The virus can also be engineered to include one or more genes encoding a reporter. The reporter can serve as a measure or monitor of in vivo viral activity. Exemplary reporters are known in the art and include, but are not limited to, carcinoembryonic antigen, secreted alkaline phosphatase, and the beta subunit of chorionic gonadotropin. These reporters are released by infected cells into the blood, and can be measured peripherally to determine viral activity, including viral activity in the brain (Phuong, et al., *Cancer Res.*, 63:2462-2469 (2003); Peng, et al., *Nat. Med.*, 8:527-531 (2002); Shashkova, et al., *Cancer Gene Ther.*, 15:61-72 (2008); Hiramatsu, et al., *Cancer Science*, 100, 1389-1396 (2005)).

In some embodiments, the virus's genome is modified to encode a detectable marker or reporter, preferably in the first position. The detectable marker allows the user to detect and monitor the location and efficacy of the virus in vivo and in resected tissue ex vivo without the need for antibodies. Suitable markers are known in the art and include, but are not limited to, LacZ, GFP (or eGFP), and luciferase.

There have been reports of humoral immune response to eGFP and rejection of eGFP transduced cells following subretinal administration of AAV2 or lentivirus expressing eGFP in animals (Bainbridge, et al., *Gene Ther.*, 10(16): 1336-44 (2003), and Doi, K., *J. Virol*, 78(20): 11327-33 (2004)). Thus, the safety and in vivo persistence of a virus including a detectable marker (e.g., one expressing eGFP) may be different than that of a virus without the marker, however, these differences can be assessed by one of skill in the art using methods known in the art and the methods described in the Examples. In the particular case of VSV, adding a gene added to the first position typically attenuates the virulence of VSV (Wollmann, et al., *J. Virol.*, 84(3): 1563-73 (2010)). Therefore, in some embodiments, chimeric VSV that include a marker such as GFP in the first position may have an improved safety profile compared viruses without it.

b. Viruses Engineered to Deliver Vaccine Antigens

The virus can be a vaccine vector that serves as an immunogen for eliciting an immune response against a disease. This can be accomplished by cloning an antigen of an unrelated disease into the chimeric VSV. VSVs expressing foreign viral glycoproteins have shown promise as a vaccine vectors (Roberts, et al., *J. Virol.* 73:3723-3732 (1999), Rose, et al., *Cell*, 106:539-549 (2001), Jones, et al., *Nat. Med.* 11:786-790 (2005)). Additionally, recombinant VSVs are able to accommodate large inserts and multiple genes in their genomes. This ability to incorporate large gene inserts in replication-competent viruses offers advantages over other RNA or DNA virus vectors, such as those based on alphaviruses, REO virus, poliovirus, and parvovirus.

VSVs can be engineered to incorporate one or more nucleic acid sequences encoding one or more non-native or heterologous immunogenic antigens. One or more native VSV genes may be truncated or deleted to create additional space for the sequence encoding the immunogenic antigen. When expressed by the VSV administered to a patient in need thereof, the immunogenic antigen produces prophylactic or therapeutic immunity against a disease or disorder Immunogenic antigens can be expressed as a fusion protein with other polypeptides including, but not limited to, native VSV polypeptides, or as a non-fusion protein. By way of non-limiting examples, the antigen can be a protein or polypeptide derived from a virus, bacterium, parasite, plant, protozoan, fungus, tissue or transformed cell such as a cancer or leukemic cell. Antigens may be expressed as single antigens or may be provided in combination.

Because the substitution of the Chikungunya glycoprotein for the VSV glycoprotein generates a chimeric virus that is far safer than VSVs that contain the VSV glycoprotein, yet still retains the broad spectrum of cells to which it can bind, the chimeric virus can serve as a vaccination platform for a wide variety of microbial pathogens, including, but not limited to, HIV, influenza, polio, measles, mumps, chicken pox, hendra, and others. In some embodiments CHIKV-VSV chimeric virus is safe even in the brains of SCID mice lacking the normal T and B cell systemic immunity. Therefore the chimeric Chikungunya-VSV might be useful in vaccinating people with depressed immune systems, for instance those with AIDS or those with genetically compromised immune systems, or patients with attenuated immunity related to ongoing cancer. The target of the vaccine could either be a type of cancer cell as a cancer treatment. Alternately, the target could be any of a large number of microbial pathogens.

c. Targeting Domains

Viruses can be engineered to include one or more additional genes that target the virus to cells of interest, see for example U.S. Pat. No. 7,429,481. In preferred embodiments, expression of the gene results in expression of a ligand on the surface of the virus containing one or more domains that bind to antigens, ligands or receptors that are specific to tumor cells, or are up-regulated in tumor cells compared to normal tissue. Appropriate targeting ligands will depend on the target cell or cancer of interest and will be known to those skilled in the art. For example, glioma stem cells are reported to express CD133 and nestin. Accordingly, in some embodiments, the viruses are engineered to express a targeting moiety that bind to CD133 or nestin.

B. Pharmaceutical Compositions

Immunizing and therapeutic viruses are typically administered to a patient in need thereof in a pharmaceutical composition. Pharmaceutical compositions containing virus may be for systemic or local administration, such as intratumoral. Dosage forms for administration by parenteral (intramuscular (IM), intraperitoneal (IP), intravenous (IV), intra-arterial, intrathecal or subcutaneous injection (SC)), or transmucosal (nasal, vaginal, pulmonary, or rectal) routes of administration can be formulated. In some embodiments, a therapeutic virus is delivered by local injection, for example intracranial injection preferably at or near the tumor site. In a particular embodiment a therapeutic virus is injected directly into the tumor. The compositions can be formulated for and delivered via catheter into the tumor resection cavity through convection-enhanced delivery (CED). In some embodiments an immunizing virus is delivered peripherally, intranasally or by intramuscular injection.

The virus can also be used as an immunizing virus. The immunizing virus can be the same as a therapeutic virus but administered prior to a therapeutic administration so that the subject's immune system is primed to eliminate the virus following the therapeutic administration. Alternatively, the immunizing virus can be modified to carry a disease antigen and used as part of a vaccine protocol Immunizing viruses can be delivered peripherally, for example, by the intranasal route or by intramuscular injection.

1. Effective Amounts

As generally used herein, an "effective amount" is that amount which is able to induce a desired result in a treated subject. The desired results will depend on the disease or condition to be treated. The precise dosage will vary according to a variety of factors such as subject-dependent variables (e.g., age, immune system health, etc.), the disease, and the treatment being effected. For example, an effective amount of immunizing virus generally results in production of antibody and/or activated T cells against an antigen, or that kill or limit proliferation of or infection by a pathogen. An effective amount of the immunizing virus can be an amount sufficient to reduce neurovirulence of the therapeutic virus compared to administration of the therapeutic virus without first administering the immunizing virus.

Therapeutically effective amounts of the therapeutic viruses used in the treatment of cancer will generally kill tumor cells or inhibit proliferation or metastasis of the tumor cells. Symptoms of cancer may be physical, such as tumor burden, or biological such as proliferation of cancer cells. The actual effective amounts of virus can vary according to factors including the specific virus administered, the particular composition formulated, the mode of administration, and the age, weight, condition of the subject being treated, as well as the route of administration and the disease or disorder.

An effective amount of the virus can be compared to a control. Suitable controls are known in the art. A typical control is a comparison of a condition or symptom of a subject prior to and after administration of the virus. The condition or symptom can be a biochemical, molecular, physiological, or pathological readout. In another embodiment, the control is a matched subject that is administered a different therapeutic agent. Accordingly, the compositions disclosed here can be compared to other art recognized treatments for the disease or condition to be treated.

For example, the virus can be administered in an amount effective to infect and kill cancer cells, improve survival of a subject with cancer, or a combination thereof. In a particular embodiment, the cancer is glioblastoma. In another particular embodiment, the caner is melanoma.

One of the advantages of the viruses is that they show little or no toxicity to normal or healthy cells (e.g., non-cancerous cells) even in immunocompromised animals. Therefore, in some embodiments the effective amount of virus causes little or no destruction of non-cancerous cells. The level of pathogenicity to normal cells can be compared to the level of pathogenicity of other VSV oncolytic viruses that do not have G gene replaced with a heterologous G gene. Such viruses are known in the art and include, for example, VSV-1'GFP, VSV-rp30, or VSV-ΔM51, and others discussed in the examples below.

One important index of oncolytic potential is the ratio of viral replication in normal/control cells versus tumor or cancer cells. These ratios serve as an important index of the relative levels of viral replication in normal and tumor cells. A large ratio indicates greater replication in cancer cells than in control cells. In preferred embodiments, the ratio of replication of normal cells:target cells is greater than about 1:100, preferably greater than about 1:250, more preferable greater than about 1:500, most preferably greater than about 1:1000. In some embodiments, the oncolytic potential of the viruses is larger than the oncolytic potential of other VSV oncolytic viruses that do not have G gene replaced with a heterologous G gene, for example, VSV-1'GFP, VSV-rp30, or VSV-ΔM51, or compared VSV chimeras wherein the G protein is not from CHIKV.

2. Dosages

Appropriate dosages can be determined by a person skilled in the art, considering the therapeutic context, age, and general health of the recipient. The selected dosage depends upon the desired therapeutic effect, on the route of administration, and on the duration of the treatment desired. Active virus can also be measured in terms of plaque-forming units (PFU). A plaque-forming unit can be defined as areas of cell lysis (CPE) in monolayer cell culture, under overlay conditions, initiated by infection with a single virus particle. Generally dosage levels of virus between $10^2$ and $10^{12}$ PFU are administered to humans. Virus is typically administered in a liquid suspension, in a volume ranging between 10 µl and 100 ml depending on the route of administration. Generally, dosage and volume will be lower for intratumoral injection as compared to systemic administration or infusion. The dose may be administered once or multiple times. When administered locally, virus can be administered to humans at dosage levels between $10^2$ and $10^8$ PFU. Virus can be administered in a liquid suspension, in a low volume. For example, the volume for local administration can range from about 20 nl to about 200 µl. Multiple doses can be administered. In some embodiment, multiple injections are used to achieve a single dose. Systemic or regional administration via subcutaneous, intramuscular, intra-organ, or intravenous administration can have higher volumes, for example, 10 to 100 ml.

3. Formulations

The term "pharmaceutically acceptable" means a non-toxic material that does not interfere with the effectiveness of the biological activity of the active ingredients. The term "pharmaceutically-acceptable carrier" means one or more compatible solid or liquid fillers, diluents or encapsulating substances which are suitable for administration to a human or other vertebrate animal. The term "carrier" refers to an organic or inorganic ingredient, natural or synthetic, with which the active ingredient is combined to facilitate the application.

Pharmaceutical compositions may be formulated in a conventional manner using one or more physiologically acceptable carriers including excipients and auxiliaries which facilitate processing of the active compounds into preparations which can be used pharmaceutically. The compositions may be administered in combination with one or more physiologically or pharmaceutically acceptable carriers, thickening agents, co-solvents, adhesives, antioxidants, buffers, viscosity and absorption enhancing agents and agents capable of adjusting osmolarity of the formulation. Proper formulation is dependent upon the route of administration chosen. If desired, the compositions may also contain minor amounts of nontoxic auxiliary substances such as wetting or emulsifying agents, dyes, pH buffering agents, or preservatives. The formulations should not include membrane disrupting agents which could kill or inactivate the virus.

a. Formulations for Local or Parenteral Administration

In a preferred embodiment, compositions including oncolytic viruses disclosed herein, are administered in an aqueous solution, by parenteral injection. Injection includes, but it not limited to, local, intratumoral, intravenous, intraperitoneal, intramuscular, or subcutaneous injection. The formulation may also be in the form of a suspension or emulsion. In general, pharmaceutical compositions are provided including effective amounts of virus, and optionally include pharmaceutically acceptable diluents, preservatives, solubilizers, emulsifiers, adjuvants and/or carriers. Such compositions include diluents such as sterile water, buffered saline of various buffer content (e.g., Tris-HCl, acetate, phosphate), pH and ionic strength; and optionally, additives such as anti-oxidants (e.g., ascorbic acid, sodium metabisulfite), and preservatives and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. A preferred solution is phosphate buffered saline or sterile saline.

b. Formulations for Mucosal Administration

In some embodiments, the compositions are formulated for mucosal administration, such as through nasal, pulmonary, or buccal delivery.

Mucosal formulations may include one or more agents for enhancing delivery through the nasal mucosa. Agents for enhancing mucosal delivery are known in the art, see, for example, U.S. Patent Application No. 2009/0252672 to Eddington, and U.S. Patent Application No. 2009/0047234 to Touitou. Acceptable agents include, but are not limited to, chelators of calcium (EDTA), inhibitors of nasal enzymes (boro-leucin, aprotinin), inhibitors of muco-ciliar clearance (preservatives), solubilizers of nasal membrane (cyclodextrin, fatty acids, surfactants) and formation of micelles (surfactants such as bile acids, Laureth 9 and taurodehydrofusidate (STDHF)). Compositions may include one or more absorption enhancers, including surfactants, fatty acids, and chitosan derivatives, which can enhance delivery by modulation of the tight junctions (TJ) (B. J. Aungst, et al., *J. Pharm. Sci.* 89(4):429-442 (2000)). In general, the optimal absorption enhancer should possess the following qualities: its effect should be reversible, it should provide a rapid permeation enhancing effect on the cellular membrane of the mucosa, and it should be non-cytotoxic at the effective concentration level and without deleterious and/or irreversible effects on the cellular or virus membrane. Intranasal compositions may be administered using devices known in the art, for example a nebulizer.

III. Methods of Use

A. Methods of Treatment

1. Administration of Therapeutic Virus

The chimeric viruses, including, for example, Chikungunya VSV chimeric viruses, can be administered to a subject in need thereof in an amount effective to treat a disease or disorder, for example, cancer. Pharmaceutical compositions including a chimeric virus may be administered once or more than once, for example 2, 3, 4, 5, or more times. Serial administration of chimeric virus may occur days, weeks, or months apart.

Virus can be administered peripherally, or can be injected directly into a tumor, for example a tumor within the brain. In addition, virus can be used after resection of the main body of the tumor, for example by administering directly to the remaining adjacent tissue after surgery, or after a period of one to two weeks to allow recovery of local damage. Adding virus after surgical resection would eliminate any remaining tumor cells that the neurosurgeon did not remove. The injections can be given at one, or multiple locations. It is also believed that virus administered systemically can target and kill brain cancers.

In some embodiments, it may be desirable to administer the chimeric virus after or in combination with an immunosuppressant. Treatment with an immunosuppressant during administration with a therapeutic virus allows controlled suppression of the subject's immune system during administration of the therapeutic virus. This may be desirable, for example, if the capacity of the oncolytic virus to kill cancer is reduced due to an earlier administration of the immunizing virus. Treatment with the immunosuppressant is typically transient, and occurs during administration of the virus, particularly when the virus is being used to treat tumors and/or cancer. Following treatment with the chimeric virus, treatment with the immunosuppressant is discontinued and the patient's immunity returns. The duration of immunosuppressive treatment will depend on the condition to be treated. Typically the immunosuppressive treatment will be long enough for the oncolytic virus to kill cancer cells, reduce tumor size, or inhibit tumor progression.

2. Peripheral Administration of Immunizing Virus

One or more peripheral administrations with an immunizing virus can elicit an adaptive immune response that protects the brain from potential side-effects of oncolytic virus therapy. The term immunizing virus includes live virus as well as viral subunits, proteins and fragments thereof, antigenic polypeptides, nucleic acids, and expression vectors containing nucleic acids encoding viral subunits, proteins, or fragments thereof, or antigenic polypeptides which can be useful in eliciting an immune response. For example, if the immunizing virus is a VSV, the immunizing virus includes, but is not limited to, live VSV, the N, P, M, G, or L proteins, or combinations thereof.

The immunizing virus may be the same virus, or a different virus than the therapeutic virus. The immunizing virus should initiate an adaptive immune response that is sufficient to attenuate, reduce, or prevent the neurovirulence of the therapeutic virus. The therapeutic virus administered after a first administration of immunizing virus should have reduced neurovirulence compared to therapeutic virus administered without a first administration of immunizing virus. In preferred embodiments, the immunizing virus is similar to the therapeutic virus. For example if the therapeutic virus is a VSV, the immunizing virus is preferably a VSV, or an antigenic protein or nucleic acid component thereof. In some embodiments the immunizing virus has an attenuated phenotype compared to the therapeutic virus. As described above, suitable immunizing viruses include wildtype viruses, as well as mutant and variants thereof. In one preferred embodiment, the immunizing virus is a wildtype virus or an antigenic protein or nucleic acid component thereof, while the therapeutic virus is a mutant, variant, chimeric virus having the same virus background but reduced neurovirulence compared to wildtype. In some embodiments, therapeutic viruses may be engineered to express therapeutic proteins or targeting molecules Immunizing viruses may also be engineered to express additional proteins, but preferably are not. VSV-G/GFP is a suitable immunizing virus. The nucleotide sequence for VSV-G/GFP is GenBank Accession FJ478454.

Immunizing viruses are administered sufficiently prior to therapeutic viruses to elicit an adaptive immune response Immunizing viruses are typically administered one or more times at least about 5 days, preferably 1 week, more preferably greater than one week before administration of the therapeutic virus Immunizing viruses can be administered up to 1, 2, 3, 4, 5, or more weeks before the therapeutic virus Immunizing viruses can be administered up to 1, 2, 3, 4, 5, or more months before the therapeutic virus. Most preferably the immunizing virus is administered between about ten days and 12 weeks before the therapeutic virus.

After an initial administration of the immunizing virus, subsequent booster immunizations can be administered. For example, it may be desirable to administer the immunizing virus two or more times. A first administration of the immunizing virus is typically provided to a patient in need therefore prior to a first administration of the therapeutic virus. Subsequent administrations of the immunizing virus may occur before and/or after a first administration of the therapeutic virus. In preferred embodiments the immunizing virus is administered two or more times before the first administration of the therapeutic virus. In a non-limiting example, the immunizing virus is first administered on day 1, a booster of immunizing virus is administered six weeks later on about day 43, and the therapeutic virus is first administered two weeks later on about day 57.

Various factors may be considered when determining the frequency, dosage, duration, and number of administrations of immunizing virus, as well as the duration between administration of the immunizing virus and first administration of therapeutic virus. For example, the subject's adaptive immune response can be monitored to assess the effectiveness of the immunization. Methods of measuring adaptive immune activation are known in the art and include antibody profiling, serum analysis for changes in levels of antibodies, cytokines, chemokines, or other inflammatory molecules, and cell counts and/or cell profiling using extracellular markers to assess the numbers and types of immune cells such as B cells and T cells.

Immunizing virus is most typically delivered to a subject in need thereof by peripheral administration, and not directly or locally to the site in need of treatment by therapeutic virus. Peripheral administration includes intravenous, by injection or infusion, intraperitoneal, intramuscular, subcutaneous, and mucosal such as intranasal delivery. In some embodiments, the composition is delivered systemically, by injection or infusion into the circulatory system (i.e. intravenous) or an appropriate lymphoid tissue, such as the spleen, lymph nodes or mucosal-associated lymphoid tissue. The injections can be given at one, or multiple locations. Preferably the immunizing virus is administered intranasally or by intramuscular injection, most preferably by intranasal delivery.

Generally immunizing virus is administered to humans at dosage levels between $10^2$ and $10^{12}$ PFU. Virus is typically administered in a liquid suspension, in a volume ranging between 10 μl and 100 ml depending on the route of administration.

It may also be desirable to administer the immunizing virus in combination with one or more adjuvants. These can be incorporated into, administered with, or administered separately from, the immunogenizing virus. Depending on whether or not the individual is a human or an animal, the adjuvant can be, but is not limited to, one or more of the following: oil emulsions (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

3. Vaccination

The chimeric viruses can also serve as an immunogen for generating an immune response against other antigens administered with or cloned into virus. The safety profile of the Chikungunya-VSVs make them particularly attractive for use as part of a vaccine. Other VSVs can lead to adverse consequence in brain, whereas a Chikungunya-VSV with another antigen, for example, an influenza antigen, would be safer, yet effective.

For example, in some embodiments, the chimeric virus is a vaccine vector. Experiments conducted with the Lassa-VSV including a GFP reporter, show that the chimeric virus generates a strong immune response against the virus, and also against the GFP reporter. Accordingly, other proteins could be substituted for GFP. These could include proteins from pathogenic microbes unrelated to Chikungunya virus or VSV; the Chikungunya-VSV could serve as a safe vaccine platform against many different pathogenic microbes. As described above, VSV can be engineered to express one or more immunogenic antigens. Expression of these antigens in a patient in need thereof presents the antigen to the immune system and provokes an immune response. Vaccines can be administered prophylactically or therapeutically. Vaccines can also be administered according to a vaccine schedule. A vaccine schedule is a series of vaccinations, including the timing of all doses. Many vaccines require multiple doses for maximum effectiveness, either to produce sufficient initial immune response or to boost response that fades over time. Vaccine schedules are known in the art, and are designed to achieve maximum effectiveness. The adaptive immune response can be monitored using methods known in the art to measure the effectiveness of the vaccination protocol.

4. Immunotherapy

Chimeric VSV wherein the G protein is replaced with a heterologous glycoprotein, have been shown to be immunogenic and initiate an up-regulation of both humoral and cellular immunity toward the virus (Geisbert, et al., *PLoS Med.,* 2:e183 (2005)). Therefore, methods of initiating an immune response against the infected tumor are disclosed. It is believed that the CHIKV-VSV chimeric viruses will not only infect and kill cancer cells, but will enhance an attack by the systemic immune system on the infected cell-type both during and after the virus is eliminated. In this way, the virus can be used to induce an immune response against non-infected target cells. In this way, treatment with the VSV may delay, reduce, or prevent reoccurrence of the cancer being treated.

In some methods, the chimeric virus, such as a CHIKV-VSV chimeric virus, is used to infect targets cells, and the infected target cells or antigens isolated therefrom are used for peripheral immunization of the subject against the target cells, or antigens thereof. For example, target cells against which an immune response is desired are implanted into a subject. The cells are injected with virus which kills the cells and leads to an immune response against antigens of the cells. The cells can be infected with virus before or after implantation. For example, the cells are infected with virus in vitro prior to injection into the subject. In another embodiment, the subject is immunized with antigen(s) isolated from tumor cells infected with virus in vitro.

The target cell can be any cell to which an immune response is desired. For example, the target cells can be cancer cells against which an immune response is desired. The cancer cells can be from an established cell line or primary cancer cells isolated from a subject. For example, the target cells can be cancer cells isolated from a subject in a biopsy or during surgery to remove a tumor. As discussed above, the target cells can be infected in vitro prior to administration to the subject, or the target cells can be inject by local injection of the virus into the subject at the site of implantation of the target cells. The cells can be harvested from and administered back to the same subject. Alternatively, the cells can be harvested from one subject and administered to a different subject. In this way, the virus can be used to induce an immune response against a cancer or tumor in a subject that has the cancer or tumor, or prophylactically prime the immune system to attack a future cancer or tumor that the subject does not yet have. Accordingly, the treatment can be therapeutic, prophylactic, or a combination thereof.

In a particular embodiment, this strategy is employed in combination with surgery in which a tumor is removed from a subject. Cells are isolated from the tumor, infected with virus, and implanted in the subject. In this way, an immune response is induced against any cancer cells that remain in the subject, for example in the margins and other tissue at the site from which the tumor removed, as well as circulating cancer cells and metastases throughout the body including those sites distant from the tumor that was removed. The method can also reduce, delay, or prevent recurrence of the cancer.

In some embodiments the isolated target cells are irradiated in amount effective to prevent cell division, but not to kill the cells, to avoid concerns about in vivo replication of the target cells following implantation. Typically, the cells are implanted into the subject peripherally. For example, the cells can be injected into the subject subcutaneously, intramuscularly, intranasally, intravenously, intraperitoneally, or using another suitable method of peripheral administration, such as those discussed above. In some embodiments, the tumor cells are expanded in culture for one or generations or passages between isolation and implantation in the subject.

It is believed that VSV infection will increase tumor-specific cytotoxic effector CD8+ T cells, increase CD4+ T cells, increase production of tumor specific antibodies, or a combination thereof. Therefore, in some embodiments, tumor-specific cytotoxic effector CD8+ T cells primed by chimeric VSV infected tumor cells are administered to a subject in need thereof. The T cells can be harvested from a treated subject, and optionally expanded in culture, or primed and expanded in vitro.

For example, in a particular embodiment, the method is one of adaptive T cell therapy. Methods of adoptive T cell therapy are known in the art and used in clinical practice. Generally adoptive T cell therapy involves the isolation and ex vivo expansion of tumor specific T cells to achieve greater number of T cells than what could be obtained by vaccination alone. The tumor specific T cells are then infused into patients with cancer in an attempt to give their immune system the ability to overwhelm remaining tumor via T cells which can attack and kill cancer. Several forms of adoptive T cell therapy can be used for cancer treatment including, but not limited to, culturing tumor infiltrating lymphocytes or TIL; isolating and expanding one particular T cell or clone; and using T cells that have been engineered to recognize and attack tumors. In the methods, the tumors infected with the CHIKV-VSV chimeric viruses, or isolated components thereof, are used to prime the T cells. In some embodiments, the T cells are taken directly from the patient's blood after they have received treatment or immunization with the virus. Methods of priming and activating T cells in vitro for adaptive T cell cancer therapy are known in the art. See, for example, Wang, et al., Blood, 109(11): 4865-4872 (2007) and Hervas-Stubbs, et al., *J. Immunol.*, 189(7):3299-310 (2012). The methods can be used in conjunction with virus infected cancer cells, or antigens isolated therefrom, to prime and activate T cells against the cancer.

Historically, adoptive T cell therapy strategies have largely focused on the infusion of tumor antigen specific cytotoxic T cells (CTL) which can directly kill tumor cells. However, CD4+ T helper (Th) cells can also be used. Th can activate antigen-specific effector cells and recruit cells of the innate immune system such as macrophages and dendritic cells to assist in antigen presentation (APC), and antigen primed Th cells can directly activate tumor antigen-specific CTL. As a result of activating APC, antigen specific Th1 have been implicated as the initiators of epitope or determinant spreading which is a broadening of immunity to other antigens in the tumor. The ability to elicit epitope spreading broadens the immune response to many potential antigens in the tumor and can lead to more efficient tumor cell kill due to the ability to mount a heterogeneic response. In this way, adoptive T cell therapy can used to stimulate endogenous immunity.

B. Subjects to be Treated

In general, the chimeric viruses and methods of treatment thereof are useful in the context of cancer, including tumor therapy, particular brain tumor therapy.

In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site.

The compositions and methods described herein are useful for treating subjects having benign or malignant tumors by delaying or inhibiting the growth of a tumor in a subject, reducing the growth or size of the tumor, inhibiting or reducing metastasis of the tumor, and/or inhibiting or reducing symptoms associated with tumor development or growth. The examples below indicate that the viruses and methods are useful for treating cancer, particular brain tumors, in vivo.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. The compositions are particularly effective in treating carcinomas. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated with the provided compositions and methods include, but are not limited to, cancers such as vascular cancer such as multiple myeloma, adenocarcinomas and sarcomas, of bone, bladder, brain, breast, cervical, colo-rectal, esophageal, kidney, liver, lung, nasopharangeal, pancreatic, prostate, skin, stomach, and uterine. In some embodiments, the compositions are used to treat multiple cancer types concurrently. The compositions can also be used to treat metastases or tumors at multiple locations.

The methods are particularly useful in treating brain tumors. Brain tumors include all tumors inside the cranium or in the central spinal canal. They are created by an abnormal and uncontrolled cell division, normally either in the brain itself (neurons, glial cells (astrocytes, oligodendrocytes, ependymal cells, myelin-producing Schwann cells, lymphatic tissue, blood vessels), in the cranial nerves, in the brain envelopes (meninges), skull, pituitary and pineal gland, or spread from cancers primarily located in other organs (metastatic tumors). Examples of brain tumors include, but are not limited to, oligodendroglioma, meningioma, supratentorial ependymona, pineal region tumors, medulloblastoma, cerebellar astrocytoma, infratentorial ependymona, brainstem glioma, schwannomas, pituitary tumors, craniopharyngioma, optic glioma, and astrocytoma.

"Primary" brain tumors originate in the brain and "secondary" (metastatic) brain tumors originate from cancer cells that have migrated from other parts of the body. Primary brain cancer rarely spreads beyond the central nervous system, and death results from uncontrolled tumor growth within the limited space of the skull. Metastatic brain cancer indicates advanced disease and has a poor prognosis. Primary brain tumors can be cancerous or noncancerous. Both types take up space in the brain and may cause serious symptoms (e.g., vision or hearing loss) and complications (e.g., stroke). All cancerous brain tumors are life threatening (malignant) because they have an aggressive and invasive nature. A noncancerous primary brain tumor is life threatening when it compromises vital structures (e.g., an artery). In a particular embodiment, the compositions and methods are used to treat cancer cells or tumors that have metastasized from outside the brain (e.g., lung, breast, melanoma) and migrated into the brain.

The Examples below illustrate that CHIKV-VSV chimeric viruses have superior oncolytic property, but also non-toxic to health or normal cells, even when administered directly to the brain. Therefore, the viruses are particularly useful for treating brain cancer, cancer that can metastasize to the brains, for example lung cancer, breast cancer, and skin cancer such as melanoma.

For example, the experiments below illustrate that in addition to gliomas, and a metastatic brain tumor, melanoma, VSVΔG-CHIKV also infects a number of other types of cancer cells including breast cancer cells. VSVΔG-CHIKV also selectively targets a type of cancer cell that originates from melanocytes in the skin and metastasizes into the brain. The chimeric visues also have the potential to target and selectively infect cells that have migrated away from the main tumor body. In an experimental model of brain metastasis discussed below, multiple melanoma tumor sites were initiated within the brain. Subsequent to selective infection of one tumor (melanoma), VSVΔG-CHIKV migrated away from the injected tumor to selectively infect another experimental tumor within the same brain. This was true both when the secondary tumor was situated in the mirror contralateral striatum, and also when the secondary tumor was situated in the contralateral cerebral cortex and the primary tumor was in the striatum. Infection of multiple tumors in a single brain was accomplished with little detectable infection in the normal brain between the two tumors.

Thus, although the viruses are particularly safe and useful for treating cancer in the brain, the cancer does not have to be in the brain. It is believed that the chimeric virus are also effective for treating other cancer outside the brain, and can thereof be administered systemically in or locally outside the brain. In a particular embodiment, a chimeric virus is used to treat a cancer that could, but has not yet metastasized to the brain. See, for example, Yarde, et al., *Cancer Gene Ther.,* 2013 Nov. 1. doi: 10.1038/cgt.2013.63, which describes that intravenously administered VSVs encoding IFN-β have potent activity against subcutaneous tumors in the 5TGM1 mouse myeloma model, without attendant neurotoxicity. However, when 5TGM1 tumor cells were seeded intravenously, virus-treated mice with advanced myeloma developed clinical signs indicative of meningoencephalitis, and leading to deaths that are believed to be associated with viral toxicity. Histological analysis revealed that systemically administered 5TGM1 cells seed to the CNS, forming meningeal tumor deposits, and that VSV infects and destroys these tumors. Death is presumably a consequence of meningeal damage and/or direct transmission of virus to adjacent neural tissue.

The CHIKV-VSV chimeric viruses have negligible toxicity for normal and healthy cells including neurons. Therefore, these viruses are a safer, less toxic alternative for treating systemic cancers that can potential traffic virus into the brain and cause neurotoxicity and even death.

As shown in the experiments below, the CHIKV-VSV chimeric viruses were safe in the brains of immunocompetent mice. Thus, CHIKV-VSV chimeric viruses should be far safer than VSV with its normal VSV glycoprotein. This may enable CHIKV-VSV chimeric viruses to be used in patients showing depressed immunity, typical of many cancer patients, and also of patients with AIDS, or with genetic immune depression. The enhanced safety in the brain may also be of benefit in patients with compromised blood brain barriers where CHIKV-VSV chimeric viruses would be safer than VSV in both cancer treatment, and for vaccination against either a cancer cell type, or against unrelated (e.g., non-Lassa, non-VSV) pathogenic microbes.

The experiments below also show that the CHIKV-VSV chimeric viruses are effective at infecting multiple brain tumors after injection into a single tumor in a model of metastatic brain cancer. It is believed that the virus is effective for treating both primary and secondary brain tumors, but as peripheral (non-brain) cancers and tumors.

C. Combination Therapies

In some embodiments, the methods include administration of two or more different chimeric VSVs. In successive uses of an experimental VSV vaccine with the same VSV glycoprotein, on repeated immunizations the immune system targeted the VSV glycoprotein rather than the accompanying HIV antigen of interest, thereby defeating the potential for vaccination against AIDS. However, the use of three different VSV glycoproteins in successive vaccinations enhanced the immune response to the HIV protein of vaccine interest (Rose et al., *Cell,* 106, 539-549 (2001)). This points at the possible advantage of potentially employing different glycoproteins if more than one treatment with an oncolytic virus may be needed to generate a directed immune response against an infectible tumor. Other chimeric viruses having a VSV background and heterologous glycoprotein include, but are not limited to, those having glycoproteins from Lassa, rabies, lymphocytic choriomeningitis virus (LCMV), Ebola, or Marburg virus. See, e.g., U.S. Pat. No. 10,179,154, which is specifically incorporated by reference in its entirety. Thus, these or other chimeric viruses may be used in combination with, for example, a CHIKV-VSV chimeric virus.

Administration of the compositions containing oncolytic viruses may also be coupled with surgical, radiologic, other therapeutic approaches to treatment of tumors and cancers.

1. Surgery

The compositions and methods can be used as an adjunct to surgery. Surgery is a common treatment for many types of benign and malignant tumors. As it is often not possible to remove all the tumor cells from during surgery, the compositions containing oncolytic virus are particularly useful subsequent to resection of the primary tumor mass, and would be able to infect and destroy even dispersed tumor cells.

In a preferred embodiment, the compositions and methods are used as an adjunct or alternative to neurosurgery. The compositions are particularly well suited to treat areas of the brain that is difficult to treat surgically, for instance high grade tumors of the brain stem, motor cortex, basal ganglia, or internal capsule. High grade gliomas in these locations are generally considered inoperable. An additional situation where an oncolytic virus may be helpful is in regions where the tumor is either wrapped around critical vasculature, or in an area that is difficult to treat surgically.

2. Therapeutic Agents

The viral compositions can be administered to a subject in need thereof alone or in combination with one or more additional therapeutic agents selected based on the condition, disorder or disease to be treated. A description of the various classes of suitable pharmacological agents and drugs may be found in Goodman and Gilman, *The Pharmacological Basis of Therapeutics,* (11th Ed., McGraw-Hill Publishing Co.) (2005).

Additional therapeutic agents include conventional cancer therapeutics such as chemotherapeutic agents, cytokines, chemokines, and radiation therapy. The majority of chemotherapeutic drugs can be divided into: alkylating agents, antimetabolites, anthracyclines, plant alkaloids, topoisomerase inhibitors, and other antitumor agents. All of these drugs affect cell division or DNA synthesis and function in some way. Additional therapeutics include monoclonal antibodies and the tyrosine kinase inhibitors e.g., imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to, amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epipodophyllotoxins, epirubicin, etoposide, etoposide phosphate, fludarabine, fluorouracil, gemcitabine, hydroxycarbamide, idarubicin, ifosfamide, irinotecan, leucovorin, liposomal doxorubicin, liposomal daunorubicin, lomustine, mechlorethamine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, teniposide, tegafur-uracil, temozolomide, teniposide, thiotepa, tioguanine, topotecan, treosulfan, vinblastine, vincristine, vindesine, vinorelbine, taxol and derivatives thereof, trastuzumab (HERCEPTIN®), cetuximab, and rituximab (RITUXAN® or MABTHERA®), bevacizumab (AVASTIN®), and combinations thereof. Representative pro-apoptotic agents include, but are not limited to, fludarabinetaurosporine, cycloheximide, actinomycin D, lactosylceramide, 15d-PGJ(2), and combinations thereof.

Preferred chemotherapeutics will affect tumors or cancer cells, without diminishing the activity of the virus. For example, in a preferred embodiment, the additional therapeutic agent inhibits proliferation of cancer cells without affecting targeting, infectivity, or replication of the virus.

a. Anticancer Agents

The compositions can be administered with an antibody or antigen binding fragment thereof specific for growth factor receptors or tumor specific antigens. Representative growth factors receptors include, but are not limited to, epidermal growth factor receptor (EGFR; HER1); c-erbB2 (HER2); c-erbB3 (HER3); c-erbB4 (HER4); insulin receptor; insulin-like growth factor receptor 1 (IGF-1R); insulin-like growth factor receptor 2/Mannose-6-phosphate receptor (IGF-II R/M-6-P receptor); insulin receptor related kinase (IRRK); platelet-derived growth factor receptor (PDGFR); colony-stimulating factor-1receptor (CSF-1R) (c-Fms); steel receptor (c-Kit); Flk2/Flt3; fibroblast growth factor receptor 1 (Flg/Cek1); fibroblast growth factor receptor 2 (Bek/Cek3/K-Sam); Fibroblast growth factor receptor 3; Fibroblast growth factor eceptor 4; nerve growth factor receptor (NGFR) (TrkA); BDNF receptor (TrkB); NT-3-receptor (TrkC); vascular endothelial growth factor receptor 1 (Fla); vascular endothelial growth factor receptor 2/Flk1/KDR; hepatocyte growth factor receptor (HGF-R/Met); Eph; Eck; Eek; Cek4/Mek4/HEK; Cek5; Elk/Cek6; Cek7; Sek/Cek8; Cek9; Cek10; HEK11; 9 Ror1; Ror2; Ret; Ax1; RYK; DDR; and Tie.

b. Therapeutic Proteins

It may be desirable to administer the disclosed compositions in combination with therapeutic proteins. VSV is an effective oncolytic virus, in-part, by taking advantage of defects in the interferon system. Administration of therapeutic proteins such as IFN-α, or IFN-α/β pathway inducer polyriboinosinic polyribocytidylic acid [poly(I:C)] are effective in protecting normal cells from the oncolytic activity, while leaving the tumor cells susceptible to infection and death (Wollmann, et al. *J. Virol.*, 81(3): 1479-1491 (2007). Therefore, in some embodiments, the compositions are administered in combination with a therapeutic protein to reduce infectivity and death of normal cells.

Other therapeutic proteins that can be administered in combination with the viruses include those provided above as therapeutic proteins that can be engineered into the virus. Accordingly, the therapeutic virus can be part of the virus itself, or administered separately. In some embodiments, the virus includes one or more therapeutic proteins and one more therapeutic proteins are administered separately.

c. Immuno-Suppressants

As discussed throughout and demonstrated in the Examples below, the CHIKV-VSV chimeric viruses generally, show a dramatically reduced probability of infecting normal brain cells, but still have a superior oncolytic capacity. One limitation of oncolytic viruses in general is that the adaptive immune system can up-regulate its antiviral response and eliminate the virus before the virus has had a chance to maximally infect tumor cells. Although it is important for the adaptive immune system to eliminate the chimeric VSV from the subject, the virus should remain in the subject long enough to infect and kill as many tumor cells as possible balanced against the pathogenicity of the virus to normal cells of the subject. Temporary concomitant immune-suppression has been identified as a strategy to enhance the efficacy of other oncolytic viruses (HSV, adenovirus, vaccinia) that are human pathogens and face pre-existing immunity (Fukuhara, et al., *Curr. Cancer Drug Targets,* 7:149-155 (2007); Lun, et al., *Clin. Cancer Res.,* 15:2777-2788 (2009)). Therefore, the virus can be administered to the subject in combination with temporary concomitant immune suppression.

In some embodiments, the virus is administered in combination with an agent that reduces or attenuates the intrinsic IFN-mediated immune responses that can eliminate the virus before it has achieved maximal tumor destruction. In preferred embodiments, the attenuation of the intrinsic IFN-mediated immune responses enhances the rate of recombinant VSV-mediated tumor destruction without increasing infection of normal cells. This strategy should also reduce the initiation of the adaptive immune response which is enhanced by the innate immune response, giving the virus more time to complete its oncolytic actions.

Paglino, et al., *J. Virol.,* 85:9346-58 (2011) showed that a cancer cell highly resistant to VSV could be infected by blocking the IFN response to VSV with one of three IFN blockers, valproate, the vacccinia protein B18R, or Jak inhibitor 1. Valproate crosses the blood brain barrier as evident in its use to treat epilepsy. It is already approved for clinical use in humans (for attenuating epilepsy), and like many other histone deacetylase (HDAC) inhibitors, it has an intrinsic anti-tumor property, independent of oncolytic virus infection, that reduces glioma and other tumor growth in the brain (Chateauvieux, et al., *J. Biomed. Biotechnol.,* 479364. Epub 2010 Jul. 29 (2010); Fu, et al., *Neuro. Oncol.,* 12:328-340 (2010); Su, et al., *Clin. Cancer* Res., 17:589-597 (2011). Similarly, the HDAC inhibitor vorinostat (ZOLINZA®) is approved by the FDA for the treatment of cutaneous T-cell lymphoma (Glaser K B, *Biochem. Pharmacol.,* 74:659-671 (2007)). Vorinostat on its own appears to penetrate brain tumors and to increase survival of patients with glioblastoma, and animal studies have shown that valproate can increase infection by viruses in tumors with minimal increased collateral damage. Valproate increased survival substantially in tumor bearing animals treated with HSV (Otsuki, et al., *Mol. Ther.,* 16:1546-1555 (2008)). In one particular case study a pediatric anaplastic astrocytoma that was resistant to chemotherapy and irradiation, underwent a substantial regression after combined treatment with oral valproate and oncolytic attenuated Newcastle disease virus Wagner, et al., *APMIS,* 114:731-743 (2006)).

Other HDAC inhibitors have been shown to enhance viral cancer cell targeting and viral replication by vaccinia (MacTavish, et al., *PLoS One,* 5:e14462 (2010) and VSV (Nguyen, et al., *Proc. Nall. Acad. Sci., USA* 105:14981-14986 (2008)) without substantially altering infection in normal non-cancer cells. Valproate inhibited the induction of several antiviral genes after oncolytic HSV infection, and resulted in enhanced viral propagation in glioma cells, even in the presence of IFN (Otsuki, et al., *Mol. Ther.,* 16:1546-1555 (2008)). Importantly, valproate treatment had no augmenting effect on viral yield in normal human astrocytes. Valproate pretreatment was also shown to enhance HSV propagation in tumors 10-fold in vivo and improved the survival of nude mice bearing U87delta-EGFR brain tumors.

Therefore, in some embodiments, the virus is administered in combination with an HDAC inhibitor. In some embodiments, the virus is administered in combination with valproate, the vacccinia protein B18R, Jak inhibitor 1, or vorinostat.

Other immunosuppressants such as cyclosporin, prednisone, dexamethasone, or other steroidal anti-inflammatory, can also be used to reduce the immune response immediately before, during, or shortly after administration of the therapeutic virus. The immunosuppressant is then discontinued or decreased to allow the patient's immune system to prevent inflammation and/or killing of the virus after it has competed the desired killing of tumor or diseased tissue.

Suitable immunosuppressants are known in the art and include glucocorticoids, cytostatics (such as alkylating agents, antimetabolites, and cytotoxic antibodies), antibodies (such as those directed against T-cell recepotors or 11-2 receptors), drugs acting on immunophilins (such as cyclosporine, tacrolimus, and sirolimus) and other drugs (such as interferons, opioids, TNF binding proteins, mycophenolate, and other small molecules such as fingolimod). The dosage ranges for immunosuppressant agents are known in the art. The specific dosage will depend upon the desired therapeutic effect, the route of administration, and on the duration of the treatment desired. For example, when used as an immunosuppressant, a cytostatic may be administered at a lower dosage than when used in chemotherapy Immunosuppressants include, but are not limited to, FK506, prednisone, methylprednisolone, cyclophosphamide, thalidomide, azathioprine, and daclizumab, physalin B, physalin F, physalin G, seco-steroids purified from *Physalis angulata L.*, 15-deoxyspergualin, MMF, rapamycin and its derivatives, CCI-779, FR 900520, FR 900523, NK86-1086, depsidomycin, kanglemycin-C, spergualin, prodigiosin25-c, cammunomicin, demethomycin, tetranactin, tranilast, stevastelins, myriocin, gliotoxin, FR 651814, SDZ214-104, bredinin, WS9482, mycophenolic acid, mimoribine, misoprostol, OKT3, anti-IL-2 receptor antibodies, azasporine, leflunomide, mizoribine, azaspirane, paclitaxel, altretamine, busulfan, chlorambucil, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, bleomycin, dactinomycin, daunorubicin, doxirubicin, idarubicin, mitoxantrone, losoxantrone, mitomycin-c, plicamycin, paclitaxel, docetaxel, topotecan, irinotecan, 9-amino camptothecan, 9-nitro camptothecan, GS-211, etoposide, teniposide, vinblastine, vincristine, vinorelbine, procarbazine, asparaginase, pegaspargase, octreotide, estramustine, and hydroxyurea, and combinations thereof. Preferred immunosuppressants will preferentially reduce or inhibit the subject's immune response, without reducing or inhibiting the activity of the virus.

IV. Kits

Dosage units including virus in a pharmaceutically acceptable carrier for shipping and storage and/or administration are also disclosed. Active virus should be shipped and stored using a method consistent with viability such as in cooler containing dry ice so that viruses are maintained below 4° C., and preferably below −20° C. VSV should not be lyophilized. Components of the kit may be packaged individually and can be sterile. In one embodiment, a pharmaceutically acceptable carrier containing an effective amount of virus is shipped and stored in a sterile vial. The sterile vial may contain enough virus for one or more doses. Virus may be shipped and stored in a volume suitable for administration, or may be provided in a concentrated titer that is diluted prior to administration. In another embodiment, a pharmaceutically acceptable carrier containing an effective amount of virus can be shipped and stored in a syringe.

Typical concentrations of concentrated viral particles in the sterile saline, phosphate buffered saline or other suitable media for the virus is in the range of $10^8$ to $10^9$ with a maximum of $10^{12}$. Dosage units should not contain membrane disruptive agents nor should the viral solution be frozen and dried (i.e., lyophilized), which could kill the virus.

Kits containing syringes of various capacities or vessels with deformable sides (e.g., plastic vessels or plastic-sided vessels) that can be squeezed to force a liquid composition out of an orifice are provided. The size and design of the syringe will depend on the route of administration. For example, in one embodiment, a syringe for administering virus intratumorally, is capable of accurately delivering a smaller volume (such as 1 to 100 µl). Typically, a larger syringe, pump or catheter will be used to administer virus systemically. Any of the kits can include instructions for use.

V. Methods of Manufacture

A. Engineering Recombinant VSVs

The native VSV genome is a single negative-sense, non-segmented stand of RNA that contains five genes (N, L, P, M, and G) and has a total size of 11.161 kb. Methods of engineering recombinant viruses by reconstituting VSV from DNA encoding a positive-sense stand of RNA are known in the art (Lawson, et al., *PNAS*, 92:4477-4481 (1995), Dalton and Rose, *Virology.*, 279:414-421 (2001)). For example, recombinant DNA can be transcribed by T7 RNA polymerase to generate a full-length positive-strand RNA complimentary to the viral genome. Expression of this RNA in cells also expressing the VSV nucleocapsid protein and the two VSV polymerase subunits results in production of VSV (Lawson, et al., *PNAS*, 92:4477-4481 (1995)). In this way, VSVs can be engineered to express variant proteins, additional proteins, foreign antigens, targeting proteins, or therapeutic proteins using known cloning methods. Methods of preparing exemplary suitable VSVs where the gene encoding the VSV G protein is deleted and replaced with a gene encoding the Lassa virus glycoprotein are described in more detail above.

In some embodiments, the chimeric VSV is prepared by substituting the sequence encoding the G protein on the plasmid referred as VSVXN2 (Schnell, et al., *J. Virol.*, 70:2318-2323 (1996)) with a heterologous glycoprotein, such as the glycoprotein from Lassa virus.

In other embodiments the chimeric VSV is prepared by substituting the sequence encoding the G protein on plasmid pVSV(+) described in Whelan, et al., *Proc. Natl. Acad. Sci. U.S.A.*, 92(18):8388-92 (1995). Whelan describes the constructions of a full-length cDNA clone of VSV assembled from clones of each of the VSV genes and intergenic junctions. These clones were assembled into a full-length cDNA and inserted in both orientations between the bacteriophage T7 promoter and a cDNA copy of the self-cleaving ribozyme from the antigenomic strand of HDV. The resulting plasmids were named pVSV1(+) and pVSV1(−) to reflect the polarity of the T7 transcript they generated: VSV antigenomic or genomic RNA, respectively.

The T7 transcripts contained two non-VSV nucleotides (GG) at their 5' ends but were cleaved by the HDV ribozyme to generate a 3' terminus which corresponded precisely to the 3' end of the VSV antigenomic or genomic sequence, an important requirement for VSV RNA replication. Transfection of plasmids into BHK21 cells infected with vTF7-3 was performed under the conditions and with quantities of support plasmids as described (Pattnaik, et al., *Cell,* 69:1011-1020 (1992)), and up to 5 ug of pVSV1(+) or pVSV1(−). Transfected cells were incubated at 31° C. or 37° C. For some experiments, pVSV1(+) and pVSV1(−) were linearized by digestion at a unique Nhe I site located downstream of the T7 terminator in the pGEM-3-based plasmids.

To identify cDNA-derived virus unambiguously, several genetic markers were incorporated into the full-length cDNA clones. All five genes were of the Indiana serotype of VSV, but whereas the N, P, M, and L genes originated from the San Juan strain, the G gene was from the Orsay strain. In addition, the functional P clone has 28 nucleotide sequence differences from the published San Juan sequence and in the case of pVSV1(+) the 516 nt at the 5' end of the VSV genome originated from pDI, the clone of DI-T RNA (Pattnaik, et al., *Cell,* 69:1011-1020 (1992)).

B. Creating Mutant VSV

RNA viruses are prone to spontaneous genetic variation. The mutation rate of VSV is about 10' per nucleotide replicated, which is approximately one nucleotide change per genome (Drake, et al., *Proc. Natl. Acad. Sci. USA,* 96:13910-13913). Therefore, mutant VSVs exhibiting desired properties can be developed by applying selective pressure. Methods for adaption of VSVs through repeated passaging is described in the art. See, for example, Wollmann, et al., *J. Virol.,* 79(10): 6005-6022 (2005). Selective pressure can be applied by repeated passaging and enhanced selection to create mutant virus with desirable traits such as increased infectivity and oncolytic potential for a cell type of interest. The cell type of interest could be general, such as cancer cells, or specific such as glioblastoma cells. Mutant virus can also be selected based on reduced toxicity to normal cells. Methods of enhanced selection include, but are not limited to, short time for viral attachment to cells, collection of early viral progeny, and preabsorption of viral particles with high affinity of undesirable cells (such as normal cells). Mutations can be identified by sequencing the viral genome and comparing the sequence to the sequence of the parental strain.

DNA encoding the VSV genome can also be used as a substrate for random or site directed mutagenesis to develop VSV mutant viruses. Mutagenesis can be accomplished by a variety of standard, mutagenic procedures. Changes in single genes may be the consequence of point mutations that involve the removal, addition or substitution of a single nucleotide base within a DNA sequence, or they may be the consequence of changes involving the insertion or deletion of large numbers of nucleotides.

Mutations can arise spontaneously as a result of events such as errors in the fidelity of nucleic acid replication or the movement of transposable genetic elements (transposons) within the genome. They also are induced following exposure to chemical or physical mutagens. Such mutation-inducing agents include ionizing radiations, ultraviolet light and a diverse array of chemicals such as alkylating agents and polycyclic aromatic hydrocarbons all of which are capable of interacting either directly or indirectly (generally following some metabolic biotransformations) with nucleic acids. The nucleic acid lesions induced by such environmental agents may lead to modifications of base sequence when the affected DNA is replicated or repaired and thus to a mutation. Mutation also can be site-directed through the use of particular targeting methods. Various types of mutagenesis such as random mutagenesis, e.g., insertional mutagenesis, chemical mutagenesis, radiation mutagenesis, in vitro scanning mutagenesis, random mutagenesis by fragmentation and reassembly, and site specific mutagenesis, e.g., directed evolution, are described in U.S. Patent Application No. 2007/0026012.

Mutant viruses can be prepared by site specific mutagenesis of nucleotides in the DNA encoding the protein, thereby producing DNA encoding the mutant. Techniques for making substitution mutations at predetermined sites in DNA having a known sequence are well known, for example M13 primer mutagenesis and PCR mutagenesis Amino acid substitutions are typically of single residues, but can occur at a number of different locations at once. Insertions usually will be on the order of about from 1 to 10 amino acid residues; and deletions will range about from 1 to 30 residues. Substitutions, deletions, insertions or any combination thereof can be combined to arrive at a final construct. The mutations must not place the sequence out of reading frame and preferably will not create complementary regions that could produce secondary mRNA structure. Substitution variants are those in which at least one residue has been removed and a different residue inserted in its place.

The present invention will be further understood by reference to the following non-limiting examples.

Zhang, et al., "Chikungunya-vesicular stomatitis chimeric virus targets and eliminates brain tumors," *Virology,* 522: 244-259 (2018), is specifically incorporated by reference herein in its entirety.

EXAMPLES

Example 1: Human Cancer Cells have High Susceptibility to CHIKV

Materials and Methods

Virus and Cells

VSVΔG-CHIKV was generated by replacing the VSV G gene with the genes coding for the entire CHIKV envelope polyprotein (E3-E2-6K-E1) derived from the prototypic African strain CHIKV S27, as described by Chattopadhyay, et al., *J. Virol.,* 87:395-402 (2013). This CHIKV-VSV chimera incorporated functional CHIKV glycoproteins into the viral envelope, resulting in a replication competent virus. To demonstrate that this chimeric virus showed the proper incorporation of CHIKV glycoproteins, VSVΔG-CHIKV was tested with $^{35}$S labeling of CHIKV envelope polyprotein and measurements of replication kinetics (one-step growth curves) comparing VSVΔG-CHIKV and the parental recombinant wild-type VSV (VSVwt) (Chattopadhyay, et al., *J. Virol.,* 87:395-402 (2013)). Stocks of VSVΔG-CHIKV were grown and harvested using BHK-21 cells and titers of harvested viral stocks were determined by plaque assay using Vero cells.

VSV-LASV-GPC used in vivo is a VSV chimera with the Lassa fever virus glycoprotein gene replacing the VSV glycoprotein gene (Wollmann, et al., *J. Virol.,* 89:6711-6724 (2015); Jae, et al., *Science,* 340:479-483 (2013)). VSV-LASV-GPC was used in vitro (Wollmann, et al., *J. Virol.,* 89:6711-6724 (2015); Garbutt, et al., *J Virol.* 78(10):5458-

65 (2004)). VSVwt is a recombinant wild-type VSV (Lawson, et al., *Proc. Natl. Acad. Sci. USA*, 92:4477-4481 (1995)).

Normal human glia were derived from human temporal lobectomies, as described by Ozduman, et al., *J. Neurosci.*, 28:1882-1893 (2008)). Stably transfected cancer cells expressing red fluorescent protein (RFP) (rU87 and rYUMAC) were generated as described by Wollmann, et al., *J. Virol.*, 87:6644-6659 (2013)). rU373 and rU118 cells were generated using a lentiviral vector expressing RFP, then selected using G418. Mouse glia were isolated and cultured as described by van den Pol, et al., *J. Neurosci.*, 12:2648-2664 (1992); van den Pol, et al., *Neuroscience*, 95:603-616 (2000)). U87, 501mel, YUMAC, Vero, and mouse glia were maintained in MEM. BHK-21, U373, U118, CT-2A and human glia were maintained in DMEM. MDA-MB-436, MDA-MB-231 and BT-549 human breast cancer cells were maintained in RPMI 1640. All culture media (MEM, DMEM, RPMI 1640; Gibco, Life Technologies, Grand Island, N.Y.) was supplemented with 10% fetal bovine serum (Gibco) and 1% pen-strep solution (Gibco). All cells were maintained at 37° C. in an atmosphere supplemented with 5% CO2.

Viral Plaque-Size Assay

A number of different cells were used, including human glioblastoma U373, U118, U87 and mouse glioblastoma CT-2A, human normal glia, mouse glia, human melanoma YUMAC and 501mel, breast cancer MDA-MB-436, MDA-MB-231 (Drs. L. Pusztai, V. Wali), BT-549 cells (ATCC, Manassas, Va.) to study virus infection and replication.

To compare plaque sizes of VSVΔG-CHIKV on normal and multiple cancer cell types, cell monolayers were infected at an MOI of 0.02. Two hours later, inoculum was removed and cultures were washed 3 times with PBS before the addition of CMC in MEM, which was used as overlay. Three days later, plaques were determined by immunostaining. Plaque size was measured (n=20 plaques/cell type/virus) and means and standard errors of the means (SEMs) were determined as an approach to compare infection and replication of VSVΔG-CHIKV.

Immunocytochemistry

At the indicated time points, cells were harvested and incubated in 4% (wt/vol) paraformaldehyde at 4° C. for 24 hrs. A primary rabbit anti-wild type VSV antibody (Johnson et al., 1997) or rat anti-VSV antibody was used (overnight incubation; dilution 1:3,000) to immunostain the sections. The VSV antibody binds to multiple VSV proteins, allowing detection of chimeric VSV viruses expressing non-VSV glycoproteins. After multiple washes to eliminate free primary antibody, a secondary goat anti-rabbit antibody conjugated to a green fluorescent molecule (Alexa Fluor 488; A11008; Invitrogen) or anti-rat secondary (2 h; dilution 1:1,000) was used to localize the virus in infected cells. Finally, cells were incubated in nuclear stain Hoechst33342 (5 mg/ml in PBS) or, for cell death experiments, ethidium homodimer 1 (EthD-1; cat no. 40010; Biotium Inc, Fremont, Calif.) 2 µM in PBS for 20 min in the dark. Images were captured using a fluorescent microscope (Olympus IX71, Tokyo, Japan) fitted with a SPOT-RT camera (Diagnostic Instruments, Sterling Heights, Mich.). Contrast and brightness were corrected with universal application to the entire photograph using Adobe Photoshop.

Statistics

Statistical significance was analyzed by ANOVA; a p-value<0.05 was considered significant. Kaplan-Meier survival curves and log-rank test were used to compare survival rates. Analysis was facilitated with the use of SPSS 19.0. The data are expressed as the mean+/−SEM for each group.

Results

A CHIKV-VSV chimera VSVΔG-CHIKV was used in which the VSV glycoprotein was replaced with the glycoprotein sequence from CHIKV (FIG. 1A). To determine whether VSVΔG-CHIKV displayed a preferential infection of cancer cells, a variety of different cell types were compared, including both cancer and non-cancer normal control cells. The cells used included human glioma U373, U118 and U87 and the mouse glioma CT-2A, along with normal human glia and normal mouse glia. Additional cancer types included the human melanoma cells YUMAC and 501mel, and the breast cancer cells MDA-MB-436, MDA-MB-231 and BT-549. Cells were inoculated using an MOI of 0.02 and VSVΔG-CHIKV infection was determined by immunostaining at 3 days post-infection (dpi). The percentage of infected human glioma cells (n=6 samples/group) was substantially greater than that of normal human glia (U373 p<0.001; U118 p<0.05; U87p<0.05; ANOVA) (FIG. 1B). Additionally, the percentage of infected human YUMAC melanoma and breast cancer cells (MB-231) was also significantly greater than control normal human cells (glia) (YUMAC p<0.01; 501mel p<0.01; MB-231 p<0.05 ANOVA) (FIG. 1B). Mouse glioma CT-2A cells also showed a greater percentage of infected cells than normal mouse glia, but displayed less infection than human gliomas (FIG. 1B).

To compare relative levels of infection and replication of VSVΔG-CHIKV in different cell types, virus plaque size on glioma, melanoma, breast cancer and normal human brain cells was compared 3 days post infection. All human glioma cell lines yielded large plaques (n=20 plaques/group p<0.001 vs normal human glia, ANOVA), whereas on normal human glia VSVΔG-CHIKV displayed significantly smaller plaques (p<0.001; ANOVA) (FIG. 2A,C). Both mouse glioma (CT-2A) and normal mouse glia showed less susceptible to VSVΔG-CHIKV. In comparisons of breast cancer cells, BT-549 displayed a significantly larger (n=20 plaques; p<0.001; ANOVA) plaque size than MDA-MB-231 or MDA-MB-436 cells. YUMAC and 501 human melanoma cells also yielded larger plaques than normal human cells (FIG. 2B,C). Infected cells ultimately showed a lethal response to virus infection as corroborated with ethidium homodimer labeling.

Example 2. VSVΔG-CHIKV Selectively Infects a Broad Range of Human Glioma

In order to examine further the susceptibility of human glioma cells to VSVΔG-CHIKV infection, a panel of different glioma with different growth characteristics and mutational defects were infected with VSVΔG-CHIKV at a low MOI of 0.02.

Materials and Methods

To assess the capability of VSVΔG-CHIKV to propagate in glioblastoma cells, monolayer cultures of the cells were infected with CHIKV at an MOI of 0.02 (primary inoculation). Two hours later, virus inoculum was removed and cells were washed 3 times. To test for viral propagation in these cells, supernatant was filtered (0.22 um) and transferred to uninfected tumor dishes (secondary inoculation). Twenty-four hours later, positive immunofluorescence indicates transfer of viral progeny produced by tumors infected during primary inoculation. A recombinant hybrid type-I interferon IFN-α A/D (Sigma-Aldrich; catalog no. I4401) was used in some experiments.

Results

To test for viral propagation, media was collected from these cultures and filtered (0.22 µm filter) before transferring to fresh cultures of uninfected cells (secondary inoculation). After 24 h infection, all tumor lines showed infection as indicated by immunostaining with antisera against VSV.

Figure 6:
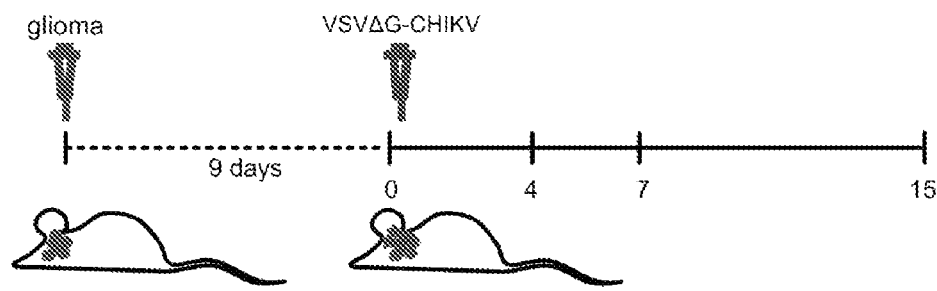
FIG. 6 is a schematic illustration outlining an in vivo experimental procedure. CB17 SCID mice with unilateral striatal xenografts of human RFP-expressing rU118 glioma (n=3) were treated with a single intracranial injection of VSVΔG-CHIKV 9 days after tumor placement. Mice were euthanized 4, 7 and 15 days later. The glioma rU118 expresses red fluorescent protein reporter. VSVΔG-CHIKV was detected by green immunofluorescent labeling.

VSVΔG-CHIKV not only infected the inoculated cells but additionally showed significant replication after secondary inoculation (24 h) of fresh cultures with media collected from infected cultures, as shown in the plaque analysis (FIG. 3A). In contrast to the human glioma cells, normal human astrocytes showed attenuated infection and little evidence of replication. Similarly, normal mouse glia showed little infection or replication of VSVΔG-CHIKV whereas mouse CT-2A glioma cells displayed both infection and replication (FIG. 3B).

Example 3. Comparison of Recombinant VSV Infection of Glioblastoma

Materials and Methods

To determine the susceptibility of glioma cells to VSVΔG-CHIKV infection, two additional recombinant VSVs, one wild-type (VSVwt) and another chimeric VSV, VSV-LASV-GPC (VSVΔG-LASV) were compared with VSVΔG-CHIKV for their ability to infect and kill either mouse (CT-2A) or human (U118) derived glioma cells.

Results

Twenty-four hours after inoculation (MOI=1) all three viruses showed good infection levels at 24 hpi and evoked cell death at 48 hpi as determined with ethidium homodimer (FIG. 4A,B) in both mouse and human glioma cells. VSVwt showed greater infection and cell death than VSVΔG-CHIKV or VSVΔG-LASV. Non-infected control tumor cells showed no infection and little cell death.

To compare the relative propagation of these three viruses, viral plaque size was measured using monolayer cultures of human (U118, U87) and mouse (CT-2A) glioma. Forty-eight hours after infection both human glioma cell lines yielded robust large plaques; mouse CT-2A yielded smaller plaques for all 3 viruses. The VSVwt plaques were larger than those generated by VSVΔG-CHIKV or VSV-LASV-GPC. (FIG. 4C,D)

Example 4. Type I Interferon Actions on VSVΔG-CHIKV Infection of Human Glioma Interferons (IFNs) are cytokines that play an important role in the induction and maintenance of innate and adaptive immunity, and dysfunctional IFN signaling has been demonstrated as a key mechanism contributing to enhanced infection of cancer cells (Stojdl, et al, *Nat. Med.,* 6:821-825 (2000)).

Materials and Methods

To test whether type I interferon might play a role in the selectivity of VSVΔG-CHIKV infection of cancer cells, glioma cells and normal cells were cultured and pre-treated with 1 or 10 IU of a recombinant hybrid type I interferon (IFN-αA/D that activates both mouse and human type 1 IFN receptors) for 12 h prior to infection with VSVΔG-CHIKV at an MOI of 0.02. Twenty-four hours later, immunostaining was used to quantify the number of cells showing VSVΔG-CHIKV infection.

Results

IFN-α (1 IU, n=6 samples/group) almost completely blocked VSVΔG-CHIKV infection of normal astrocytes compared to no IFN ($p<0.05$ vs. control) (FIG. 5A). In contrast to IFN's block of infection in normal human astrocytes, viral infection of human glioma U118, U87, and U373 was attenuated but not completely blocked by IFN-α at 1 IU (U118, p=0.37; U87, p=0.37; U373, p=0.058; vs no-IFN controls). A greater effect was observed at 10 IU in a dose-dependent manner ($p<0.001$ vs control) (FIG. 5A). VSVΔG-CHIKV showed only modest inhibition by IFN-α in mouse CT-2A glioma (FIG. 5B).

Example 5. VSVΔG-CHIKV Targets Glioma

Materials and Methods

Mouse Procedures

Six- to seven-week-old immunodeficient adult CB17 SCID mice were used for xenograft brain tumor models and postoperative care was performed. Tumors were established by unilateral striatal injection of 2 μl of cell suspension containing $2.5\times10^4$ cells/μl while mice were deeply anesthetized using a combination of ketamine and xylazine (100 and 10 mg/kg of body weight, respectively). Stereotactic intracerebral injections of tumor cells were made into the right striatum (2 mm lateral and 0.5 mm rostral to the bregma at 3 mm depth) using a microsyringe (Hamilton Co., Reno, Nev.) controlled by a stereotactic injector (Stoelting Co., Wood Dale, Ill.). Eight days after tumor placement, mice received virus via intratumoral injection ($3.0\times10^8$ PFU in 2 μl). For bilateral tumor implants, tumor cells were injected into the striatum or cortex (cortical coordinates: 2 mm lateral and 0.5 mm rostral to the bregma at 0.5 mm depth). For some histologic analyses of early states of viral infection, mice were sacrificed after viral inoculation by an anesthetic overdose followed by intracardiac perfusion with 4% paraformaldehyde. In some experiments, mice bearing tumors infected by VSVΔG-CHIKV were euthanized and tissue samples of tumor and control cerebellum were harvested. Tissue samples were dissociated into small pieces and the preparation was used to inoculate cultures of Vero cells to determine the presence or absence of viable virus.

Mice were monitored daily and euthanized if any of the following conditions were observed: (i) weight loss of 25% or more, (ii) immobility, (iii) occurrence of adverse neurological symptoms, or (iv) reaching the end of the observation period of the survival study.

Immunocytochemistry

At the indicated time points, brains were harvested and incubated in 4% (wt/vol) paraformaldehyde at 4° C. for 24 hrs. Brains were subsequently transferred into 30% (vol/vol) sucrose. In preparation for immunofluorescent labeling, brain sections were fixed in 4% paraformaldehyde, rinsed with phosphate-buffered saline (PBS), and permeabilized by washing 3 times for 10 min in PBS with 1% bovine serum albumin (BSA) and 0.4% Triton-X, blocked in washing buffer containing 2% normal horse serum (NHS), then exposed to primary antibody in blocking solution. A primary rabbit anti-wild type VSV antibody (Johnson et al., 1997) or rat anti-VSV antibody was used (overnight incubation; dilution 1:3,000) to immunostain the sections. The VSV antibody binds to multiple VSV proteins, allowing detection of chimeric VSV viruses expressing non-VSV glycoproteins. After multiple washes to eliminate free primary antibody, a secondary goat anti-rabbit antibody conjugated to a green fluorescent molecule (Alexa Fluor 488; A11008; Invitrogen) or anti-rat secondary (2 h; dilution 1:1,000) was used to localize the virus in infected cells. Finally, cells were incubated in nuclear stain Hoechst33342 (5 mg/ml in PBS) or, for cell death experiments, ethidium homodimer 1 (EthD-1; cat no. 40010; Biotium Inc, Fremont, Calif.) 2 μM in PBS for 20 min in the dark. Images were captured using a fluorescent microscope (Olympus IX71, Tokyo, Japan) fitted with a SPOT-RT camera (Diagnostic Instruments, Sterling Heights, Mich.). Contrast and brightness were corrected with universal application to the entire photograph using Adobe Photoshop.
Results
To examine whether VSVΔG-CHIKV can act in vivo, the mouse brain was injected with glioblastoma rU87,rU118, and rU373 cells. Nine days after tumor injection into the striatum of SCID mice, VSVΔG-CHIKV ($7 \times 10^8$ PFU) was injected intracranially in the area of the tumor. Mice were euthanized 4, 7, and 15 days later (FIG. 6). Four days after VSVΔG-CHIKV administration (13 days after injection of cancer cells), the virus showed selective infection of all types of glioma including U118 (n=3) and U373 (n=4). At 7 and 15 dpi, a greater number of tumor cells were selectively infected. In contrast to the infection of glioma, little infection was detected in the normal host brain. These results show that the VSVΔG-CHIKV tested here did not show spread within the brain and did not lead to negative consequences.

Example 6. VSVΔG-CHIKV Enhances Survival in Brain Tumor Bearing Mice

Figure 7:
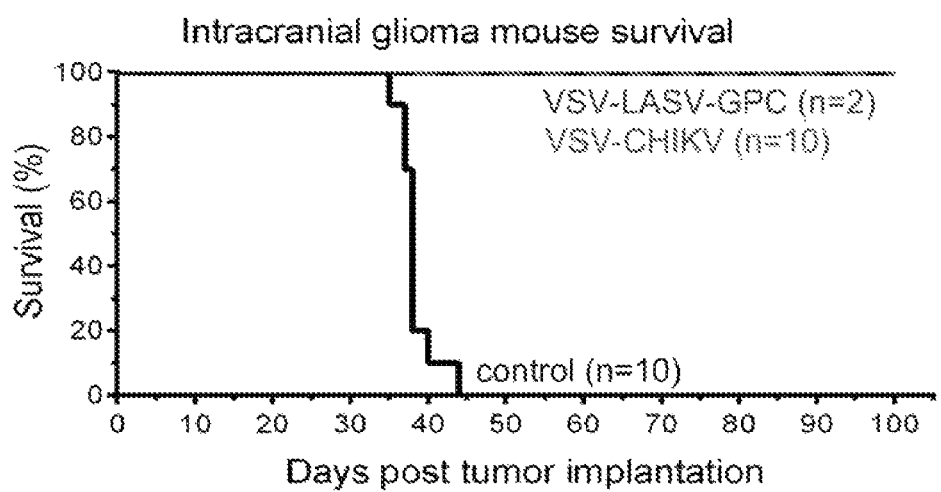
FIG. 7 shows the glioma mouse survival in mice treated with a single intracranial injection of either VSVΔG-CHIKV, VSV-LASV-GPC (2 μl of 3.0×10$^8$PFU for each) or saline (control) 8 days after tumor implantation. VSVΔG-CHIKV-treated mice (n=10) showed complete survival throughout the observation period (100 days) compared to untreated control (n=10 each), and there was no overt difference between VSVΔG-CHIKV-treated mice and VSV-LASV-GPC-treated mice.
Figure 8:
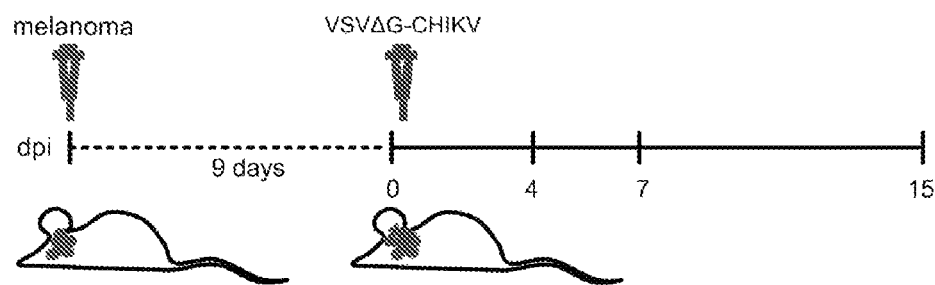
FIG. 8 is a schematic showing time course of in vivo experiments (n=3) of VSVΔG-CHIKV targeting melanoma in brain.
Figures 9A, 9B:
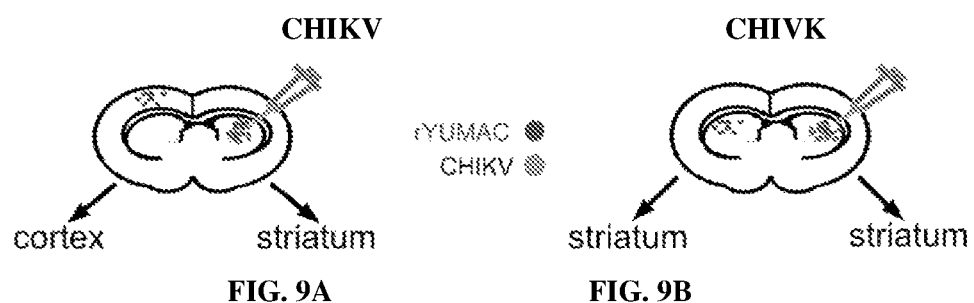
FIGS. 9A and 9B are schematics showing the location of human primary melanoma implanted in SCID mouse brain in cortex (left, 9A) or striatum (right, 9B).
Figure 9C:
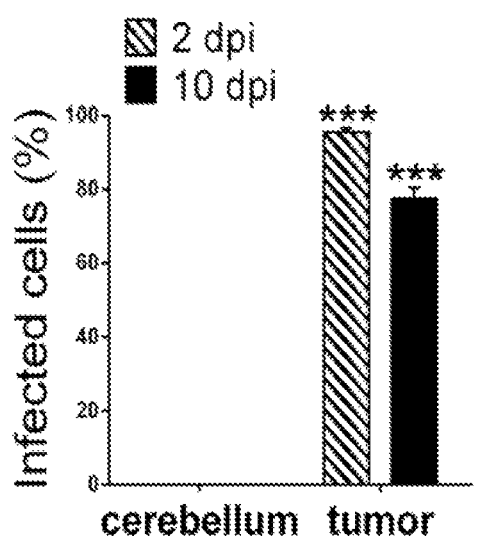
FIG. 9C is a bar graph showing the percentage of VSVΔG-CHIKV infected cells harvested 2 days after VSVΔG-CHIKV injection in tumors.

Materials and Methods
VSVΔG-CHIKV was shown to improve the survival of tumor-bearing mice. Human U87 glioma were implanted into the brains of SCID mice (n=22). After the tumors had expanded for 8 days, VSVΔG-CHIKV was injected into the tumor (n=10); other mice (n=10) served as tumor bearing controls with no virus. As a positive control, VSV-LASV-GPC (n=2) was used which had been previously shown to enhance survival in tumor-bearing mice (Wollmann, et al., *J. Virol.*, 89:6711-6724 (2015)).
Results
VSVΔG-CHIKV greatly enhanced the survival of tumor-bearing mice. All tumor-bearing mice (n=10) not treated with virus showed a lethal response to the expanding tumor with a mean survival of 38 days post-tumor implantation, and a maximum survival of 44 days post-tumor implantation (FIG. 7). A photomicrograph of an untreated brain shows substantial tumor expansion and encroachment into the adjacent normal brain. In contrast, all tumor-bearing mice (n=10) treated intracranially with VSVΔG-CHIKV showed a statistically significant extended long-term survival of 100 days post-tumor implantation (FIG. 7) (p<0.001; log-rank test). At that point, one or two mice were euthanized by anesthetic overdose every few days up to 120 days. None of the tumor-bearing mice treated with VSVΔG-CHIKV showed a lethal response either to tumor-mediated brain dysfunction or to the presence of VSVΔG-CHIKV within the brain. Histological verification in the brains of tumor-bearing mice treated with VSVΔG-CHIKV show an apparent absence of tumor, and an absence of detectable virus in an additional mouse euthanized 108 days after tumor implant and treated with intratumoral VSVΔG-CHIKV.
These results show complete elimination of brain tumors and substantial (complete) increase in survival, at least for the duration of the survival experiments of several months. The tumor-bearing mice (n=2) treated with the positive control VSV-LASV-GPC also showed extended survival (FIG. 7) as previously reported (Wollmann, et al., *J. Virol.*, 89:6711-6724 (2015)). Analysis for expression of red U87 glioma fluorescence revealed a consistently bright fluorescent signal on the injected side. The result demonstrates large red tumors in the brains of 5 mice that did not receive VSVΔG-CHIKV, and the absence of detectable tumor in the brains of 5 other mice that did receive VSVΔG-CHIKV.

Example 7. VSVΔG-CHIKV Infects Human Melanoma

Materials and Methods

VSVΔG-CHIKV can selectively infect other types of brain cancer cells. Nine days after injection and expansion of primary human rYUMAC melanoma into the SCID mouse brain, VSVΔG-CHIKV was injected into the brain (n=3)

Results

As shown by FIG. 8, strong green viral immunofluorescence was found in the tumors with little infection outside the melanoma cells at the different time points examined. At 4 dpi many, but not all, tumor cells showed infection. At 7 dpi and 15 dpi, the percentage of infected cells increased, and the cells showed additional signs of viral infection.

Example 8. VSVΔG-CHIKV Migrates to Multiple Tumors in a Model of Metastatic Brain Cancer The current standard clinical treatment of brain tumors is surgical resection of the malignant tissue, combined with radiotherapy and chemotherapy (Wei, et al., *Mol. Med. Rep.,* 11:2548-2554 (2015); Wollmann, et al., *J. Med. Virol.,* 84:1757-1771 (2012)). However, in patients with high grade brain tumors, neurosurgical removal or focused radiation may eliminate the main tumor body but is generally unable to eliminate the large number of tumor cells that have migrated into the surrounding brain tissue.

Materials and Methods

To evaluate the efficacy and safety of selective reduction of VSVΔG-CHIKV and its impact on melanoma, the left and right side of the SCID mouse brain were implanted with human primary melanoma (in striatum or cortex) (FIG. 9A, 9B). Eight days later, VSVΔG-CHIKV was stereotactically injected unilaterally only into the tumor on the right side of the brain. Eight days later, the animals were euthanized and the brains were examined.

To further confirm VSVΔG-CHIKV selectively infected melanoma in vivo, both sides of the SCID mouse brain (n=3) were implanted with human primary melanoma cells (in striatum). Ten days later, VSVΔG-CHIKV was stereotactically injected into the dorsal region of the tumors on both sides of the brain. Two days later the tumors, along with control samples of cerebellum, were harvested, dissociated, and used to inoculate Vero cells.

Results

VSVΔG-CHIKV completely destroyed the inoculated tumor on the right side of the brain. Additionally, the virus migrated to the contralateral left tumor (striatum and cortex) and began the process of infection and destruction without infecting the intervening normal brain. These results show that VSVΔG-CHIKV can selectively infect multiple brain tumors after injection into a single tumor.

All of the Vero cells were infected by the extracted tumor tissue (99.1%+/−0.62), whereas none of the cultured cells receiving normal cerebellar tissue from the same brain became infected (FIG. 9C). In additional experiments conducted at 10 dpi, a similarly robust infection of Vero cells (77.5%+/−3.0) was found after inoculation with dissociated tumor samples and no detectable infection conferred by normal cerebellar tissue.

Example 9. Mouse Melanoma in Immunocompetent Mouse Brain

Materials and Methods

To test the ability of VSVΔG-CHIKV to target tumor cells in an immunocompetent animal model, B16 mouse melanoma cells were tested.

B16 melanoma cells were injected into the brains of normal C57/B16 mice (n=3). Seven days later after the tumor cells had expanded, VSVΔG-CHIKV ($2.25 \times 10^5$ PFU in 0.75 ul) was injected directly into the brain in the area of the tumor. Three and four days later, brains were harvested.

Results

VSVΔG-CHIKV showed strong infection of cultured mouse melanocytes and generated large plaques indicating infection, replication, and release. The mouse melanoma cells could be distinguished from the host brain by the dark coloration of the melanosomes within the mouse melanoma in contrast to the absence of such a dark coloration in the host brain cells. Green virus immunofluorescence was found primarily in the mouse melanoma cells, with the virus immunofluorescence overlapping with the dark-colored melanoma cells. These results show that the intracranial injected VSVΔG-CHIKV in immunocompromised SCID mice showed negligible spread in the brain and no lethal actions.

Example 10. Intravenous VSVΔG-CHIKV Selectively Infects Subcutaneous Melanoma Materials and Methods To study the potential of the virus to infect distant tumors, eleven days after subcutaneous implant of rYUMAC human melanoma, VSVΔG-CHIKV was injected into the tail vein, and 4 days later mice (n=5) were euthanized.

Results

VSVΔG-CHIKV was found only in the melanoma. The virus was moving toward the center of the tumor, and beginning to eliminate tumor cells at the periphery. No VSVΔG-CHIKV immunoreactivity was found in lung, colon, bladder, kidney, heart, stomach, testis, brain, liver, or spleen. These data demonstrates that the virus shows considerable selectivity to tumors and not to any of the other tissue or organs studied.

Unless defined otherwise, all technical and scientific terms used herein have the same meanings as commonly understood by one of skill in the art to which the invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

---

I claim:

1. A method of treating cancer in a subject comprising administering to a subject with cancer a pharmaceutical composition comprising an effective amount of a chimeric vesicular stomatitis virus (VSV) to treat cancer in the subject, wherein the chimeric VSV comprises a VSV background with Chikungunya virus glycoproteins in place of the VSV glycoprotein (G), wherein the chimeric VSV genome comprises nucleic acid sequences encoding a VSV nucleocapsid protein (N), a VSV phosphoprotein (P), a VSV matrix (M) protein, a VSV large (L) viral polymerase, and Chikungunya virus E3, E2, 6K, and E1 proteins.

2. The method of claim 1, wherein the nucleic acid encoding the E3, E2, 6K, and E1 proteins encodes a Chikungunya virus structural polyprotein that comprises an E3-E2-6K-E1 glycoprotein sequence.

3. The method of claim 1, wherein the chimeric virus encodes the polypeptide of SEQ ID NO: 10 or 11.

4. The method of claim 1, wherein the VSV background is VSV Indiana, VSV New Jersey, VSV Alagoas (formerly Indiana 3), VSV Cocal (formerly Indiana 2), 45685518.1 2 YU 7500 371 USVSV Chandipura, VSV Isfahan, VSV San Juan, VSV Orsay, VSV Glasgow, or a recombinant VSV comprising at least 1 gene from two or more VSV strains or serotypes selected from the group consisting of VSV Indiana, VSV New Jersey, VSV Alagoas (formerly Indiana 3), VSV Cocal (formerly Indiana 2), VSV Chandipura, VSV Isfahan, VSV San Juan, VSV Orsay, and VSV Glasgow.

5. The method of claim 1, wherein the heterologous viral Chikungunya glycoprotein is from prototypic African strain CHIKV S27.

6. The method of claim 1, wherein the genome of the chimeric VSV encodes one or more additional heterologous genes.

7. The method of claim 6 wherein the one or more additional heterologous genes encode a protein that is a therapeutic protein, a reporter, a vaccine antigen, a targeting moiety, or a combination thereof.

8. The method of claim 1, wherein the cancer is selected from the group consisting of multiple myeloma, bone, bladder, brain, breast, cervical, colo-rectal, esophageal, kidney, liver, lung, nasopharangeal, pancreatic, prostate, skin, stomach, and uterine.

9. The method of claim 8, wherein the brain cancer is selected from the group consisting of oligodendroglioma, meningioma, supratentorial ependymona, pineal region tumors, medulloblastoma, infratentorial ependymona, brainstem glioma, schwannomas, pituitary tumors, craniopharyngioma, optic glioma, and astrocytoma, and wherein the chimeric VSV has negligible toxicity for normal and healthy neurons.

10. The method of claim 8, wherein the brain cancer is a glioma or a metastasis thereof and wherein survival of the subject is at least double the length of untreated subjects beginning from the time of administration.

11. The method of claim 10, wherein the brain cancer is glioblastoma.

12. The method of claim 1, wherein the cancer is melanoma or a metastasis thereof.

13. The method of claim 1, wherein the pharmaceutical composition is administered locally to the site of the cancer.

14. The method of claim 1, wherein the pharmaceutical composition is administered to the subject intranasally or by pulmonary delivery.

15. The method of claim 1 further comprising administering to the subject a second therapeutic agent.

16. The method of claim 1, wherein the VSV matrix (M) protein comprises an M51A substitution.

17. The method of claim 1, wherein the VSV matrix (M) protein comprises deletion of amino acid 51 (MA51).

18. The method of claim 1, wherein the chimeric VSV is a replication competent virus.

19. The method of claim 1, further comprising surgery on the subject.

20. The method of claim 19, wherein the surgery is prior to administration of the chimeric VSV.

* * * * *

SEQUENCE LISTING

```
<160> NUMBER OF SEQ ID NOS: 11

<210> SEQ ID NO 1
<211> LENGTH: 1248
<212> TYPE: PRT
<213> ORGANISM: Chikungunya virus

<400> SEQUENCE: 1

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Ala Pro Gln Asn Asn
65                  70                  75                  80

Thr Asn Gln Lys Lys Gln Pro Pro Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175
```

```
Lys Phe Thr His Glu Lys Pro Glu Gly Tyr Tyr Asn Trp His His Gly
            180                 185                 190
Ala Val Gln Tyr Ser Gly Gly Arg Phe Thr Ile Pro Thr Gly Ala Gly
            195                 200                 205
Lys Pro Gly Asp Ser Gly Arg Pro Ile Phe Asp Asn Lys Gly Arg Val
            210                 215                 220
Val Ala Ile Val Leu Gly Gly Ala Asn Glu Gly Ala Arg Thr Ala Leu
225                 230                 235                 240
Ser Val Val Thr Trp Asn Lys Asp Ile Val Thr Lys Ile Thr Pro Glu
            245                 250                 255
Gly Ala Glu Glu Trp Ser Leu Ala Ile Pro Val Met Cys Leu Leu Ala
            260                 265                 270
Asn Thr Thr Phe Pro Cys Ser Gln Pro Pro Cys Ile Pro Cys Cys Tyr
            275                 280                 285
Glu Lys Glu Pro Glu Glu Thr Leu Arg Met Leu Glu Asp Asn Val Met
            290                 295                 300
Arg Pro Gly Tyr Tyr Gln Leu Leu Gln Ala Ser Leu Thr Cys Ser Pro
305                 310                 315                 320
His Arg Gln Arg Arg Ser Thr Lys Asp Asn Phe Asn Val Tyr Lys Ala
            325                 330                 335
Thr Arg Pro Tyr Leu Ala His Cys Pro Asp Cys Gly Glu Gly His Ser
            340                 345                 350
Cys His Ser Pro Val Ala Leu Glu Arg Ile Arg Asn Glu Ala Thr Asp
            355                 360                 365
Gly Thr Leu Lys Ile Gln Val Ser Leu Gln Ile Gly Ile Gly Thr Asp
            370                 375                 380
Asp Ser His Asp Trp Thr Lys Leu Arg Tyr Met Asp Asn His Ile Pro
385                 390                 395                 400
Ala Asp Ala Gly Arg Ala Gly Leu Phe Val Arg Thr Ser Ala Pro Cys
            405                 410                 415
Thr Ile Thr Gly Thr Met Gly His Phe Ile Leu Ala Arg Cys Pro Lys
            420                 425                 430
Gly Glu Thr Leu Thr Val Gly Phe Thr Asp Ser Arg Lys Ile Ser His
            435                 440                 445
Ser Cys Thr His Pro Phe His His Asp Pro Pro Val Ile Gly Arg Glu
450                 455                 460
Lys Phe His Ser Arg Pro Gln His Gly Lys Glu Leu Pro Cys Ser Thr
465                 470                 475                 480
Tyr Val Gln Ser Asn Ala Ala Thr Ala Glu Glu Ile Glu Val His Met
            485                 490                 495
Pro Pro Asp Thr Pro Asp Arg Thr Leu Leu Ser Gln Gln Ser Gly Asn
            500                 505                 510
Val Lys Ile Thr Val Asn Gly Arg Thr Val Arg Tyr Lys Cys Asn Cys
            515                 520                 525
Gly Gly Ser Asn Glu Gly Leu Ile Thr Thr Asp Lys Val Ile Asn Asn
            530                 535                 540
Cys Lys Val Asp Gln Cys His Ala Ala Val Thr Asn His Lys Lys Trp
545                 550                 555                 560
Gln Tyr Asn Ser Pro Leu Val Pro Arg Asn Ala Glu Leu Gly Asp Arg
            565                 570                 575
Lys Gly Lys Ile His Ile Pro Phe Pro Leu Ala Asn Val Thr Cys Met
            580                 585                 590
Val Pro Lys Ala Arg Asn Pro Thr Val Thr Tyr Gly Lys Asn Gln Val
```

```
                595                 600                 605
Ile Met Leu Leu Tyr Pro Asp His Pro Thr Leu Leu Ser Tyr Arg Ser
        610                 615                 620

Met Gly Glu Glu Pro Asn Tyr Gln Glu Glu Trp Val Thr His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Ala Asn Gly Thr
                660                 665                 670

Ala His Gly His Pro His Glu Ile Ile Leu Tyr Tyr Glu Leu Tyr
            675                 680                 685

Pro Thr Met Thr Val Val Val Ser Val Ala Ser Phe Ile Leu Leu
        690                 695                 700

Ser Met Val Gly Met Ala Val Gly Met Cys Met Cys Ala Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
                740                 745                 750

Glu Ala Ala Val Tyr Leu Trp Asn Glu Gln Gln Pro Leu Phe Trp Leu
            755                 760                 765

Gln Ala Leu Ile Pro Leu Ala Ala Leu Ile Val Leu Cys Asn Cys Leu
        770                 775                 780

Arg Leu Leu Pro Cys Cys Cys Lys Thr Leu Ala Phe Leu Ala Val Met
785                 790                 795                 800

Ser Ile Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
                820                 825                 830

Tyr Ser Pro Met Val Leu Glu Met Glu Leu Leu Ser Val Thr Leu Glu
            835                 840                 845

Pro Thr Leu Ser Leu Asp Tyr Ile Thr Cys Glu Tyr Lys Thr Val Ile
850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
        930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro Phe Gly Ala Gly Arg Pro Gly Gln
        995                 1000                1005

Phe Gly Asp Ile Gln Ser Arg Thr Pro Glu Ser Lys Asp Val Tyr
        1010                1015                1020
```

-continued

```
Ala Asn Thr Gln Leu Val Leu Gln Arg Pro Ala Gly Thr Val
    1025                1030                1035

His Val Pro Tyr Ser Gln Ala Pro Ser Gly Phe Lys Tyr Trp Leu
    1040                1045                1050

Lys Glu Arg Gly Ala Ser Leu Gln His Thr Ala Pro Phe Gly Cys
    1055                1060                1065

Gln Ile Ala Thr Asn Pro Val Arg Ala Met Asn Cys Ala Val Gly
    1070                1075                1080

Asn Met Pro Ile Ser Ile Asp Ile Pro Asp Ala Ala Phe Thr Arg
    1085                1090                1095

Val Val Asp Ala Pro Ser Leu Thr Asp Met Ser Cys Glu Val Pro
    1100                1105                1110

Ala Cys Thr His Ser Ser Asp Phe Gly Gly Val Ala Ile Ile Lys
    1115                1120                1125

Tyr Ala Val Ser Lys Lys Gly Lys Cys Ala Val His Ser Met Thr
    1130                1135                1140

Asn Ala Val Thr Ile Arg Glu Ala Glu Ile Glu Val Glu Gly Asn
    1145                1150                1155

Ser Gln Leu Gln Ile Ser Phe Ser Thr Ala Leu Ala Ser Ala Glu
    1160                1165                1170

Phe Arg Val Gln Val Cys Ser Thr Gln Val His Cys Ala Ala Glu
    1175                1180                1185

Cys His Pro Pro Lys Asp His Ile Val Asn Tyr Pro Ala Ser His
    1190                1195                1200

Thr Thr Leu Gly Val Gln Asp Ile Ser Ala Thr Ala Met Ser Trp
    1205                1210                1215

Val Gln Lys Ile Thr Gly Gly Val Gly Leu Val Val Ala Val Ala
    1220                1225                1230

Ala Leu Ile Leu Ile Val Val Leu Cys Val Ser Phe Ser Arg His
    1235                1240                1245

<210> SEQ ID NO 2
<211> LENGTH: 1248
<212> TYPE: PRT
<213> ORGANISM: Chikungunya virus

<400> SEQUENCE: 2

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Lys Asn
    50                  55                  60

Arg Lys Asn Lys Lys Gln Lys Gln Lys Gln Ala Pro Gln Asn Asn
65                  70                  75                  80

Thr Asn Gln Lys Lys Gln Pro Lys Lys Lys Pro Ala Gln Lys Lys
                85                  90                  95

Lys Lys Pro Gly Arg Arg Glu Arg Met Cys Met Lys Ile Glu Asn Asp
                100                 105                 110

Cys Ile Phe Glu Val Lys His Glu Gly Lys Val Thr Gly Tyr Ala Cys
            115                 120                 125

Leu Val Gly Asp Lys Val Met Lys Pro Ala His Val Lys Gly Thr Ile
```

-continued

```
            130                 135                 140
Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
                180                 185                 190

Ala Val Gln Tyr Ser Gly Gly Arg Phe Thr Ile Pro Thr Gly Ala Gly
                195                 200                 205

Lys Pro Gly Asp Ser Gly Arg Pro Ile Phe Asp Asn Lys Gly Arg Val
210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
                260                 265                 270

Asn Thr Thr Phe Pro Cys Ser Gln Pro Pro Cys Ile Pro Cys Cys Tyr
                275                 280                 285

Glu Lys Glu Pro Glu Glu Thr Leu Arg Met Leu Glu Asp Asn Val Met
290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
                340                 345                 350

Cys His Ser Pro Val Ala Leu Glu Arg Ile Arg Asn Glu Ala Thr Asp
                355                 360                 365

Gly Thr Leu Lys Ile Gln Val Ser Leu Gln Ile Gly Ile Gly Thr Asp
                370                 375                 380

Asp Ser His Asp Trp Thr Lys Leu Arg Tyr Met Asp Asn His Ile Pro
385                 390                 395                 400

Ala Asp Ala Gly Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
                420                 425                 430

Gly Glu Thr Leu Thr Val Gly Phe Thr Asp Ser Arg Lys Ile Ser His
                435                 440                 445

Ser Cys Thr His Pro Phe His His Asp Pro Pro Val Ile Gly Arg Glu
                450                 455                 460

Lys Phe His Ser Arg Pro Gln His Gly Lys Glu Leu Pro Cys Ser Thr
465                 470                 475                 480

Tyr Val Gln Ser Asn Ala Ala Thr Ala Glu Glu Ile Glu Val His Met
                485                 490                 495

Pro Pro Asp Thr Pro Asp Arg Thr Leu Leu Ser Gln Gln Ser Gly Asn
                500                 505                 510

Val Lys Ile Thr Val Asn Ser Gln Thr Val Arg Tyr Lys Cys Asn Cys
                515                 520                 525

Gly Gly Ser Asn Glu Gly Leu Ile Thr Thr Asp Lys Val Ile Asn Asn
                530                 535                 540

Cys Lys Val Asp Gln Cys His Ala Ala Val Thr Asn His Lys Lys Trp
545                 550                 555                 560
```

```
Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Met
            580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Ser
    610                 615                 620

Met Gly Glu Glu Pro Asn Tyr Gln Glu Glu Trp Val Thr His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Ala Asn Gly Thr
            660                 665                 670

Ala His Gly His Pro His Glu Ile Ile Leu Tyr Tyr Glu Leu Tyr
        675                 680                 685

Pro Thr Met Thr Val Val Val Ser Val Ala Ser Phe Ile Leu Leu
690                 695                 700

Ser Met Val Gly Met Ala Val Gly Met Cys Met Cys Ala Arg Arg
705                 710                 715                 720

Cys Ile Thr Pro Tyr Glu Leu Thr Pro Gly Ala Thr Val Pro Phe Leu
            725                 730                 735

Leu Ser Leu Ile Cys Cys Ile Arg Thr Ala Lys Ala Ala Thr Tyr Gln
            740                 745                 750

Glu Ala Ala Val Tyr Leu Trp Asn Glu Gln Gln Pro Leu Phe Trp Leu
            755                 760                 765

Gln Ala Leu Ile Pro Leu Ala Ala Leu Ile Val Leu Cys Asn Cys Leu
770                 775                 780

Arg Leu Leu Pro Cys Cys Cys Lys Thr Leu Ala Phe Leu Ala Val Met
785                 790                 795                 800

Ser Ile Gly Ala His Thr Val Ser Ala Tyr Glu His Val Thr Val Ile
            805                 810                 815

Pro Asn Thr Val Gly Val Pro Tyr Lys Thr Leu Val Asn Arg Pro Gly
                820                 825                 830

Tyr Ser Pro Met Val Leu Glu Met Glu Leu Leu Ser Val Thr Leu Glu
            835                 840                 845

Pro Thr Leu Ser Leu Asp Tyr Ile Thr Cys Glu Tyr Lys Thr Val Ile
            850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
                900                 905                 910

Ser Glu Ala His Val Glu Lys Ser Glu Ser Cys Lys Thr Glu Phe Ala
            915                 920                 925

Ser Ala Tyr Arg Ala His Thr Ala Ser Ala Ser Ala Lys Leu Arg Val
            930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975
```

Ser Ala Trp Thr Pro Phe Asp Asn Lys Ile Val Val Tyr Lys Gly Asp
            980                 985                 990

Val Tyr Asn Met Asp Tyr Pro Pro Phe Gly Ala Gly Arg Pro Gly Gln
        995                 1000                1005

Phe Gly Asp Ile Gln Ser Arg Thr Pro Glu Ser Lys Asp Val Tyr
    1010                1015                1020

Ala Asn Thr Gln Leu Val Leu Gln Arg Pro Ala Ala Gly Thr Val
    1025                1030                1035

His Val Pro Tyr Ser Gln Ala Pro Ser Gly Phe Lys Tyr Trp Leu
    1040                1045                1050

Lys Glu Arg Gly Ala Ser Leu Gln His Thr Ala Pro Phe Gly Cys
    1055                1060                1065

Gln Ile Ala Thr Asn Pro Val Arg Ala Met Asn Cys Ala Val Gly
    1070                1075                1080

Asn Met Pro Ile Ser Ile Asp Ile Pro Asp Ala Ala Phe Thr Arg
    1085                1090                1095

Val Val Asp Ala Pro Ser Leu Thr Asp Met Ser Cys Glu Val Pro
    1100                1105                1110

Ala Cys Thr His Ser Ser Asp Phe Gly Gly Val Ala Ile Ile Lys
    1115                1120                1125

Tyr Ala Val Ser Lys Lys Gly Lys Cys Ala Val His Ser Met Thr
    1130                1135                1140

Asn Ala Val Thr Ile Arg Glu Ala Glu Ile Glu Val Glu Gly Asn
    1145                1150                1155

Ser Gln Leu Gln Ile Ser Phe Ser Thr Ala Leu Ala Ser Ala Glu
    1160                1165                1170

Phe Arg Val Gln Val Cys Ser Thr Gln Val His Cys Ala Ala Glu
    1175                1180                1185

Cys His Pro Pro Lys Asp His Ile Val Asn Tyr Pro Ala Ser His
    1190                1195                1200

Thr Thr Leu Gly Val Gln Asp Ile Ser Ala Thr Ala Met Ser Trp
    1205                1210                1215

Val Gln Lys Ile Thr Gly Gly Val Gly Leu Val Val Ala Val Ala
    1220                1225                1230

Ala Leu Ile Leu Ile Val Val Leu Cys Val Ser Phe Ser Arg His
    1235                1240                1245

<210> SEQ ID NO 3
<211> LENGTH: 261
<212> TYPE: PRT
<213> ORGANISM: Artificial Sequence
<220> FEATURE:
<223> OTHER INFORMATION: synthetic polypeptide - Q8JUX5, capsid protein

<400> SEQUENCE: 3

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Ala Pro Gln Asn Asn
65                  70                  75                  80

```
Thr Asn Gln Lys Lys Gln Pro Pro Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
            115                 120                 125

Leu Val Gly Asp Lys Val Met Lys Pro Ala His Val Lys Gly Thr Ile
        130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp
            260

<210> SEQ ID NO 4
<211> LENGTH: 261
<212> TYPE: PRT
<213> ORGANISM: Artificial Sequence
<220> FEATURE:
<223> OTHER INFORMATION: synthetic polypeptide - NP_690589.2 - capsid
      protein

<400> SEQUENCE: 4

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Lys Asn
    50                  55                  60

Arg Lys Asn Lys Lys Gln Lys Gln Lys Gln Ala Pro Gln Asn Asn
65                  70                  75                  80

Thr Asn Gln Lys Lys Gln Pro Pro Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
            115                 120                 125

Leu Val Gly Asp Lys Val Met Lys Pro Ala His Val Lys Gly Thr Ile
        130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175
```

```
Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
            195                 200                 205

Lys Pro Gly Asp Ser Gly Arg Pro Ile Phe Asp Asn Lys Gly Arg Val
            210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp
            260

<210> SEQ ID NO 5
<211> LENGTH: 64
<212> TYPE: PRT
<213> ORGANISM: Artificial Sequence
<220> FEATURE:
<223> OTHER INFORMATION: synthetic polypeptide - Q8JUX5 and
      NP_690589.2 - Assembly protein E3

<400> SEQUENCE: 5

Ser Leu Ala Ile Pro Val Met Cys Leu Leu Ala Asn Thr Thr Phe Pro
1               5                   10                  15

Cys Ser Gln Pro Pro Cys Ile Pro Cys Cys Tyr Glu Lys Glu Pro Glu
            20                  25                  30

Glu Thr Leu Arg Met Leu Glu Asp Asn Val Met Arg Pro Gly Tyr Tyr
            35                  40                  45

Gln Leu Leu Gln Ala Ser Leu Thr Cys Ser Pro His Arg Gln Arg Arg
        50                  55                  60

<210> SEQ ID NO 6
<211> LENGTH: 423
<212> TYPE: PRT
<213> ORGANISM: Artificial Sequence
<220> FEATURE:
<223> OTHER INFORMATION: synthetic polypeptide - Q8JUX5 - Spike
      glycoprotein E2

<400> SEQUENCE: 6

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Val
            20                  25                  30

Ala Leu Glu Arg Ile Arg Asn Glu Ala Thr Asp Gly Thr Leu Lys Ile
            35                  40                  45

Gln Val Ser Leu Gln Ile Gly Ile Gly Thr Asp Asp Ser His Asp Trp
        50                  55                  60

Thr Lys Leu Arg Tyr Met Asp Asn His Ile Pro Ala Asp Ala Gly Arg
65                  70                  75                  80

Ala Gly Leu Phe Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Ser Cys Thr His Pro
            115                 120                 125

Phe His His Asp Pro Pro Val Ile Gly Arg Glu Lys Phe His Ser Arg
            130                 135                 140
```

```
Pro Gln His Gly Lys Glu Leu Pro Cys Ser Thr Tyr Val Gln Ser Asn
145                 150                 155                 160

Ala Ala Thr Ala Glu Glu Ile Glu Val His Met Pro Pro Asp Thr Pro
                165                 170                 175

Asp Arg Thr Leu Leu Ser Gln Gln Ser Gly Asn Val Lys Ile Thr Val
                180                 185                 190

Asn Gly Arg Thr Val Arg Tyr Lys Cys Asn Cys Gly Gly Ser Asn Glu
            195                 200                 205

Gly Leu Ile Thr Thr Asp Lys Val Ile Asn Cys Lys Val Asp Gln
        210                 215                 220

Cys His Ala Ala Val Thr Asn His Lys Lys Trp Gln Tyr Asn Ser Pro
225                 230                 235                 240

Leu Val Pro Arg Asn Ala Glu Leu Gly Asp Arg Lys Gly Lys Ile His
                245                 250                 255

Ile Pro Phe Pro Leu Ala Asn Val Thr Cys Met Val Pro Lys Ala Arg
                260                 265                 270

Asn Pro Thr Val Thr Tyr Gly Lys Asn Gln Val Ile Met Leu Leu Tyr
                275                 280                 285

Pro Asp His Pro Thr Leu Leu Ser Tyr Arg Ser Met Gly Glu Glu Pro
290                 295                 300

Asn Tyr Gln Glu Glu Trp Val Thr His Lys Lys Glu Val Val Leu Thr
305                 310                 315                 320

Val Pro Thr Glu Gly Leu Glu Val Thr Trp Gly Asn Asn Glu Pro Tyr
                325                 330                 335

Lys Tyr Trp Pro Gln Leu Ser Ala Asn Gly Thr Ala His Gly His Pro
                340                 345                 350

His Glu Ile Ile Leu Tyr Tyr Tyr Glu Leu Tyr Pro Thr Met Thr Val
                355                 360                 365

Val Val Val Ser Val Ala Ser Phe Ile Leu Leu Ser Met Val Gly Met
370                 375                 380

Ala Val Gly Met Cys Met Cys Ala Arg Arg Arg Cys Ile Thr Pro Tyr
385                 390                 395                 400

Glu Leu Thr Pro Gly Ala Thr Val Pro Phe Leu Leu Ser Leu Ile Cys
                405                 410                 415

Cys Ile Arg Thr Ala Lys Ala
            420
```

<210> SEQ ID NO 7
<211> LENGTH: 423
<212> TYPE: PRT
<213> ORGANISM: Artificial Sequence
<220> FEATURE:
<223> OTHER INFORMATION: synthetic polypeptide - NP_690589.2 - Spike
      glycoprotein E2

<400> SEQUENCE: 7

```
Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Val
                20                  25                  30

Ala Leu Glu Arg Ile Arg Asn Glu Ala Thr Asp Gly Thr Leu Lys Ile
            35                  40                  45

Gln Val Ser Leu Gln Ile Gly Ile Gly Thr Asp Ser His Asp Trp
50                  55                  60

Thr Lys Leu Arg Tyr Met Asp Asn His Ile Pro Ala Asp Ala Gly Arg
```

```
            65                  70                  75                  80
        Ala Gly Leu Phe Val Arg Thr Ser Ala Pro Cys Thr Ile Thr Gly Thr
                        85                  90                  95

Met Gly His Phe Ile Leu Ala Arg Cys Pro Lys Gly Glu Thr Leu Thr
                        100                 105                 110

Val Gly Phe Thr Asp Ser Arg Lys Ile Ser His Ser Cys Thr His Pro
                        115                 120                 125

Phe His His Asp Pro Pro Val Ile Gly Arg Glu Lys Phe His Ser Arg
        130                 135                 140

Pro Gln His Gly Lys Glu Leu Pro Cys Ser Thr Tyr Val Gln Ser Asn
        145                 150                 155                 160

Ala Ala Thr Ala Glu Glu Ile Glu Val His Met Pro Pro Asp Thr Pro
                        165                 170                 175

Asp Arg Thr Leu Leu Ser Gln Gln Ser Gly Asn Val Lys Ile Thr Val
                        180                 185                 190

Asn Ser Gln Thr Val Arg Tyr Lys Cys Asn Cys Gly Gly Ser Asn Glu
                        195                 200                 205

Gly Leu Ile Thr Thr Asp Lys Val Ile Asn Cys Lys Val Asp Gln
        210                 215                 220

Cys His Ala Ala Val Thr Asn His Lys Lys Trp Gln Tyr Asn Ser Pro
        225                 230                 235                 240

Leu Val Pro Arg Asn Ala Glu Leu Gly Asp Arg Lys Gly Lys Ile His
                        245                 250                 255

Ile Pro Phe Pro Leu Ala Asn Val Thr Cys Met Val Pro Lys Ala Arg
                        260                 265                 270

Asn Pro Thr Val Thr Tyr Gly Lys Asn Gln Val Ile Met Leu Leu Tyr
                        275                 280                 285

Pro Asp His Pro Thr Leu Leu Ser Tyr Arg Ser Met Gly Glu Glu Pro
                        290                 295                 300

Asn Tyr Gln Glu Glu Trp Val Thr His Lys Lys Glu Val Val Leu Thr
        305                 310                 315                 320

Val Pro Thr Glu Gly Leu Glu Val Thr Trp Gly Asn Asn Glu Pro Tyr
                        325                 330                 335

Lys Tyr Trp Pro Gln Leu Ser Ala Asn Gly Thr Ala His Gly His Pro
                        340                 345                 350

His Glu Ile Ile Leu Tyr Tyr Tyr Glu Leu Tyr Pro Thr Met Thr Val
                        355                 360                 365

Val Val Val Ser Val Ala Ser Phe Ile Leu Leu Ser Met Val Gly Met
        370                 375                 380

Ala Val Gly Met Cys Met Cys Ala Arg Arg Arg Cys Ile Thr Pro Tyr
        385                 390                 395                 400

Glu Leu Thr Pro Gly Ala Thr Val Pro Phe Leu Leu Ser Leu Ile Cys
                        405                 410                 415

Cys Ile Arg Thr Ala Lys Ala
                        420

<210> SEQ ID NO 8
<211> LENGTH: 61
<212> TYPE: PRT
<213> ORGANISM: Artificial Sequence
<220> FEATURE:
<223> OTHER INFORMATION: synthetic polypeptide - Q8JUX5 and
      NP_690589.2 - 6K protein

<400> SEQUENCE: 8
```

```
Ala Thr Tyr Gln Glu Ala Ala Val Tyr Leu Trp Asn Glu Gln Gln Pro
1               5                   10                  15

Leu Phe Trp Leu Gln Ala Leu Ile Pro Leu Ala Ala Leu Ile Val Leu
            20                  25                  30

Cys Asn Cys Leu Arg Leu Leu Pro Cys Cys Cys Lys Thr Leu Ala Phe
            35                  40                  45

Leu Ala Val Met Ser Ile Gly Ala His Thr Val Ser Ala
            50                  55                  60
```

<210> SEQ ID NO 9
<211> LENGTH: 439
<212> TYPE: PRT
<213> ORGANISM: Artificial Sequence
<220> FEATURE:
<223> OTHER INFORMATION: synthetic polypeptide - Q8JUX5 and
      NP_690589.2 - Spike glycoprotein E1

<400> SEQUENCE: 9

```
Tyr Glu His Val Thr Val Ile Pro Asn Thr Val Gly Val Pro Tyr Lys
1               5                   10                  15

Thr Leu Val Asn Arg Pro Gly Tyr Ser Pro Met Val Leu Glu Met Glu
            20                  25                  30

Leu Leu Ser Val Thr Leu Glu Pro Thr Leu Ser Leu Asp Tyr Ile Thr
            35                  40                  45

Cys Glu Tyr Lys Thr Val Ile Pro Ser Pro Tyr Val Lys Cys Cys Gly
            50                  55                  60

Thr Ala Glu Cys Lys Asp Lys Asn Leu Pro Asp Tyr Ser Cys Lys Val
65                  70                  75                  80

Phe Thr Gly Val Tyr Pro Phe Met Trp Gly Gly Ala Tyr Cys Phe Cys
                85                  90                  95

Asp Ala Glu Asn Thr Gln Leu Ser Glu Ala His Val Glu Lys Ser Glu
            100                 105                 110

Ser Cys Lys Thr Glu Phe Ala Ser Ala Tyr Arg Ala His Thr Ala Ser
            115                 120                 125

Ala Ser Ala Lys Leu Arg Val Leu Tyr Gln Gly Asn Asn Ile Thr Val
            130                 135                 140

Thr Ala Tyr Ala Asn Gly Asp His Ala Val Thr Val Lys Asp Ala Lys
145                 150                 155                 160

Phe Ile Val Gly Pro Met Ser Ser Ala Trp Thr Pro Phe Asp Asn Lys
                165                 170                 175

Ile Val Val Tyr Lys Gly Asp Val Tyr Asn Met Asp Tyr Pro Pro Phe
            180                 185                 190

Gly Ala Gly Arg Pro Gly Gln Phe Gly Asp Ile Gln Ser Arg Thr Pro
            195                 200                 205

Glu Ser Lys Asp Val Tyr Ala Asn Thr Gln Leu Val Leu Gln Arg Pro
            210                 215                 220

Ala Ala Gly Thr Val His Val Pro Tyr Ser Gln Ala Pro Ser Gly Phe
225                 230                 235                 240

Lys Tyr Trp Leu Lys Glu Arg Gly Ala Ser Leu Gln His Thr Ala Pro
                245                 250                 255

Phe Gly Cys Gln Ile Ala Thr Asn Pro Val Arg Ala Met Asn Cys Ala
            260                 265                 270

Val Gly Asn Met Pro Ile Ser Ile Asp Ile Pro Asp Ala Ala Phe Thr
            275                 280                 285

Arg Val Val Asp Ala Pro Ser Leu Thr Asp Met Ser Cys Glu Val Pro
            290                 295                 300
```

```
Ala Cys Thr His Ser Ser Asp Phe Gly Gly Val Ala Ile Ile Lys Tyr
305                 310                 315                 320

Ala Val Ser Lys Lys Gly Lys Cys Ala Val His Ser Met Thr Asn Ala
                325                 330                 335

Val Thr Ile Arg Glu Ala Glu Ile Glu Val Glu Gly Asn Ser Gln Leu
            340                 345                 350

Gln Ile Ser Phe Ser Thr Ala Leu Ala Ser Ala Glu Phe Arg Val Gln
        355                 360                 365

Val Cys Ser Thr Gln Val His Cys Ala Ala Glu Cys His Pro Pro Lys
370                 375                 380

Asp His Ile Val Asn Tyr Pro Ala Ser His Thr Thr Leu Gly Val Gln
385                 390                 395                 400

Asp Ile Ser Ala Thr Ala Met Ser Trp Val Gln Lys Ile Thr Gly Gly
                405                 410                 415

Val Gly Leu Val Val Ala Val Ala Ala Leu Ile Leu Ile Val Val Leu
            420                 425                 430

Cys Val Ser Phe Ser Arg His
        435
```

```
<210> SEQ ID NO 10
<211> LENGTH: 987
<212> TYPE: PRT
<213> ORGANISM: Artificial Sequence
<220> FEATURE:
<223> OTHER INFORMATION: synthetic polypeptide - Q8JUX5 - E3-E2-6K-E1

<400> SEQUENCE: 10
```

```
Ser Leu Ala Ile Pro Val Met Cys Leu Leu Ala Asn Thr Thr Phe Pro
1               5                   10                  15

Cys Ser Gln Pro Pro Cys Ile Pro Cys Cys Tyr Glu Lys Glu Pro Glu
                20                  25                  30

Glu Thr Leu Arg Met Leu Glu Asp Asn Val Met Arg Pro Gly Tyr Tyr
            35                  40                  45

Gln Leu Leu Gln Ala Ser Leu Thr Cys Ser Pro His Arg Gln Arg Arg
        50                  55                  60

Ser Thr Lys Asp Asn Phe Asn Val Tyr Lys Ala Thr Arg Pro Tyr Leu
65                  70                  75                  80

Ala His Cys Pro Asp Cys Gly Glu Gly His Ser Cys His Ser Pro Val
                85                  90                  95

Ala Leu Glu Arg Ile Arg Asn Glu Ala Thr Asp Gly Thr Leu Lys Ile
            100                 105                 110

Gln Val Ser Leu Gln Ile Gly Ile Gly Thr Asp Asp Ser His Asp Trp
        115                 120                 125

Thr Lys Leu Arg Tyr Met Asp Asn His Ile Pro Ala Asp Ala Gly Arg
    130                 135                 140

Ala Gly Leu Phe Val Arg Thr Ser Ala Pro Cys Thr Ile Thr Gly Thr
145                 150                 155                 160

Met Gly His Phe Ile Leu Ala Arg Cys Pro Lys Gly Glu Thr Leu Thr
                165                 170                 175

Val Gly Phe Thr Asp Ser Arg Lys Ile Ser His Ser Cys Thr His Pro
            180                 185                 190

Phe His His Asp Pro Pro Val Ile Gly Arg Glu Lys Phe His Ser Arg
        195                 200                 205

Pro Gln His Gly Lys Glu Leu Pro Cys Ser Thr Tyr Val Gln Ser Asn
    210                 215                 220
```

```
Ala Ala Thr Ala Glu Glu Ile Glu Val His Met Pro Pro Asp Thr Pro
225                 230                 235                 240

Asp Arg Thr Leu Leu Ser Gln Gln Ser Gly Asn Val Lys Ile Thr Val
            245                 250                 255

Asn Gly Arg Thr Val Arg Tyr Lys Cys Asn Cys Gly Gly Ser Asn Glu
            260                 265                 270

Gly Leu Ile Thr Thr Asp Lys Val Ile Asn Asn Cys Lys Val Asp Gln
            275                 280             285

Cys His Ala Ala Val Thr Asn His Lys Lys Trp Gln Tyr Asn Ser Pro
        290                 295                 300

Leu Val Pro Arg Asn Ala Glu Leu Gly Asp Arg Lys Gly Lys Ile His
305                 310                 315                 320

Ile Pro Phe Pro Leu Ala Asn Val Thr Cys Met Val Pro Lys Ala Arg
                325                 330                 335

Asn Pro Thr Val Thr Tyr Gly Lys Asn Gln Val Ile Met Leu Leu Tyr
            340                 345                 350

Pro Asp His Pro Thr Leu Leu Ser Tyr Arg Ser Met Gly Glu Glu Pro
        355                 360                 365

Asn Tyr Gln Glu Glu Trp Val Thr His Lys Lys Glu Val Val Leu Thr
370                 375                 380

Val Pro Thr Glu Gly Leu Glu Val Thr Trp Gly Asn Asn Glu Pro Tyr
385                 390                 395                 400

Lys Tyr Trp Pro Gln Leu Ser Ala Asn Gly Thr Ala His Gly His Pro
                405                 410                 415

His Glu Ile Ile Leu Tyr Tyr Glu Leu Tyr Pro Thr Met Thr Val
            420                 425                 430

Val Val Val Ser Val Ala Ser Phe Ile Leu Leu Ser Met Val Gly Met
            435                 440                 445

Ala Val Gly Met Cys Met Cys Ala Arg Arg Arg Cys Ile Thr Pro Tyr
        450                 455                 460

Glu Leu Thr Pro Gly Ala Thr Val Pro Phe Leu Leu Ser Leu Ile Cys
465                 470                 475                 480

Cys Ile Arg Thr Ala Lys Ala Ala Thr Tyr Gln Glu Ala Ala Val Tyr
            485                 490                 495

Leu Trp Asn Glu Gln Gln Pro Leu Phe Trp Leu Gln Ala Leu Ile Pro
            500                 505                 510

Leu Ala Ala Leu Ile Val Leu Cys Asn Cys Leu Arg Leu Leu Pro Cys
            515                 520                 525

Cys Cys Lys Thr Leu Ala Phe Leu Ala Val Met Ser Ile Gly Ala His
            530                 535                 540

Thr Val Ser Ala Tyr Glu His Val Thr Val Ile Pro Asn Thr Val Gly
545                 550                 555                 560

Val Pro Tyr Lys Thr Leu Val Asn Arg Pro Gly Tyr Ser Pro Met Val
                565                 570                 575

Leu Glu Met Glu Leu Leu Ser Val Thr Leu Glu Pro Thr Leu Ser Leu
                580                 585                 590

Asp Tyr Ile Thr Cys Glu Tyr Lys Thr Val Ile Pro Ser Pro Tyr Val
            595                 600                 605

Lys Cys Cys Gly Thr Ala Glu Cys Lys Asp Lys Asn Leu Pro Asp Tyr
        610                 615                 620

Ser Cys Lys Val Phe Thr Gly Val Tyr Pro Phe Met Trp Gly Gly Ala
625                 630                 635                 640
```

```
Tyr Cys Phe Cys Asp Ala Glu Asn Thr Gln Leu Ser Glu Ala His Val
                645                 650                 655

Glu Lys Ser Glu Ser Cys Lys Thr Glu Phe Ala Ser Ala Tyr Arg Ala
            660                 665                 670

His Thr Ala Ser Ala Ser Ala Lys Leu Arg Val Leu Tyr Gln Gly Asn
        675                 680                 685

Asn Ile Thr Val Thr Ala Tyr Ala Asn Gly Asp His Ala Val Thr Val
    690                 695                 700

Lys Asp Ala Lys Phe Ile Val Gly Pro Met Ser Ser Ala Trp Thr Pro
705                 710                 715                 720

Phe Asp Asn Lys Ile Val Val Tyr Lys Gly Asp Val Tyr Asn Met Asp
                725                 730                 735

Tyr Pro Pro Phe Gly Ala Gly Arg Pro Gly Gln Phe Gly Asp Ile Gln
            740                 745                 750

Ser Arg Thr Pro Glu Ser Lys Asp Val Tyr Ala Asn Thr Gln Leu Val
        755                 760                 765

Leu Gln Arg Pro Ala Ala Gly Thr Val His Val Pro Tyr Ser Gln Ala
    770                 775                 780

Pro Ser Gly Phe Lys Tyr Trp Leu Lys Glu Arg Gly Ala Ser Leu Gln
785                 790                 795                 800

His Thr Ala Pro Phe Gly Cys Gln Ile Ala Thr Asn Pro Val Arg Ala
                805                 810                 815

Met Asn Cys Ala Val Gly Asn Met Pro Ile Ser Ile Asp Ile Pro Asp
            820                 825                 830

Ala Ala Phe Thr Arg Val Val Asp Ala Pro Ser Leu Thr Asp Met Ser
        835                 840                 845

Cys Glu Val Pro Ala Cys Thr His Ser Ser Asp Phe Gly Gly Val Ala
    850                 855                 860

Ile Ile Lys Tyr Ala Val Ser Lys Lys Gly Lys Cys Ala Val His Ser
865                 870                 875                 880

Met Thr Asn Ala Val Thr Ile Arg Glu Ala Glu Ile Glu Val Glu Gly
                885                 890                 895

Asn Ser Gln Leu Gln Ile Ser Phe Ser Thr Ala Leu Ala Ser Ala Glu
            900                 905                 910

Phe Arg Val Gln Val Cys Ser Thr Gln Val His Cys Ala Ala Glu Cys
        915                 920                 925

His Pro Pro Lys Asp His Ile Val Asn Tyr Pro Ala Ser His Thr Thr
    930                 935                 940

Leu Gly Val Gln Asp Ile Ser Ala Thr Ala Met Ser Trp Val Gln Lys
945                 950                 955                 960

Ile Thr Gly Gly Val Gly Leu Val Val Ala Val Ala Ala Leu Ile Leu
                965                 970                 975

Ile Val Val Leu Cys Val Ser Phe Ser Arg His
            980                 985

<210> SEQ ID NO 11
<211> LENGTH: 987
<212> TYPE: PRT
<213> ORGANISM: Artificial Sequence
<220> FEATURE:
<223> OTHER INFORMATION: synthetic polypeptide - NP_690589.2 -
      E3-E2-6K-E1

<400> SEQUENCE: 11

Ser Leu Ala Ile Pro Val Met Cys Leu Leu Ala Asn Thr Thr Phe Pro
1               5                   10                  15
```

-continued

```
Cys Ser Gln Pro Pro Cys Ile Pro Cys Cys Tyr Glu Lys Glu Pro Glu
         20                  25                  30

Glu Thr Leu Arg Met Leu Glu Asp Asn Val Met Arg Pro Gly Tyr Tyr
             35                  40                  45

Gln Leu Leu Gln Ala Ser Leu Thr Cys Ser Pro His Arg Gln Arg Arg
 50                  55                  60

Ser Thr Lys Asp Asn Phe Asn Val Tyr Lys Ala Thr Arg Pro Tyr Leu
 65                  70                  75                  80

Ala His Cys Pro Asp Cys Gly Glu Gly His Ser Cys His Ser Pro Val
                 85                  90                  95

Ala Leu Glu Arg Ile Arg Asn Glu Ala Thr Asp Gly Thr Leu Lys Ile
                100                 105                 110

Gln Val Ser Leu Gln Ile Gly Ile Gly Thr Asp Ser His Asp Trp
             115                 120                 125

Thr Lys Leu Arg Tyr Met Asp Asn His Ile Pro Ala Asp Ala Gly Arg
130                 135                 140

Ala Gly Leu Phe Val Arg Thr Ser Ala Pro Cys Thr Ile Thr Gly Thr
145                 150                 155                 160

Met Gly His Phe Ile Leu Ala Arg Cys Pro Lys Gly Glu Thr Leu Thr
                165                 170                 175

Val Gly Phe Thr Asp Ser Arg Lys Ile Ser His Ser Cys Thr His Pro
             180                 185                 190

Phe His His Asp Pro Pro Val Ile Gly Arg Glu Lys Phe His Ser Arg
             195                 200                 205

Pro Gln His Gly Lys Glu Leu Pro Cys Ser Thr Tyr Val Gln Ser Asn
    210                 215                 220

Ala Ala Thr Ala Glu Glu Ile Glu Val His Met Pro Pro Asp Thr Pro
225                 230                 235                 240

Asp Arg Thr Leu Leu Ser Gln Ser Gly Asn Val Lys Ile Thr Val
                245                 250                 255

Asn Ser Gln Thr Val Arg Tyr Lys Cys Asn Cys Gly Gly Ser Asn Glu
            260                 265                 270

Gly Leu Ile Thr Thr Asp Lys Val Ile Asn Asn Cys Lys Val Asp Gln
            275                 280                 285

Cys His Ala Ala Val Thr Asn His Lys Lys Trp Gln Tyr Asn Ser Pro
    290                 295                 300

Leu Val Pro Arg Asn Ala Glu Leu Gly Asp Arg Lys Gly Lys Ile His
305                 310                 315                 320

Ile Pro Phe Pro Leu Ala Asn Val Thr Cys Met Val Pro Lys Ala Arg
                325                 330                 335

Asn Pro Thr Val Thr Tyr Gly Lys Asn Gln Val Ile Met Leu Leu Tyr
            340                 345                 350

Pro Asp His Pro Thr Leu Leu Ser Tyr Arg Ser Met Gly Glu Glu Pro
    355                 360                 365

Asn Tyr Gln Glu Glu Trp Val Thr His Lys Lys Glu Val Val Leu Thr
            370                 375                 380

Val Pro Thr Glu Gly Leu Glu Val Thr Trp Gly Asn Asn Glu Pro Tyr
385                 390                 395                 400

Lys Tyr Trp Pro Gln Leu Ser Ala Asn Gly Thr Ala His Gly His Pro
                405                 410                 415

His Glu Ile Ile Leu Tyr Tyr Tyr Glu Leu Tyr Pro Thr Met Thr Val
            420                 425                 430
```

-continued

Val Val Val Ser Val Ala Ser Phe Ile Leu Leu Ser Met Val Gly Met
            435                 440                 445
Ala Val Gly Met Cys Met Cys Ala Arg Arg Arg Cys Ile Thr Pro Tyr
450                 455                 460
Glu Leu Thr Pro Gly Ala Thr Val Pro Phe Leu Leu Ser Leu Ile Cys
465                 470                 475                 480
Cys Ile Arg Thr Ala Lys Ala Ala Thr Tyr Gln Glu Ala Ala Val Tyr
            485                 490                 495
Leu Trp Asn Glu Gln Pro Leu Phe Trp Leu Gln Ala Leu Ile Pro
            500                 505                 510
Leu Ala Ala Leu Ile Val Leu Cys Asn Cys Leu Arg Leu Leu Pro Cys
            515                 520                 525
Cys Cys Lys Thr Leu Ala Phe Leu Ala Val Met Ser Ile Gly Ala His
            530                 535                 540
Thr Val Ser Ala Tyr Glu His Val Thr Val Ile Pro Asn Thr Val Gly
545                 550                 555                 560
Val Pro Tyr Lys Thr Leu Val Asn Arg Pro Gly Tyr Ser Pro Met Val
            565                 570                 575
Leu Glu Met Glu Leu Leu Ser Val Thr Leu Glu Pro Thr Leu Ser Leu
            580                 585                 590
Asp Tyr Ile Thr Cys Glu Tyr Lys Thr Val Ile Pro Ser Pro Tyr Val
            595                 600                 605
Lys Cys Cys Gly Thr Ala Glu Cys Lys Asp Lys Asn Leu Pro Asp Tyr
610                 615                 620
Ser Cys Lys Val Phe Thr Gly Val Tyr Pro Phe Met Trp Gly Gly Ala
625                 630                 635                 640
Tyr Cys Phe Cys Asp Ala Glu Asn Thr Gln Leu Ser Glu Ala His Val
            645                 650                 655
Glu Lys Ser Glu Ser Cys Lys Thr Glu Phe Ala Ser Ala Tyr Arg Ala
            660                 665                 670
His Thr Ala Ser Ala Ser Ala Lys Leu Arg Val Leu Tyr Gln Gly Asn
            675                 680                 685
Asn Ile Thr Val Thr Ala Tyr Ala Asn Gly Asp His Ala Val Thr Val
            690                 695                 700
Lys Asp Ala Lys Phe Ile Val Gly Pro Met Ser Ser Ala Trp Thr Pro
705                 710                 715                 720
Phe Asp Asn Lys Ile Val Val Tyr Lys Gly Asp Val Tyr Asn Met Asp
                    725                 730                 735
Tyr Pro Pro Phe Gly Ala Gly Arg Pro Gly Gln Phe Gly Asp Ile Gln
            740                 745                 750
Ser Arg Thr Pro Glu Ser Lys Asp Val Tyr Ala Asn Thr Gln Leu Val
            755                 760                 765
Leu Gln Arg Pro Ala Ala Gly Thr Val His Val Pro Tyr Ser Gln Ala
            770                 775                 780
Pro Ser Gly Phe Lys Tyr Trp Leu Lys Glu Arg Gly Ala Ser Leu Gln
785                 790                 795                 800
His Thr Ala Pro Phe Gly Cys Gln Ile Ala Thr Asn Pro Val Arg Ala
                    805                 810                 815
Met Asn Cys Ala Val Gly Asn Met Pro Ile Ser Ile Asp Ile Pro Asp
            820                 825                 830
Ala Ala Phe Thr Arg Val Val Asp Ala Pro Ser Leu Thr Asp Met Ser
            835                 840                 845
Cys Glu Val Pro Ala Cys Thr His Ser Ser Asp Phe Gly Gly Val Ala

```
                850                 855                 860
Ile Ile Lys Tyr Ala Val Ser Lys Lys Gly Lys Cys Ala Val His Ser
865                 870                 875                 880

Met Thr Asn Ala Val Thr Ile Arg Glu Ala Glu Ile Glu Val Glu Gly
                885                 890                 895

Asn Ser Gln Leu Gln Ile Ser Phe Ser Thr Ala Leu Ala Ser Ala Glu
                900                 905                 910

Phe Arg Val Gln Val Cys Ser Thr Gln Val His Cys Ala Ala Glu Cys
            915                 920                 925

His Pro Pro Lys Asp His Ile Val Asn Tyr Pro Ala Ser His Thr Thr
        930                 935                 940

Leu Gly Val Gln Asp Ile Ser Ala Thr Ala Met Ser Trp Val Gln Lys
945                 950                 955                 960

Ile Thr Gly Gly Val Gly Leu Val Val Ala Val Ala Ala Leu Ile Leu
                965                 970                 975

Ile Val Val Leu Cys Val Ser Phe Ser Arg His
                980                 985
```